US009186328B2

(12) United States Patent
Dodd et al.

(10) Patent No.: US 9,186,328 B2
(45) Date of Patent: *Nov. 17, 2015

(54) FORMULATION OF DICLOFENAC

(71) Applicant: iCeutica Pty Ltd., Philadelphia, PA (US)

(72) Inventors: Aaron Dodd, Centennial Park (AU);
Felix Meiser, Mount Claremont (AU);
Marck Norret, Darlington (AU);
Adrian Russell, Rivervale (AU); H William Bosch, Bryn Mawr, PA (US)

(73) Assignee: iCeutica Pty Ltd., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/622,050

(22) Filed: Feb. 13, 2015

(65) Prior Publication Data

US 2015/0150824 A1  Jun. 4, 2015

Related U.S. Application Data

(63) Continuation of application No. 14/277,287, filed on May 14, 2014, now Pat. No. 9,017,721, which is a continuation of application No. 14/167,652, filed on Jan. 29, 2014, now Pat. No. 8,999,387, which is a continuation of application No. 13/266,122, filed as application No. PCT/AU2010/000471 on Apr. 23, 2010, now Pat. No. 8,735,450.

(60) Provisional application No. 61/172,291, filed on Apr. 24, 2009.

(30) Foreign Application Priority Data

Apr. 24, 2009 (AU) ................. 2009901748

(51) Int. Cl.
*A61K 9/14* (2006.01)
*A61K 31/196* (2006.01)
*A61K 9/51* (2006.01)
*A61K 9/00* (2006.01)
*A61K 9/48* (2006.01)
*A61K 9/16* (2006.01)
*A61K 47/12* (2006.01)
*A61K 47/20* (2006.01)

(52) U.S. Cl.
CPC ............... *A61K 9/14* (2013.01); *A61K 9/0087* (2013.01); *A61K 9/143* (2013.01); *A61K 9/145* (2013.01); *A61K 9/146* (2013.01); *A61K 9/16* (2013.01); *A61K 9/4808* (2013.01); *A61K 9/4825* (2013.01); *A61K 9/513* (2013.01); *A61K 9/5115* (2013.01); *A61K 9/5123* (2013.01); *A61K 9/5192* (2013.01); *A61K 31/196* (2013.01); *A61K 47/12* (2013.01); *A61K 47/20* (2013.01); *Y10T 428/2982* (2015.01)

(58) Field of Classification Search
None
See application file for complete search history.

(56) References Cited

U.S. PATENT DOCUMENTS

| 5,145,684 | A | 9/1992 | Liversidge et al. |
|---|---|---|---|
| 5,202,129 | A | 4/1993 | Samejima et al. |
| 5,478,705 | A | 12/1995 | Czekai et al. |
| 5,500,331 | A | 3/1996 | Czekai et al. |
| 5,518,187 | A | 5/1996 | Bruno et al. |
| 5,518,738 | A | 5/1996 | Eickhoff et al. |
| 6,592,903 | B2 | 7/2003 | Ryde et al. |
| 6,634,576 | B2 | 10/2003 | Verhoff et al. |
| 6,908,626 | B2 | 6/2005 | Cooper et al. |
| 7,101,576 | B2 | 9/2006 | Hovey et al. |
| 2004/0022846 | A1 | 2/2004 | Depui et al. |
| 2005/0233001 | A1 | 10/2005 | Hovey et al. |
| 2006/0204588 | A1 | 9/2006 | Liversidge et al. |
| 2006/0287346 | A1 | 12/2006 | Van Schie |
| 2008/0152720 | A1 | 6/2008 | Jenkins et al. |
| 2009/0028948 | A1 | 1/2009 | Payne et al. |
| 2009/0035366 | A1 | 2/2009 | Liversidge et al. |
| 2010/0092563 | A1 | 4/2010 | Raffaele et al. |
| 2012/0135047 | A1 | 5/2012 | Dodd et al. |
| 2013/0209569 | A1 | 8/2013 | Dodd et al. |

FOREIGN PATENT DOCUMENTS

| WO | WO 97/02017 | 1/1997 |
|---|---|---|
| WO | WO 2006/069419 | 7/2006 |
| WO | WO 2006/116596 | 11/2006 |
| WO | WO 2006/133954 | 12/2006 |
| WO | WO 2007/070851 | 6/2007 |
| WO | WO 2007/070852 | 6/2007 |

(Continued)

OTHER PUBLICATIONS

Sharon Hertz, MD; NDA Approval letter, NDA No. 204592; reference ID 3392875; Deputy Director, Division of Anesthesia, Analgesia and Adduction Products, Office of Drug Evaluation II, Center for Drug Evaluation and Research; Oct. 18, 2013; 6 pages.

(Continued)

*Primary Examiner* — Frederick Krass
*Assistant Examiner* — Michael P Cohen
(74) *Attorney, Agent, or Firm* — Fish & Richardson P.C.

(57) ABSTRACT

The present invention relates to methods for producing particles of diclofenac using dry milling processes as well as compositions comprising diclofenac, medicaments produced using diclofenac in particulate form and/or compositions, and to methods of treatment of an animal, including man, using a therapeutically effective amount of diclofenac administered by way of said medicaments.

30 Claims, 20 Drawing Sheets

(56) References Cited

FOREIGN PATENT DOCUMENTS

Figure 1H:
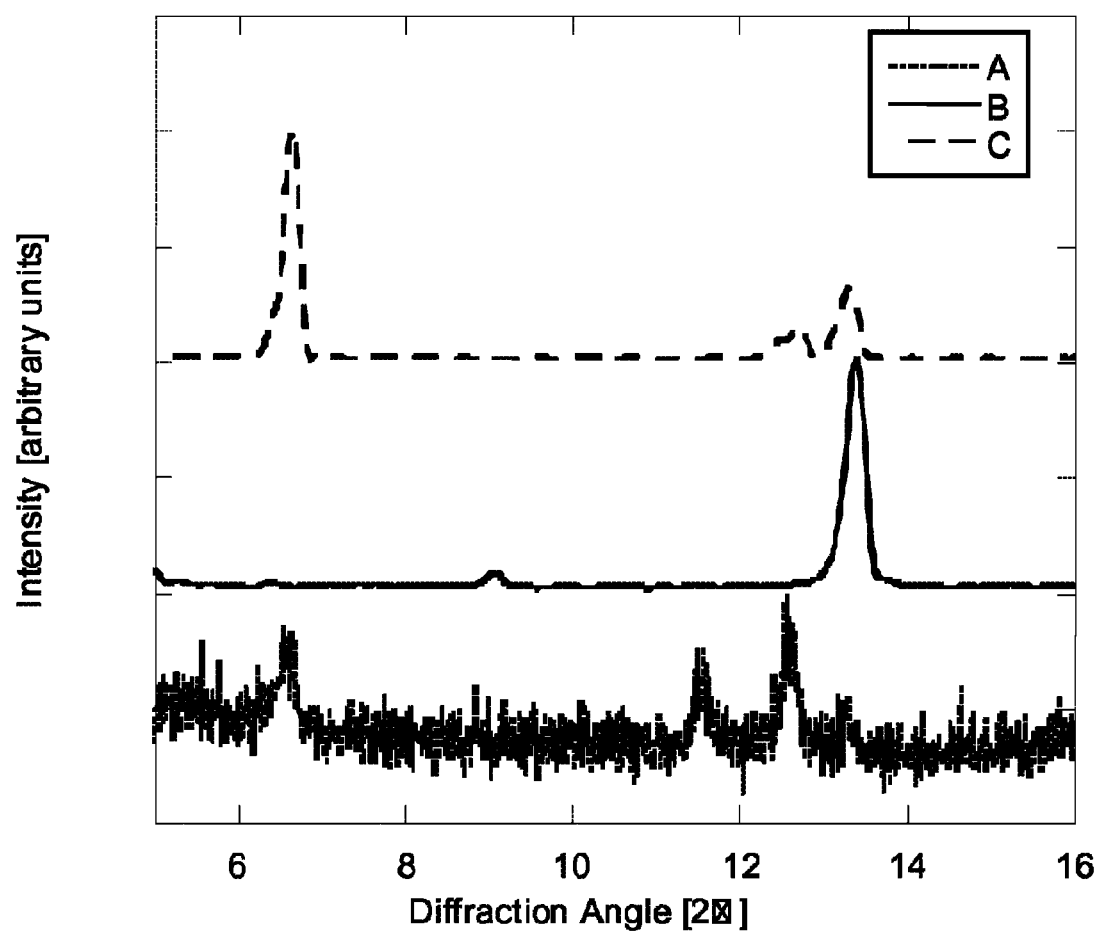

| WO | WO 2008/000042 | | 1/2008 |
|---|---|---|---|
| WO | WO 2008000042 A1 | * | 1/2008 |

OTHER PUBLICATIONS

Office Action in corresponding Colombia Patent Application No. 11-160596, dated Dec. 23, 2013; pp. 1-10.

Voltaren Package Insert Label and Instructions, Voltaren Gel, Novartis Consumer Health, Inc., pp. 1-23 (2009).

P. Gehanno et al., "Lowest Effective Single Dose of Diclofenac for Antipyretic and Analgesic Effects in Acute Febrile Sore Throat," Clin Drug Invest 2003; 23 (4) 263-271.

Jenkins and Seligman, "Analysis and recommendations for Agency action regarding non-steroidal anti-inflammatory drugs and cardiovascular risk," Center for Drug Evaluation and Research, pp. 1-19 (2005).

Liversidge & Conzentino, "Drug particle size reduction for decreasing gastric irritancy and enhancing absorption of naproxen in rats," International Journal of Pharmaceutics 125 (1995) 309-313.

Nicholas Moore, "Diclofenac Potassium 12.5mg Tablets for Mild to Moderate Pain and Fever, A Review of Its Pharmacology, Clinical Efficacy and Safety," Clin Drug Invest 2007; 27(3): 163-195.

Sonoda et al., "Improvement of Dissolution Property of Poorly Water-Soluble Drug by Novel Dry Coating Method Using Planetary Ball Mill,"Chem. Pharm. Bull 56(9) 1243-1247 (2008).

Vogt et al., "Cogrinding enhances the oral bioavailability of EMD 57033, a poorly water soluble drug, in dogs," European Journal of Pharmaceutics and Biopharmaceutics 68 (2008) 338-345.

Vogt et al., "Dissolution enhancement of fenofibrate by micronization, cogrinding and srpay-drying: Comparison with commercial preparations," European Journal of Pharmaceutics and Biopharmaceutics 68 (2008) 283-288.

B. Chuasuwan et al., "Biowaiver Monographs for Immediate Release Solid Oral Dosage Forms: Diclofenac Sodium and Diclofenac Potassium," Journal of Pharmaceutical Sciences, 98(4):1206-1219 (2009).

Notice of Paragraph IV Certification Regarding NDA 20-4592 Letter dated Nov. 24, 2014, pp. 1-42.

Detailed Statement of the Factual and Legal Bases Opinion that U.S. Pat. Nos. 8,999,387 and 9,017,721 are Invalid, Uneforceable and/or Not Infringed, dated May 7, 2015, pp. 1-80.

Dubin "Formulation Strategies for Poorly Soluable Drugs," Drug Delivery Tech 2006, 6(6):34-38.

Encyclopedia of Pharmaceutical Technology, vol. 5, Swarbrick and Boylan (eds)., 1991, p. 275.

Hanafy et al., "Pharmacokinetic evaluation of oral fenofibrate nanosuspensions and SLN in comparison to conventional suspensions of micronized drug," 59:419-426.

Hu et al., "Nanoparticle Engineering Processes for Enhancing the Dissolution Rates of Poorly Water Soluble Drugs," Drug Dev. & Industrial Pharmacy, 2004, 30(3):233-245.

Initial Invalidity Contentions of Defendants Lupin Limited and Lupin Pharmaceuticals, Inc., State of Delaware Civil Action No. 14-1515-SLR-SRF, dated Jul. 24, 2015, 91 pages.

Initial Invalidity Contentions of Defendants Lupin Limited and Lupin Pharmaceuticals, Inc., Exhibit A, Claim Chart for U.S. Pat. No. 8,679,544, State of Delaware Civil Action No. 14-1515-SLR-SRF, 21 pages.

Initial Invalidity Contentions of Defendants Lupin Limited and Lupin Pharmaceuticals, Inc., Exhibit B, Claim Chart for U.S. Pat. No. 8,999,387, State of Delaware Civil Action No. 14-1515-SLR-SRF, 15 pages.

Initial Invalidity Contentions of Defendants Lupin Limited and Lupin Pharmaceuticals, Inc., Exhibit C, Claim Chart for U.S. Pat. No. 9,017,721, State of Delaware Civil Action No. 14-1515-SLR-SRF, 14 pages.

Kesisoglou et al., "Nanosizing—Oral formulation development and biopharmaceutical evaluation," 2007, 59:631-644.

Kraml et al., "Gastrointestinal Absorption of Griseofulvin: II. Influence of Particle Size in Man," Antibiotics & Chemotherapy, APr. 1962. 12(4):239-242.

Lipinski, "Poor Aqueous Solubility—an Industry Wide Problem in Drug Discovery," Amer. Pharmaceutical Rev., 2002, 5(3):82-85.

Merisko-Liversidge et al., "Nanosizing: a formulation approach for poorly-water-soluble compounds," Euro. J. of Pharmaceutical Sci., 2003, 18:113-120.

Merisko-Liversidge and Liversidge, "Drug-Nanoparticles: Formulating Poorly Water-Soluble Compounds," Toxicologic Pathology, 2008, 36:43-48.

Mëller and Peters, "Nanosuspensions for the formulation of poorly soluble drugs I. Preparation by a size-reduction technique," International Journal of Pharmaceutics, 1998, 160:229-237.

Novartis Package Insert for Cataflam®, Voltaren®, and Voltaren®-XR, Novartis Pharmaceuticals Corporation, May 2000, 20 pages.

Rasenack et al., "Microcrystals for dissolution rate enhancement of poorly water-soluble drugs," International Journal of Pharmaceutics, 2003, 254:137-145.

Shaw and Carless, "The Effect of Particle Size on the Absorption of Digoxin," Euro. J. Clin. Pharmacol., 1974, 7:269-273.

Van Eerdenbrugh et al., "Screening Study of Surface Stabilization during the Production of Drug Nanocrystals." J. of Pharmaceutical Sci., Jun. 2009, 98(6):2091-2103.

Vergote et al., "In vivo evaluation of matrix pellets containing nanocrystalline ketoprofen," International Journal of Pharmaceutics, 2002, 240:79-84.

* cited by examiner

| Sample No. | Active material |  |  | Primary Matrix |  |  | Surfactant #1 |  |  | Surfactant #2 |  |  | Time (mins.) | Particle Size |  |  |  |  |  | Yield (%) | Variations |
|---|---|---|---|---|---|---|---|---|---|---|---|---|---|---|---|---|---|---|---|---|---|
|  | Name | Mass (g) | % w/w | % v/v | Name | Mass (g) | % w/w | Name | Mass (g) | % w/w | Name | Mass (g) | % w/w |  | D(0.5) μm | % <0.20 μm | % <0.30 μm | % < 0.5 μm | % < 1.0 μm | % < 2.0 μm |  |  |
| A | IND | 1.20 | 12 |  | LAC | 8.80 | 88 |  |  |  |  |  |  | 30 | 0.223 | 45 | 61 | 71 | 77 | 89 |  |  |
| B | IND | 1.20 | 12 |  | LAC | 8.70 | 87 | SPS | 0.1 | 1 |  |  |  | 30 | 0.215 | 47 | 64 | 84 | 83 | 93 |  |  |
| C | IND | 1.20 | 12 |  | LAC | 8.70 | 87 | SDS | 0.1 | 1 |  |  |  | 30 | 0.189 | 53 | 73 | 88 | 95 | 99 |  |  |
| D | IND | 1.20 | 12 |  | LAC | 8.70 | 87 | SOS | 0.1 | 1 |  |  |  | 30 | 0.203 | 49 | 69 | 84 | 92 | 97 |  |  |
| E | IND | 1.20 | 12 |  | LAC | 8.70 | 87 | B700 | 0.1 | 1 |  |  |  | 30 | 0.167 | 60 | 80 | 93 | 97 | 99 |  |  |
| F | IND | 1.20 | 12 |  | LAC | 8.70 | 87 | B76 | 0.1 | 1 |  |  |  | 30 | 0.192 | 52 | 72 | 89 | 96 | 99 |  |  |
| G | IND | 1.20 | 12 |  | LAC | 8.70 | 87 | SDC | 0.1 | 1 |  |  |  | 30 | 0.191 | 52 | 67 | 77 | 83 | 93 |  |  |
| H | IND | 1.20 | 12 |  | LAC | 8.70 | 87 | SNS | 0.1 | 1 |  |  |  | 30 | 0.225 | 44 | 63 | 79 | 88 | 96 |  |  |
| I | IND | 1.20 | 12 |  | LAC | 8.70 | 87 | LEC | 0.1 | 1 |  |  |  | 30 | 0.230 | 44 | 61 | 75 | 85 | 95 |  |  |
| J | IND | 0.5 | 10 |  | LAC | 4.50 | 90 |  |  |  |  |  |  | 20 | 0.237 | 44 | 57 | 65 | 73 | 85 |  |  |
| K | IND | 0.5 | 10 |  | LAC | 4.45 | 89 | P40S | 0.05 | 1 |  |  |  | 20 | 0.169 | 58 | 72 | 80 | 89 | 97 |  |  |
| L | IND | 0.5 | 10 |  | LAC | 4.45 | 89 | DS | 0.05 | 1 |  |  |  | 20 | 0.249 | 42 | 56 | 68 | 84 | 98 |  |  |
| M | IND | 0.5 | 10 |  | LAC | 4.45 | 89 | AS | 0.05 | 1 |  |  |  | 20 | 0.190 | 52 | 67 | 76 | 84 | 92 |  |  |
| N | IND | 1.0 | 20 |  | LAC | 3.95 | 79 | SDS | 0.05 | 1 |  |  |  | 30 | 0.435 | 24 | 38 | 53 | 67 | 83 |  |  |
| O | IND | 1.0 | 20 |  |  |  |  | SDS | 4.00 | 80 |  |  |  | 30 | 2.612 | 0 | 0 | 0 | 6 | 34 |  |  |
| P | IND | 4.95 | 99 |  |  |  |  |  |  |  |  |  |  | 30 | 1094 | 0 | 0 | 0 | 0 | 2 |  |  |
| Q | IND | 1.0 | 20 |  | LAC | 4.00 | 80 |  |  |  |  |  |  | 30 | 5.128 | 0 | 0 | 0 | 0 | 8 |  |  |
| R | DIC | 1.0 | 20 |  | LAC | 3.95 | 79 | SDS | 0.05 | 1 |  |  |  | 30 | 0.153 | 66 | 84 | 95 | 98 | 99 |  |  |
| S | DIC | 1.0 | 20 |  |  |  |  | SDS | 4.00 | 80 |  |  |  | 30 | 3.173 | 0 | 0 | 0 | 3 | 24 |  |  |

Figure 1A

| Sample No. | Active material Name | Mass (g) | % w/w | % v/v | Primary Matrix Name | Mass (g) | % w/w | Surfactant #1 Name | Mass (g) | % w/w | Surfactant #2 Name | Mass (g) | % w/w | Time (mins.) | D(0.5) μm | %<0.20 μm | %<0.30 μm | %<0.5 μm | %<1.0 μm | %<2.0 μm | Yield (%) | Variations |
|---|---|---|---|---|---|---|---|---|---|---|---|---|---|---|---|---|---|---|---|---|---|---|
| T | DIC | 4.95 | 99 | | | | | | | | | | | 30 | 117 | 0 | 0 | 0 | 1 | 4 | | |
| U | DIC | 1.00 | 20 | | LAC | 4.00 | 80 | SDS | 0.05 | 1 | | | | 30 | 0.178 | 56 | 74 | 86 | 92 | 97 | | |
| V | DIC | 2.00 | 20 | | MAN | 8.00 | 80 | | | | | | | 30 | 0.2 | 50 | 69 | 84 | 91 | 97 | | |
| W | DIC | 2.00 | 20 | | MAN | 7.90 | 79 | SDS | 0.1 | 1 | | | | 30 | 0.201 | 50 | 69 | 83 | 91 | 97 | | |
| X | DIC | 2.00 | 20 | | MAN | 7.90 | 79 | SOS | 0.1 | 1 | | | | 30 | 0.195 | 51 | 71 | 85 | 92 | 97 | | |
| Y | NAA | 1.75 | 35 | | LAC | 3.2 | 65 | | | | | | | 20 | 2.9 | 18 | 23 | 25 | 26 | 38 | | |
| Z | NAA | 1.75 | 35 | | LAC | 3.25 | 64 | P40S | 0.05 | 1 | | | | 20 | 0.373 | 33 | 45 | 56 | 70 | 87 | | |
| AA | NAA | 1.75 | 35 | | LAC | 3.25 | 64 | SDS | 0.05 | 1 | | | | 20 | 0.293 | 38 | 50 | 60 | 65 | 75 | | |
| AB | NAA | 4.0 | 40 | | LAC | 5.9 | 59 | P40S | 0.1 | 1 | | | | 120 | 0.285 | 37 | 52 | 66 | 75 | 82 | | |
| AC | NAA | 4.0 | 40 | | LAC | 6.0 | 60 | | | | | | | 120 | 6.1 | 0 | 0 | 0 | 0 | 8 | | |
| AD | NAA | 1.40 | 35 | | MAN | 2.60 | 65 | | | | | | | 20 | 0.171 | 58 | 73 | 82 | 86 | 88 | | |
| AE | NAA | 1.40 | 35 | | MAN | 2.52 | 63 | SDS | 0.08 | 2 | | | | 20 | 0.131 | 76 | 90 | 95 | 96 | 98 | | |
| AF | NAA | 1.2 | 30 | | MAN | 2.8 | 70 | | | | | | | 20 | 0.208 | 48 | 64 | 75 | 79 | 84 | | |
| AG | NAA | 1.2 | 30 | | MAN | 2.76 | 69.0 | SDS | 0 | 1.0 | | | | 20 | 0.173 | 58 | 75 | 86 | 91 | 96 | | |
| AH | NAA | 1.2 | 30.0 | | LAC | 2.8 | 70.0 | | | | | | | 20 | 0.396 | 33 | 44 | 53 | 58 | 70 | | |
| AI | NAA | 1.2 | 30.0 | | TCD | 2.8 | 70.0 | | | | | | | 20 | 3.1 | 18 | 24 | 27 | 27 | 37 | | |
| AJ | NAA | 1.2 | 30.0 | | CAC | 2.8 | 70.0 | | | | | | | 20 | 28 | 3 | 4 | 5 | 6 | 10 | | |
| AK | NAA | 1 | 25.0 | | LAA | 3 | 75.0 | | | | | | | 20 | 1.07 | 31 | 41 | 46 | 49 | 67 | | |
| AL | NAA | 1 | 25.0 | | XYL | 3 | 75.0 | | | | | | | 20 | 0.18 | 57 | 75 | 87 | 92 | 95 | | |

Figure 1B

| Sample No. | Active material Name | Active material Mass (g) | Active material % w/w | Active material % v/v | Primary Matrix Name | Primary Matrix Mass (g) | Primary Matrix % w/w | Surfactant #1 Name | Surfactant #1 Mass (g) | Surfactant #1 % w/w | Surfactant #2 Name | Surfactant #2 Mass (g) | Surfactant #2 % w/w | Time (mins.) | D(0.5) μm | % <0.20 μm | % <0.30 μm | % <0.5 μm | % <1.0 μm | % <2.0 μm | Yield (%) | Variations |
|---|---|---|---|---|---|---|---|---|---|---|---|---|---|---|---|---|---|---|---|---|---|---|
| AM | NAA | 1 | 25.0 | | MAA | 3 | 75.0 | | | | | | | 20 | 0.153 | 66 | 85 | 96 | 98 | 99 | | |
| AN | NAA | 1 | 25.0 | | TCD | 3 | 75.0 | | | | | | | 20 | 0.331 | 35 | 48 | 57 | 62 | 72 | | |
| AO | HAL | 1 | 10.0 | | LAC | 9 | 90.0 | | | | | | | 40 | 2.123 | 0 | 0 | 0 | 0 | 5 | | |
| AP | HAL | 1 | 10.0 | | LAC | 8.9 | 89.0 | LEC | 0.1 | 1.0 | | | | 40 | 0.135 | 74 | 90 | 97 | 98 | 99 | | |
| AQ | MET | 1 | 10.0 | | LAC | 9 | 90.0 | | | | | | | 40 | 4.727 | 0 | 0 | 0 | 0 | 4 | | |
| AR | MET | 1 | 10.0 | | LAC | 8.9 | 89.0 | SDS | 0.1 | 1.0 | | | | 40 | 0.129 | 80 | 93 | 96 | 97 | 98 | | |
| AS | TRI | 1 | 10.0 | | LAC | 9 | 90.0 | | | | | | | 40 | 2.622 | 0 | 0 | 0 | 0 | 25 | | |
| AT | TRI | 1 | 10.0 | | LAC | 8.9 | 89.0 | B700 | 0.1 | 1.0 | | | | 40 | 0.128 | 82 | 96 | 98 | 98 | 99 | | |
| AU | SUL | 1 | 10.0 | | LAC | 9 | 90.0 | | | | | | | 40 | 0.388 | 27 | 42 | 56 | 69 | 86 | | |
| AV | SUL | 1 | 10.0 | | LAC | 8.9 | 89.0 | SDS | 0.1 | 1.0 | | | | 40 | 0.455 | 6 | 26 | 55 | 78 | 96 | | |
| AW | MAN | 1 | 10.0 | | LAC | 9 | 90.0 | | | | | | | 40 | 0.198 | 50 | 71 | 88 | 97 | 97 | | |
| AX | MAN | 1 | 10.0 | | LAC | 8.9 | 89.0 | B700 | 0.1 | 1.0 | | | | 40 | 0.17 | 60 | 82 | 96 | 100 | 100 | | |
| AY | MAN | 1 | 10.0 | | LAC | 8.9 | 89.0 | SDS | 0.1 | 1.0 | | | | 40 | 0.171 | 60 | 82 | 97 | 100 | 100 | | |
| AZ | MAN | 1 | 10.0 | | LAC | 8.9 | 89.0 | LEC | 0.1 | 1.0 | | | | 40 | 0.181 | 56 | 78 | 95 | 100 | 100 | | |
| BA | MAN | 2 | 20.0 | | LAC | 7.9 | 79.0 | SDS | 0.1 | 1.0 | | | | 40 | 0.212 | 47 | 68 | 86 | 96 | 98 | | |
| BB | MAN | 3 | 30.0 | | LAC | 6.9 | 69.0 | SDS | 0.1 | 1.0 | | | | 40 | 0.258 | 36 | 58 | 81 | 94 | 97 | | |
| BC | MTX | 1.5 | 30.0 | | LAC | 3.5 | 69.0 | P407 | 0.1 | 1.0 | | | | 60 | 0.16 | 63 | 77 | 84 | 89 | 93 | | 2 |
| BD | MTX | 1.5 | 30.0 | | LAC | 3.5 | 70.0 | | | | | | | 60 | 0.28 | 40 | 52 | 59 | 59 | 71 | | 2 |
| BE | MTX | 2.5 | 50.0 | | LAC | 2.35 | 47.0 | SDS | 0.8 | 2.0 | P407 | 0.1 | 2 | 60 | 0.148 | 67 | 83 | 92 | 98 | 99 | | 2 |

Figure 1C

| Sample No. | Active material Name | Active material Mass (g) | Active material % w/w | Active material % v/v | Primary Matrix Name | Primary Matrix Mass (g) | Primary Matrix % w/w | Surfactant #1 Name | Surfactant #1 Mass (g) | Surfactant #1 % w/w | Surfactant #2 Name | Surfactant #2 Mass (g) | Surfactant #2 % w/w | Time (mins.) | D(0.5) μm | % <0.20 μm | % <0.30 μm | % < 0.5 μm | % < 1.0 μm | % < 2.0 μm | Yield (%) | Variations |
|---|---|---|---|---|---|---|---|---|---|---|---|---|---|---|---|---|---|---|---|---|---|---|
| BF | NAA | 1 | 25 | 30 | MAN | 3 | 75 | | | | | | | 20 | 0.181 | 55 | 74 | 87 | 94 | 97 | | |
| BG | NAA | 1 | 25 | 30 | MAN | 3 | 75 | | | | | | | 20 | 0.177 | 56 | 74 | 85 | 91 | 95 | | |
| BH | NAS | 1.25 | 25 | 30 | XYL | 3.75 | 75 | | | | | | | 20 | 0.311 | 37 | 49 | 59 | 64 | 75 | | |
| BI | NAS | 1.25 | 25 | 30 | TA | 3.75 | 75 | P40S | 0.1 | 1 | | | | 30 | 0.303 | 36 | 50 | 62 | 77 | 89 | | |
| BJ | DIC | 3 | 30 | 31 | TA | 6.9 | 69 | SDS | 0.1 | 1 | | | | 90 | 0.202 | 49 | 69 | 83 | 88 | 92 | 93 | 1 |
| BK | 2,4D | 1 | 20 | | LAC | 4 | 80 | | | | | | | 30 | 1.205 | 17 | 23 | 29 | 43 | 72 | 91 | 1 |
| BL | 2,4D | 1 | 20 | | LAC | 3.95 | 79 | SDA | 0.05 | 1 | | | | 30 | 0.473 | 20 | 33 | 52 | 75 | 82 | 93 | 1 |
| BM | 2,4D | 1 | 20 | | LAC | 3.95 | 79 | T3785 | 0.05 | 1 | | | | 30 | 0.414 | 24 | 38 | 57 | 78 | 94 | 93 | 1 |
| BN | 2,4D | 1 | 20 | | LAC | 3.95 | 79 | D920 | 0.05 | 1 | | | | 30 | 0.402 | 26 | 40 | 57 | 78 | 91 | | |
| BO | 2,4D | 1 | 20 | | LAC | 3.95 | 79 | SDS | 0.05 | 1 | | | | 30 | 0.276 | 36 | 54 | 74 | 92 | 96 | 92 | 1 |
| BP | 2,4D | 1 | 20 | | LAC | 3.95 | 79 | B700 | 0.05 | 1 | | | | 30 | 0.269 | 38 | 54 | 69 | 86 | 95 | 91 | 1 |
| BQ | 2,4D | 1 | 20 | | LAC | 3.95 | 79 | K1251 | 0.05 | 1 | | | | 30 | 0.252 | 41 | 56 | 71 | 89 | 96 | 94 | 1 |
| BR | 2,4D | 1 | 20 | | LAC | 3.95 | 79 | T305 | 0.05 | 1 | | | | 30 | 0.231 | 44 | 59 | 73 | 87 | 96 | 59 | 4 |
| BS | GLY | 1 | 20 | | LAC | 3.95 | 79 | T2700 | 0.05 | 1 | T2700 | 0.05 | 1 | 30 | 0.976 | 25 | 35 | 43 | 50 | 64 | 84 | 4 |
| BT | GLY | 1 | 20 | | LAC | 3.95 | 79 | B700 | 0.05 | 1 | K1251 | 0.05 | 1 | 30 | 1.449 | 21 | 27 | 33 | 42 | 57 | 81 | 4 |
| BU | GLY | 1 | 20 | | LAC | 3.9 | 78 | B700 | 0.05 | 1 | | | | 30 | 0.311 | 37 | 49 | 58 | 66 | 79 | 82 | 4 |
| BV | GLY | 1 | 20 | | LAC | 3.9 | 78 | B700 | 0.05 | 1 | | | | 30 | 1.085 | 26 | 34 | 41 | 49 | 66 | 86 | 4 |
| BW | GLY | 1 | 20 | | LAC | 3.9 | 78 | B700 | 0.05 | 1 | P188 | 0.05 | 1 | 30 | 1.48 | 8 | 11 | 16 | 33 | 62 | 79 | 4 |
| BX | GLY | 1 | 20 | | LAC | 3.9 | 78 | B700 | 0.05 | 1 | T2700 | 0.05 | 1 | 60 | 0.176 | 57 | 74 | 86 | 94 | 96 | | |

Figure 1D

| Sample No. | Active material Name | Active material Mass (g) | Active material % w/w | Active material % v/v | Primary Matrix Name | Primary Matrix Mass (g) | Primary Matrix % w/w | Surfactant #1 Name | Surfactant #1 Mass (g) | Surfactant #1 % w/w | Surfactant #2 Name | Surfactant #2 Mass (g) | Surfactant #2 % w/w | Time (mins.) | D(0.5) μm | % <0.20 μm | % <0.30 μm | % < 0.5 μm | % < 1.0 μm | % < 2.0 μm | Yield (%) | Variations |
|---|---|---|---|---|---|---|---|---|---|---|---|---|---|---|---|---|---|---|---|---|---|---|
| BY | GLY | 1 | 20 | | LAC | 3.9 | 78 | B700 | 0.05 | 1 | K1251 | 0.05 | 1 | 60 | 0.658 | 0 | 0 | 21 | 93 | 100 | 81 | 4 |
| BZ | GLY | 1 | 20 | | LAC | 3.9 | 78 | B700 | 0.05 | 1 | T2700 | 0.05 | 1 | 60 | 0.159 | 63 | 78 | 88 | 94 | 95 | 79 | 4 |
| CA | GLY | 1 | 20 | | LAC | 3.9 | 78 | B700 | 0.05 | 1 | K1251 | 0.05 | 1 | 60 | 0.297 | 34 | 50 | 70 | 95 | 100 | 81 | 4 |
| CB | MEL | 0.5 | 10 | | LAC | 4.4 | 88 | CEL | 0.1 | 2 | | 0 | 0 | 25 | 1.128 | 31 | 39 | 42 | 48 | 68 | 68 | 1 |
| CC | MEL | 0.5 | 10 | | LAC | 4.3 | 87 | P188 | 0.2 | 3 | BC | 0 | 1 | 25 | 0.27 | 38 | 53 | 59 | 62 | 81 | 73 | 1 |
| CD | MEL | 0.5 | 10 | | LAC | 4.3 | 87 | P188 | 0.2 | 3 | CEL | 0 | 1 | 25 | 0.278 | 40 | 52 | 58 | 62 | 76 | 74 | 1 |
| CE | MEL | 0.5 | 10 | | LAC | 4.3 | 87 | P188 | 0.2 | 3 | DS | 0 | 1 | 25 | 0.12 | 82 | 96 | 100 | 100 | 100 | 88 | 1 |
| CF | MEL | 0.5 | 10 | | LAC | 4.4 | 89 | P188 | 0.1 | 1 | K25 | 0 | 1 | 25 | 0.249 | 42 | 55 | 59 | 61 | 74 | 69 | 1 |
| CG | MEL | 0.25 | 5 | | MAN | 4.6 | 92 | P188 | 0.2 | 3 | LEC | 0.02 | 0.5 | 25 | 0.123 | 81 | 96 | 100 | 100 | 100 | 58 | 1 |
| CH | MEL | 0.5 | 10 | | LAC | 4.3 | 87 | P188 | 0.2 | 3 | LEC | 0.02 | 0.5 | 25 | 0.144 | 71 | 88 | 94 | 94 | 97 | 68 | 1 |
| CI | MEL | 0.5 | 10 | | LAC | 4.3 | 87 | P188 | 0.2 | 3 | SDC | | 0.5 | 25 | 0.184 | 54 | 70 | 79 | 81 | 87 | 63 | 1 |
| CJ | MEL | 0.5 | 10 | | LAC | 4.7 | 94 | P188 | 0.1 | 1 | T80 | 0 | 1 | 25 | 0.224 | 45 | 61 | 70 | 75 | 87 | 68 | 1 |
| CK | MEL | 0.25 | 5 | | LAC | 4.4 | 87 | P188 | 0.2 | 3 | | | | 25 | 0.158 | 63 | 81 | 90 | 90 | 93 | 48 | 1 |
| CL | MEL | 0.5 | 10 | | LAC | 4.6 | 92 | P188 | 0.2 | 3 | | | | 25 | 0.169 | 59 | 76 | 85 | 87 | 93 | 58 | 1 |
| CM | MEL | 0.25 | 5 | | LAC | 4.3 | 85 | P188 | 0.3 | 5 | | | | 25 | 0.221 | 46 | 60 | 68 | 69 | 75 | 68 | 1 |
| CN | MEL | 0.5 | 10 | | MAN | 4.6 | 88 | P188 | 0.2 | 3 | | | | 25 | 0.309 | 39 | 49 | 55 | 56 | 66 | 74 | 1 |
| CO | MEL | 0.5 | 9.5 | | MAN | 4.6 | 88 | P188 | 0.2 | 3 | | | | 25 | 0.251 | 43 | 55 | 61 | 62 | 68 | 55 | 1 |
| CP | MEL | 0.5 | 10 | | MAN | 4.5 | 89 | P3000 | 0.1 | 1 | | | | 25 | 1.343 | 29 | 36 | 39 | 43 | 63 | 61 | 1 |
| CQ | MEL | 0.5 | 10 | | MAN | 4.5 | 89 | SDC | 0.1 | 1 | | | | 25 | 1.699 | 25 | 31 | 32 | 37 | 56 | 77 | 1 |

Figure 1E

| Sample No. | Active material Name | Active material Mass (g) | Active material % w/w | Active material % v/v | Primary Matrix Name | Primary Matrix Mass (g) | Primary Matrix % w/w | Surfactant #1 Name | Surfactant #1 Mass (g) | Surfactant #1 % w/w | Surfactant #2 Name | Surfactant #2 Mass (g) | Surfactant #2 % w/w | Time (mins.) | D(0.5) µm | Particle Size % <0.20 µm | Particle Size % <0.30 µm | Particle Size % < 0.5 µm | Particle Size % < 1.0 µm | Particle Size % < 2.0 µm | Yield (%) | Variations |
|---|---|---|---|---|---|---|---|---|---|---|---|---|---|---|---|---|---|---|---|---|---|---|
| CR | MEL | 0.5 | 10 |  | LAC | 4.4 | 88 | T80 | 0.1 | 2 |  |  |  | 25 | 1.279 | 28 | 35 | 38 | 44 | 65 | 68 | 1 |
| CS | MAN | 2.5 | 50 | 45 | LAC | 2.35 | 47 | SDS | 0.15 | 3 |  |  |  | 15 | 0.318 | 31 | 48 | 65 | 80 | 84 |  | 5 |
| CT | MAN | 2.5 | 50 | 45 | LAC | 2.45 | 49 | P188 | 0.05 | 1 |  |  |  | 15 | 0.33 | 30 | 46 | 64 | 77 | 82 |  | 5 |
| CU | MAN | 2.5 | 50 | 45 | LAC | 2.45 | 49 | P40S | 0.05 | 1 |  |  |  | 15 | 0.333 | 30 | 46 | 63 | 75 | 80 |  | 5 |
| CV | MAN | 2.5 | 50 | 45 | LAC | 2.45 | 49 | B700 | 0.05 | 1 |  |  |  | 15 | 0.337 | 29 | 46 | 63 | 76 | 81 |  | 5 |
| CW | MAN | 2.5 | 50 | 45 | LAC | 2.45 | 49 | P407 | 0.05 | 1 |  |  |  | 15 | 0.342 | 28 | 45 | 63 | 76 | 82 |  | 5 |
| CX | MAN | 2.5 | 50 | 45 | LAC | 2.45 | 49 | T1221 | 0.05 | 1 |  |  |  | 15 | 0.411 | 24 | 40 | 56 | 69 | 75 |  | 5 |
| CY | MAN | 2.5 | 50 | 45 | LAC | 2.45 | 49 | DS | 0.05 | 1 |  |  |  | 15 | 0.462 | 22 | 37 | 52 | 65 | 71 |  | 5 |
| CZ | MAN | 2.5 | 50 | 45 | LAC | 2.45 | 49 | SDS | 0.05 | 1 |  |  |  | 15 | 1.369 | 1 | 6 | 20 | 43 | 56 |  | 5 |
| DA | MAN | 2.5 | 50 | 45 | LAC | 2.45 | 49 | SDA | 0.05 | 1 |  |  |  | 15 | 1.766 | 0 | 2 | 14 | 38 | 52 |  | 5 |
| DB | MAN | 2.5 | 50 | 45 | LAC | 2.45 | 49 | CEL | 0.05 | 1 |  |  |  | 15 | 1.86 | 0 | 2 | 14 | 37 | 51 |  | 5 |
| DC | MAN | 2.5 | 50 | 45 | LAC | 2.5 | 50 |  |  |  |  |  |  | 15 | 2.578 | 0 | 1 | 11 | 31 | 45 |  | 5 |
| DD | CEL | 0.5 | 10 |  | LAC | 4.3 | 86 | SDS | 0.1 | 2 | P40S | 0.1 | 2 | 15 | 0.134 | 76 | 88 | 91 | 91 | 93 | 88 | 1 |
| DE | CEL | 0.5 | 10 |  | LAC | 4.3 | 86 | SDS | 0.1 | 2 | P407 | 0.1 | 2 | 15 | 0.14 | 75 | 83 | 83 | 83 | 86 | 90 | 1 |
| DF | CEL | 0.5 | 10 |  | LAC | 4.3 | 86 | SDS | 0.1 | 2 | LEC | 0.15 | 3 | 15 | 0.181 | 55 | 70 | 79 | 83 | 89 | 90 | 1 |
| DG | CEL | 0.5 | 10 |  | LAC | 4.3 | 86 | SDS | 0.1 | 2 | B700 | 0.15 | 3 | 15 | 1.903 | 28 | 37 | 44 | 46 | 51 | 90 | 1 |
| DH | CEL | 0.5 | 10 |  | LAC | 4.5 | 90 |  |  |  |  |  |  | 15 | 5.296 | 8 | 11 | 13 | 13 | 16 | 85 | 1 |
| DI | CEL | 0.5 | 10 |  | LAC | 4.3 | 86 | SDS | 0.1 | 1 | P3000 | 0.15 | 3 | 15 | 0.397 | 33 | 45 | 53 | 59 | 71 | 88 | 1 |
| DJ | CEL | 0.5 | 10 |  | LAC | 4.4 | 88 | SDS | 0.1 | 1 | P8000 | 0.05 | 1 | 15 | 0.234 | 44 | 58 | 69 | 77 | 87 | 87 | 1 |

Figure 1F

| Sample No. | Active material Name | Active material Mass (g) | Active material % w/w | Active material % v/v | Primary Matrix Name | Primary Matrix Mass (g) | Primary Matrix % w/w | Surfactant #1 Name | Surfactant #1 Mass (g) | Surfactant #1 % w/w | Surfactant #2 Name | Surfactant #2 Mass (g) | Surfactant #2 % w/w | Time (mins.) | D(0.5) μm | Particle Size % <0.20 μm | Particle Size % <0.30 μm | Particle Size % < 0.5 μm | Particle Size % < 1.0 μm | Particle Size % < 2.0 μm | Yield (%) | Variations |
|---|---|---|---|---|---|---|---|---|---|---|---|---|---|---|---|---|---|---|---|---|---|---|
| DK | CEL | 0.5 | 10 | | LAC | 4.3 | 86 | DS | 0.1 | 2 | P40S | 0.1 | 2 | 15 | 0.319 | 35 | 48 | 61 | 69 | 74 | 88 | 1 |
| DL | CEL | 0.5 | 10 | | SOR | 4.5 | 90 | | | | | | | 15 | 16.031 | 0 | 0 | 0 | 0 | 0.8 | 46 | 1 |
| DM | CEL | 0.5 | 10 | | SOR | 4.45 | 89 | SDS | 0.1 | 1 | | | | 15 | 0.173 | 57 | 72 | 79 | 80 | 86 | 52 | 1 |
| DN | CYA | 0.5 | 10 | | LAC | 4.45 | 89 | SDS | 0.1 | 1 | | | | 20 | 0.159 | 65 | 84 | 95 | 100 | 100 | 79 | 5 |
| DO | CYA | 0.5 | 10 | | MAN | 4.45 | 89 | SDS | 0.1 | 1 | | | | 20 | 0.194 | 52 | 68 | 79 | 84 | 84 | 87 | 5 |
| DP | PRO | 0.5 | 10 | | LAC | 4.45 | 89 | SDS | 0.1 | 1 | | | | 20 | 0.229 | 43 | 63 | 83 | 97 | 98 | 87 | 5 |
| DQ | PRO | 0.5 | 10 | | MAN | 4.45 | 89 | SDS | 0.1 | 1 | | | | 20 | 0.553 | 15 | 27 | 45 | 77 | 94 | 89 | 5 |
| DR | PRO | 0.5 | 10 | | LAC | 4.45 | 89 | C40 | 0.1 | 1 | | | | 20 | 0.546 | 10 | 23 | 45 | 76 | 89 | 72 | 5 |
| DS | SAL | 0.51 | 10 | | LAC | 4.5 | 89.5 | LEC | 0.05 | 1 | | | | 20 | 0.128 | 84 | 98 | 100 | 100 | 100 | | 6 |
| DT | SAL | 0.51 | 10 | | LAC | 4.5 | 89.5 | LEC | 0.05 | 1 | | | | 20 | 0.42 | 31 | 42 | 53 | 57 | 57 | | 6 |
| DU | CIP | 0.76 | 15 | | MAL | 4.1 | 83 | T80 | 0.05 | 1 | DS | | | 20 | 0.22 | 40 | 74 | 85 | 85 | 92 | 96 | 6 |
| DV | CIP | 0.76 | 15 | | LAC | 4.2 | 85 | | | | | | | 20 | 25.909 | 1 | 2 | 3.1 | 4.8 | 7 | 89 | 6 |
| DW | CIP | 0.76 | 15 | | MAL | 4.3 | 85 | T80 | 0.06 | 1 | | | | 20 | 0.238 | 43 | 56 | 58 | 58 | 61 | 93 | 6 |
| DX | CIP | 0.75 | 15 | | LAA | 4.3 | 85 | SOL | 0.05 | 1 | | | | 20 | 0.205 | 49 | 62 | 65 | 65 | 71 | 97 | 6 |
| DY | CIP | 0.75 | 15 | | LAA | 4.2 | 84 | CEL | 0.06 | 1 | | | | 20 | 0.14 | 75 | 91 | 94 | 94 | 96 | 96 | 6 |
| DZ | CIP | 0.75 | 15 | | LAA | 4.2 | 84 | | | | | | | 20 | 0.237 | 35 | 66 | 78 | 78 | 84 | 97 | 6 |
| EA | CIP | 0.75 | 15 | | LAA | 4.2 | 84 | DS | 0.05 | 1 | | | | 20 | 0.23 | 37 | 69 | 81 | 81 | 87 | 87 | 6 |
| EB | CIP | 0.75 | 15 | | LAA | 4.2 | 84 | | | | | | | 20 | 0.216 | 42 | 74 | 83 | 83 | 91 | 96 | 6 |
| EC | CIP | 0.75 | 15 | | LAA | 4.2 | 84 | P8000 | 0.05 | 1 | | | | 20 | 0.243 | 33 | 64 | 75 | 75 | 82 | 97 | 6 |

Figure 1G

| Sample No. | Active material Name | Active material Mass (g) | Active material % w/w | % v/v | Primary Matrix Name | Primary Matrix Mass (g) | Primary Matrix % w/w | Surfactant #1 Name | Surfactant #1 Mass (g) | Surfactant #1 % w/w | Time (mins.) | D(0.5) μm | % <0.20 μm | % <0.30 μm | % <0.5 μm | % <1.0 μm | % <2.0 μm | Yield (%) | Variations |
|---|---|---|---|---|---|---|---|---|---|---|---|---|---|---|---|---|---|---|---|
| A | IND | 1.20 | 12 |  | LAC | 8.80 | 88 |  |  |  | 30 | 0.753 | 25 | 34 | 44 | 55 | 70 |  |  |
| B | IND | 1.20 | 12 |  | LAC | 8.70 | 87 | SDS | 0.1 | 1 | 30 | 0.677 | 14 | 26 | 41 | 65 | 91 |  |  |
| C | IND | 1.20 | 12 |  | LAC | 8.70 | 87 | B700 | 0.1 | 1 | 30 | 0.621 | 13 | 25 | 43 | 68 | 91 |  |  |
| D | MEL | 1.2 | 20.0 |  | MAN | 4.62 | 77 | SDS | 0.18 | 3.0 | 10 | 0.277 | 37 | 53 | 66 | 74 | 86 | 83 |  |
| E | MEL | 1.2 | 20.0 |  | MAN | 4.8 | 80 |  |  |  | 15 | 2.493 | 10 | 12 | 12 | 15 | 39 | 33 |  |
| F | DIC | 3 | 30 | 30 | MAN | 6.7 | 67 | SDS | 0.3 | 3 | 90 | 0.157 | 63 | 79 | 86 | 88 | 93 |  |  |

Figure 2A

| Sample No. | Active material Name | Active material Mass (g) | Active material % w/w | Primary Matrix Name | Primary Matrix Mass (g) | Primary Matrix % w/w | 2nd Matrix Name | 2nd Matrix Mass (g) | 2nd Matrix % w/w | Time (mins.) | D(0.5) μm | % <0.20 μm | % <0.30 μm | % <0.5 μm | % <1.0 μm | % <2.0 μm | Yield (%) | Variations |
|---|---|---|---|---|---|---|---|---|---|---|---|---|---|---|---|---|---|---|
| A | NAA | 1.2 | 30.0 | LAC | 2 | 50.0 | TCD | 0.8 | 20.0 | 20 | 0.188 | 48 | 64 | 75 | 81 | 92 |  |  |
| B | NAA | 1.2 | 30.0 | LAC | 2 | 50.0 | CAC | 0.8 | 20.0 | 20 | 0.213 | 47 | 63 | 76 | 84 | 91 |  |  |
| C | NAA | 1 | 25.0 | LAA | 2.2 | 55.0 | XYL | 0.8 | 20.0 | 20 | 0.2 | 50 | 65 | 75 | 79 | 89 |  |  |
| D | NAA | 1 | 25.0 | LAA | 2.2 | 55.0 | MAA | 0.8 | 20.0 | 20 | 0.223 | 46 | 60 | 70 | 76 | 87 |  |  |
| E | NAA | 1 | 25.0 | LAA | 2.2 | 55.0 | TCD | 0.8 | 20.0 | 20 | 0.215 | 47 | 62 | 70 | 73 | 83 |  |  |

Figure 3A

Figure 4A

| Sample No. | Active material Name | Mass (g) | % w/w | % v/v | Primary Matrix Name | Mass (g) | % w/w | Surfactant #1 Name | Mass (g) | % w/w | 2nd Matrix Name | Mass (g) | % w/w | Time (mins.) | D(0.5) μm | % <0.20 μm | % <0.30 μm | % < 0.5 μm | % < 1.0 μm | % < 2.0 μm | Yield (%) | Variations |
|---|---|---|---|---|---|---|---|---|---|---|---|---|---|---|---|---|---|---|---|---|---|---|
| A | MEL | 20 | 20.0 |  | LAC | 77 | 77.0 | SDS | 3 | 3.0 |  |  |  | 15 | 0.24 | 39 | 64 | 87 | 97 | 100 | 90 |  |
| B | MEL | 20 | 20.0 |  | LAC | 80 | 80.0 |  |  |  |  |  |  | 15 | 0.166 | 59 | 74 | 82 | 87 | 90 | 0.7 |  |
| C | IND | 13 | 13.0 |  | LAC | 87 | 87.0 |  |  |  |  |  |  | 30 | 3.255 | 0 | 0 | 0 | 4 | 27 | 1 |  |
| D | IND | 13 | 13.0 |  | LAC | 65.5 | 65.5 | SDS | 1 | 1.0 | TA | 22 | 21.5 | 30 | 0.272 | 34 | 55 | 76 | 87 | 93 | 0 |  |
| E | IND | 13 | 13.0 |  | LAC | 86 | 86.0 |  |  |  |  |  |  | 30 | 0.836 | 22 | 31 | 39 | 56 | 83 | 76 |  |
| F | IND | 13 | 13.0 |  | LAC | 64.5 | 64.5 | SDS | 1 | 1.0 | TA | 22 | 21.5 | 30 | 0.629 | 15 | 28 | 43 | 67 | 91 |  |  |
| G | MEL | 25 |  | 25 | LAC | 72 | 72 | SDS | 3 | 3 |  |  |  | 15 | 0.283 | 33 | 53 | 73 | 84 | 92 | 85 |  |

Figure 5A

| Sample No. | Active material Name | Mass (g) | % w/w | Primary Matrix Name | Mass (g) | % w/w | Surfactant #1 Name | Mass (g) | % w/w | Surfactant #2 Name | Mass (g) | % w/w | Time (mins.) | D(0.5) μm | % <0.20 μm | % <0.30 μm | % < 0.5 μm | % < 1.0 μm | % < 2.0 μm | Yield (%) | Variations |
|---|---|---|---|---|---|---|---|---|---|---|---|---|---|---|---|---|---|---|---|---|---|
| A | NAA | 17.5 | 35.0 | MAN | 32 | 64.0 | SDS | 0.5 | 1.0 |  |  |  | 80 | 0.249 | 42 | 56 | 64 | 67 | 74 |  |  |
| B | NAA | 17.5 | 35.0 | MAN | 31.5 | 63.0 | SDS | 0.5 | 1.0 | P40S | 0.5 | 1 | 80 | 0.261 | 39 | 55 | 67 | 77 | 88 |  |  |
| C | NAA | 17.5 | 35.0 | MAN | 31.5 | 63.0 | SDS | 0.5 | 1.0 | P3000 | 0.5 | 1 | 80 | 0.188 | 53 | 70 | 81 | 88 | 95 |  |  |
| D | IND | 6 | 12.0 | LAC | 43.5 | 87.0 | SDS | 0.5 | 1.0 |  |  |  | 40 | 0.231 | 43 | 61 | 78 | 91 | 97 |  |  |
| E | IND | 6 | 12.0 | LAC | 43 | 86.0 | SDS | 0.5 | 1.0 | P407 | 0.5 | 1 | 40 | 0.152 | 66 | 85 | 95 | 97 | 98 |  |  |
| F | IND | 6 | 12.0 | LAC | 43 | 86.0 | SDS | 0.5 | 1.0 | P40S | 0.5 | 1 | 40 | 0.155 | 65 | 85 | 96 | 98 | 98 |  |  |

| Sample No. | | A | B | C | D | E | F | G | H | I | J | K | L | M | N | O | P | Q | R |
|---|---|---|---|---|---|---|---|---|---|---|---|---|---|---|---|---|---|---|---|
| Active material | Name | NAA | NAA | NAA | NAA | DIC | DIC | NAA | 2,4D | 2,4D | 2,4D | 2,4D | 2,4D | 2,4D | 2,4D | GLY | GLY | GLY | GLY |
| | Mass (g) | 70 | 70 | 60 | 60 | 52.5 | 52.5 | 60 | 40 | 40 | 40 | 40 | 40 | 60 | 60 | 40 | 40 | 60 | 60 |
| | % w/w | 35 | 35 | 30.0 | 30.3 | 15.0 | 13.0 | 30 | 20 | 20 | 20 | 20 | 20 | 20 | 20 | 20 | 20 | 20 | 20 |
| | % v/v | | | | | | | 35 | | | | | | | | | | | |
| Primary Matrix | Name | LAC | MAN | MAN | MAN | LAC | LAC | LAC | LAC | LAC | LAC | LAC | LAC | LAC | LAC | LAC | LAC | LAC | LAC |
| | Mass (g) | 128 | 128 | 138 | 138 | 294 | 224 | 138 | 160 | 158 | 158 | 158 | 234 | 234 | 234 | 158 | 156 | 234 | 234 |
| | % w/w | 64 | 64 | 69.0 | 69.7 | 84.0 | 66.0 | 69 | 80 | 79 | 79 | 79 | 78 | 78 | 78 | 79 | 78 | 78 | 78 |
| Surfactant #1 | Name | SDS | SDS | SDS | | SDS | SDS | SDS | | SDA | K1251 | D920 | SDA | D920 | K1251 | B700 | B700 | B700 | B700 |
| | Mass (g) | 2 | 2 | 2 | | 3.5 | 3.5 | 2 | | 2 | 2 | 2 | 3 | 4 | 3 | 2 | 2 | 3 | 3 |
| | % w/w | 1 | 1 | 1 | | 1.0 | 1.0 | 1 | | 1 | 1 | 1 | 1 | 1 | 1 | 1 | 1 | 1 | 1 |
| Surfactant #2 | Name | | | | | | | | | | | PVP | PVP | PVP | | T2700 | T2700 | T2700 | T2700 |
| | Mass (g) | | | | | | | | | | | 3 | 3 | 3 | | 2 | 2 | 3 | 3 |
| | % w/w | | | | | | | | | | | 1 | 1 | 1 | | 1 | 1 | 1 | 1 |
| 2nd Matrix | Name | | | | | TA | | | | | | | | | | | | | |
| | Mass (g) | | | | | 70 | | | | | | | | | | | | | |
| | % w/w | | | | | 20 | | | | | | | | | | | | | |
| Time (mins.) | | 60 | 50 | 50 | 50 | 40 | 40 | 40 | 30 | 30 | 30 | 30 | 30 | 40 | 40 | 90 | 45 | 30 | 50 |
| Particle Size | D(0.5) µm | 0.345 | 0.73 | 0.181 | 0.319 | 0.16 | 0.16 | 0.232 | 0.212 | 0.189 | 0.2 | 0.204 | 0.281 | 0.183 | 0.208 | 0.297 | 0.188 | 4.798 | 0.204 |
| | % <0.20 µm | 35 | 31 | 55 | 35 | 64 | 63 | 44 | 47 | 53 | 50 | 49 | 30 | 55 | 48 | 38 | 53 | 0 | 49 |
| | % <0.30 µm | 47 | 41 | 73 | 48 | 84 | 83 | 59 | 69 | 72 | 71 | 69 | 54 | 75 | 68 | 50 | 71 | 0 | 66 |
| | % < 0.5 µm | 56 | 48 | 86 | 59 | 97 | 95 | 70 | 90 | 87 | 89 | 86 | 82 | 91 | 88 | 61 | 85 | 0 | 79 |
| | % < 1.0 µm | 61 | 51 | 92 | 64 | 99 | 98 | 78 | 100 | 95 | 97 | 94 | 96 | 98 | 99 | 74 | 93 | 0.2 | 89 |
| | % < 2.0 µm | 73 | 58 | 96 | 75 | 99 | 99 | 90 | 100 | 97 | 97 | 96 | 98 | 100 | 98 | 87 | 96 | 9.9 | 94 |
| | No. Ave. nm | | | | | | | | | | | | | | | | | | |
| Yield (%) | | 98 | | 92 | 23 | 64 | 87 | 79 | 95 | 97 | 97 | 94 | 93 | 90 | 92 | 18 | 79 | | |
| Variations | | O | C | C | C | E | E | E | | | | | | | | D | D | D | |

Figure 6A

| Sample No. | Active material | | | | Primary Matrix | | | Surfactant #1 | | | Surfactant #2 | | | 2nd | | | Time (mins.) | Particle Size | | | | | | | Yield (%) | Variations |
|---|---|---|---|---|---|---|---|---|---|---|---|---|---|---|---|---|---|---|---|---|---|---|---|---|---|---|
| | Name | Mass (g) | % w/w | % v/v | Name | Mass (g) | % w/w | Name | Mass (g) | % w/w | Name | Mass (g) | % w/w | Name | Mass (g) | % w/w | | D(0.5) μm | % <0.20 μm | % <0.30 μm | % < 0.5 μm | % < 1.0 μm | % < 2.0 μm | No. Ave. nm | | |
| S | GLY | 60 | 20 | | LAC | 234 | 78 | B700 | 3 | 1 | T2700 | 3 | 1 | | | | 70 | 0.17 | 58 | 75 | 88 | 95 | 97 | | 94.7 | D |
| T | MEL | 35 | 10 | | LAC | 311.5 | 89 | LEC | 3.5 | 1 | | | | | | | 40 | 0.127 | 80 | 94 | 98 | 98 | 99 | | 81 | |
| U | MEL | 35 | 10 | | MAN | 311.5 | 89 | LEC | 3.5 | 1 | | | | | | | 20 | 0.199 | 50 | 67 | 76 | 82 | 91 | | 59 | 1 |
| V | MEL | 35 | 10 | | MAN | 309.8 | 89 | P188 | 3.5 | 1 | DS | 1.77 | 0.5 | | | | 20 | 0.13 | 77 | 94 | 100 | 100 | 100 | | 90 | 1 |
| W | MEL | 17.5 | 5 | | MAN | 323.8 | 93 | P188 | 7 | 2 | LEC | 1.75 | 0.5 | | | | 25 | 0.124 | 80 | 96 | 100 | 100 | 100 | | 67 | 1 |
| X | MEL | 17.5 | 5 | | LAC | 320.3 | 92 | P188 | 10.5 | 3 | LEC | 1.75 | 0.5 | | | | 40 | 0.129 | 78 | 94 | 99 | 99 | 99 | | 94 | 1 |
| Y | MEL | 17.5 | 5 | | MAN | 320.3 | 92 | P188 | 10.5 | 3 | LEC | 1.75 | 0.5 | | | | 25 | 0.14 | 72 | 88 | 93 | 94 | 98 | | 97 | 1 |
| Z | MEL | 35 | 10 | | LAC | 302.8 | 87 | P188 | 10.5 | 3 | | | | | | | 30 | 0.168 | 59 | 75 | 83 | 87 | 94 | | 52 | 1 |
| AA | MEL | 35 | 10 | | LAC | 311.5 | 89 | P188 | 3.5 | 1 | | | | | | | 40 | 0.118 | 87 | 99 | 100 | 100 | 100 | | 87 | 1 |
| AB | MEL | 35 | 10 | | MAN | 311.5 | 89 | P188 | 3.5 | 1 | | | | | | | 30 | 0.164 | 60 | 77 | 87 | 93 | 97 | | 32 | 1 |
| AC | MEL | 35 | 10 | | MAN | 315.0 | 90 | | | | | | | | | | 20 | 0.143 | 71 | 89 | 95 | 96 | 98 | | 79 | 1 |
| AD | MEL | 35 | 10 | | MAN | 315.0 | 90 | | | | | | | | | | 25 | 0.26 | 39 | 55 | 66 | 73 | 85 | | 56 | 1 |
| AE | CRM | 60 | 20 | | LAC | 138 | 69 | LEC | 1 | 2 | | | | | | | 60 | 0.152 | 64 | 78 | 84 | 87 | 89 | | 79 | 7 |
| AF | CIL | 30 | 10 | | LAC | 267 | 89 | SDS | 3 | 1 | | | | | | | 20 | 0.162 | 64 | 86 | 99 | 100 | 100 | | 84 | 5,D |
| AG | PRO | 30 | 10 | | LAC | 267 | 89 | SDS | 3 | 1 | | | | | | | 30 | 0.62 | 12 | 24 | 42 | 67 | 89 | | 74 | 5,D |
| AH | PRO | 30 | 10 | | LAC | 270 | 90 | T80 | 2.00 | | | | | | | | 30 | 0.91 | 9 | 18 | 33 | 52 | 61 | | 66 | 5,D |
| AI | CIP | 30.0 | 15 | | LAA | 168.0 | 84 | | | | | | | | | | 20 | 0.139 | 76 | 91 | 94 | 94 | 95 | 88 | 94 | E |
| AJ | CIP | 30.1 | 15 | | LAA | 170.0 | 85 | | | | | | | | | | 20 | 0.171 | 60 | 75 | 79 | 79 | 82 | | 36.7 | E |
| AK | CIP | 30.0 | 15 | | LAA | 168.0 | 84 | CEL | 2.00 | 1 | | | | | | | 20 | 0.277 | 41 | 51 | 54 | 54 | 56 | | 72 | E |

Figure 6B

| Sample No. | Active material Name | Active material Mass (g) | Active material % w/w | Active material % v/v | Primary Matrix Name | Primary Matrix Mass (g) | Primary Matrix % w/w | Surfactant #1 Name | Surfactant #1 Mass (g) | Surfactant #1 % w/w | Surfactant #2 Name | Surfactant #2 Mass (g) | Surfactant #2 % w/w | 2nd Name | 2nd Mass (g) | 2nd % w/w | Time (mins.) | D(0.5) μm | % <0.20 μm | % <0.30 μm | % < 0.5 μm | % < 1.0 μm | % < 2.0 μm | No. Ave. nm | Yield (%) | Variations |
|---|---|---|---|---|---|---|---|---|---|---|---|---|---|---|---|---|---|---|---|---|---|---|---|---|---|---|
| AL | GLY | 60.0 | 20 | | LAC | 240.0 | 80 | | | | | | | | | | 70 | 50.4 | 0 | 0 | 0 | 0.9 | 4.4 | 1282 | 26 | 3,P |
| AM | CEL | 20.0 | 10 | | LAC | 176.1 | 88 | SDS | 2.00 | 1 | P40S | 2 | 1 | | | | 10 | 0.205 | 49 | 66 | 79 | 86 | 92 | 81 | 86 | 1,D |
| AN | CEL | 20.0 | 10 | | LAC | 180.1 | 90 | | | | | | | | | | 10 | 4.775 | 0 | 0 | 0 | 0 | 6.4 | 2560 | 57 | 1,D |
| AO | CEL | 20.0 | 10 | | LAC | 176.0 | 88 | SDS | 2.00 | 1 | P8000 | 2 | 1 | | | | 10 | 0.353 | 34 | 46 | 56 | 64 | 77 | 80 | 86 | 1,D |
| AP | MAN | 150.1 | 50 | 45 | LAC | 147.1 | 49 | T3785 | 3.00 | 3 | | | | | | | 5 | 0.22 | 46 | 60 | 72 | 84 | 87 | 89 | 90 | 8,D |
| AQ | MAN | 150.1 | 50 | 45 | LAC | 150.0 | 50 | | | | | | | | | | 5 | 0.292 | 35 | 51 | 67 | 81 | 85 | 109 | 56 | 8,D |
| AR | MAN | 150.0 | 50 | 45 | LAC | 147.0 | 49 | DS | 3.02 | 3 | | | | | | | 5 | 0.274 | 38 | 53 | 67 | 80 | 84 | | 76 | 8,D |
| AS | NAA | 105.1 | 35 | 39 | MAN | 195.0 | 65 | | | | | | | | | | 80 | 0.189 | 53 | 70 | 82 | 87 | 91 | 80 | 81 | |
| AT | NAA | 105.0 | 35 | | MAN | 180.1 | 60 | MCC | 15.00 | 5 | | | | | | | 80 | 0.261 | 40 | 54 | 65 | 69 | 75 | 81 | 66 | D |
| AU | NAA | 105.0 | 35 | | MAN | 180.0 | 60 | PML | 15.10 | 5 | | | | | | | 80 | 0.243 | 42 | 58 | 69 | 76 | 85 | 83 | 51 | D |

Figure 6C

| Sample No. | Active material Name | Active material Mass (g) | Active material % w/w | Active material % v/v | Primary Matrix Name | Primary Matrix Mass (g) | Primary Matrix % w/w | Surfactant #1 Name | Surfactant #1 Mass (g) | Surfactant #1 % w/w | Surfactant #2 Name | Surfactant #2 Mass (g) | Surfactant #2 % w/w | 2nd Matrix Name | 2nd Matrix Mass (g) | 2nd Matrix % w/w | Disintegrant Name | Disintegrant Mass (g) | Disintegrant % w/w | Time (mins.) | D(0.5) μm | % <0.20 μm | % <0.30 μm | % <0.5 μm | % <1.0 μm | % <2.0 μm | Yield (%) | Variations |
|---|---|---|---|---|---|---|---|---|---|---|---|---|---|---|---|---|---|---|---|---|---|---|---|---|---|---|---|---|
| A | MTX | 1.5 | 30.0 | | LAC | 3.5 | 69.0 | P407 | 0.1 | 1.0 | | | | | | | | | | 60 | 0.16 | 63 | 77 | 84 | 89 | 93 | | 2 |
| B | MTX | 1.5 | 30.0 | | LAC | 3.5 | 70.0 | | | | | | | | | | | | | 60 | 0.28 | 40 | 52 | 59 | 59 | 71 | | 2 |
| C | MTX | 17.2 | 43.0 | | LAC | 22 | 56.0 | SDS | 0.4 | 1.0 | | | | | | | | | | 60 | 0.142 | 70 | 83 | 88 | 91 | 94 | | 2 |
| D | MTX | 20 | 50.0 | | LAC | 10.4 | 26.0 | SDS | 0.8 | 2.0 | P407 | 0.8 | 2 | | | | | | | 60 | 0.137 | 73 | 89 | 95 | 100 | 100 | | 9 |
| E | MTX | 2.5 | 50.0 | | LAC | 2.35 | 47.0 | SDS | 0.8 | 2.0 | P407 | 0.1 | 2 | SB | 8 | 20.0 | | | | 60 | 0.148 | 67 | 83 | 92 | 98 | 99 | | 2 |
| F | MTX | 17.2 | 43.0 | | MAN | 22.4 | 56.0 | SDS | 0.4 | 1.0 | | | | | | | | | | 60 | 0.254 | 42 | 55 | 64 | 67 | 72 | | 2 |
| G | MTX | 1 | 20 | | LAC | 4 | 80 | | | | | | | | | | | | | 60 | 13.45 | 0 | 0 | 0 | 0 | 0 | | 2 |
| H | MTX | 1 | 20 | | LAC | 3.9 | 78 | SDS | 0.05 | 1 | P407 | 0.05 | 1 | PVP | 0.05 | 1 | PRI | 0.25 | 5 | 60 | 0.13 | 76 | 91 | 96 | 98 | 98 | 92 | 2 |
| I | MTX | 1.25 | 25 | | LAC | 2.85 | 68 | SDS | 0.05 | 1 | P407 | 0.05 | 1 | | | | | | | 50 | 0.201 | 50 | 67 | 80 | 84 | 84 | 97 | 2 |
| J | MTX | 60 | 30 | 33 | LAC | 137 | 67 | SDS | 3 | 1.5 | P407 | 3 | 1.5 | | | | | | | 5 | 3.943 | 20 | 27 | 30 | 31 | 38 | 85 | 2 |
| K | MTX | 60 | 30 | 33 | LAC | 137 | 67 | SDS | 3 | 1.5 | P407 | 3 | 1.5 | | | | | | | 10 | 0.223 | 46 | 61 | 72 | 77 | 83 | | 2 |
| L | MTX | 60 | 30 | 33 | LAC | 137 | 67 | SDS | 3 | 1.5 | P407 | 3 | 1.5 | | | | | | | 16 | 0.153 | 64 | 79 | 86 | 93 | 96 | | 2 |
| M | MTX | 60 | 30 | 33 | LAC | 137 | 67 | | | | PVP | 1.61 | 1 | | | | | | | 21 | 0.142 | 67 | 85 | 92 | 95 | 96 | | 2 |
| N | 7M | 151 | 94 | | | | | | | | | | | | | | | | | | | | | | | | 97 | 2 |
| O | MTX | 60 | 30 | 33 | LAC | 137 | 67 | SDS | 3 | 1.5 | P407 | 3 | 1.5 | | | | PRI | 8.04 | 5 | 20 | 0.8 | 32 | 42 | 48 | 51 | 63 | 70 | 2,E |

Figure 7A

| Sample No. | Active material Name | Mass (g) | % w/w | % v/v | Primary Matrix Name | Mass (g) | % w/w | Surfactant #1 Name | Mass (g) | % w/w | Surfactant #2 Name | Mass (g) | % w/w | 2nd Matrix Name | Mass (g) | % w/w | Time (mins.) | D(0.5) μm | % <0.20 μm | % <0.30 μm | % < 0.5 μm | % < 1.0 μm | % > 2.0 μm | Yield (%) | Variations |
|---|---|---|---|---|---|---|---|---|---|---|---|---|---|---|---|---|---|---|---|---|---|---|---|---|---|
| A | MEL | 48 | 10 |  | LAC | 417.6 | 87 | SDS | 14.4 | 3 |  |  |  |  |  |  | 3 | 0.15 | 66 | 83 | 90 | 91 | 94 | 97 | 1 |
| B | MEL | 24 | 5 |  | LAC | 439.2 | 91.5 | P188 | 14.4 | 3 | LEC | 2.4 | 0.5 |  |  |  | 8 | 0.159 | 63 | 81 | 91 | 94 | 98 | 97 | 1 |
| C | MEL | 24 | 5 |  | MAN | 439.2 | 91.5 | P188 | 14.4 | 3 | LEC | 2.4 | 0.5 |  |  |  | 8 | 0.144 | 70 | 88 | 94 | 95 | 98 | 97 | 1 |
| D | IND | 62.4 | 13 |  | LAC | 312 | 65 | SDS | 4.8 | 1 |  |  |  | TA | 100.8 | 21 | 4 | 0.197 | 51 | 68 | 81 | 88 | 94 | 92 |  |
| E | IND | 62.4 | 13 |  | LAC | 312 | 66 |  |  |  |  |  |  | TA | 100.8 | 21 | 4 | 0.19 | 53 | 71 | 85 | 92 | 97 | 91 |  |
| F | IND | 62.4 | 13 |  | LAC | 312 | 65 | SDS | 4.8 | 1 |  |  |  | TA | 100.8 | 21 | 4 | 0.194 | 52 | 71 | 86 | 93 | 97 | 74 |  |
| G | IND | 48 | 10 |  | SUC | 427.2 | 89 | SDS | 4.8 | 1 |  |  |  |  |  |  | 5 | 0.213 | 47 | 64 | 76 | 84 | 92 | 84 |  |
| H | IND | 48 | 10 |  | SUC | 427.2 | 89 | SDS | 4.8 | 1 |  |  |  |  |  |  | 6 | 0.192 | 52 | 72 | 87 | 93 | 96 | 93 |  |
| I | MTX | 144 | 30 | 33 | LAC | 321.6 | 67 | SDS | 7.2 | 1.5 | P407 | 7.2 | 1.5 |  |  |  | 4 | 0.243 | 44 | 58 | 68 | 74 | 84 | 94 | 2 |
| J | ANT | 50 | 10 |  | LAC | 445 | 89 | SDS | 5 | 1 |  |  |  |  |  |  | 4 | 0.288 | 32 | 51 | 73 | 86 | 91 | 93 | 5 |
| K | DIC | 72 | 15 |  | LAC | 403.2 | 84 | SDS | 4.8 | 1 |  |  |  |  |  |  | 3 | 0.186 | 54 | 74 | 89 | 95 | 98 | 90 |  |
| L | NAA | 168 | 35 | 39 | MAN | 302.4 | 63 | SDS | 4.8 | 1 | PVP | 4.8 | 1 |  |  |  | 6 | 0.226 | 44 | 63 | 80 | 88 | 93 | 94 |  |
| M | NAA | 168 | 35 | 39 | MAN | 297.6 | 62 | SDS | 4.8 | 1 | PVP | 4.8 | 1 | P3000 | 4.8 | 1 | 7 | 0.287 | 31 | 52 | 73 | 85 | 93 | 94 |  |
| N | COP | 48 | 10 |  | LFG | 427.2 | 89 | SDS | 4.8 | 1 |  |  |  |  |  |  | 7 | 4.319 | 0 | 0 | 0 | 3 | 16 | 98 | 10 |
| O | COP | 96 | 20 |  | LFG | 374.4 | 78 | LEC | 9.6 | 2 |  |  |  |  |  |  | 18 | 2.375 | 0 | 0 | 0 | 9 | 39 | 80 | 10 |
| P | CON | 144 | 30 |  | LFG | 326.4 | 68 | LEC | 9.6 | 2 |  |  |  |  |  |  | 1.5 | 4.027 | 0 | 0 | 0 | 7 | 23 | 83 | 10 |

Figure 8A

| Sample No. | Active material | | | Primary Matrix | | | Surfactant #1 | | | Surfactant #2 | | | 2nd Matrix | | | Time (mins.) | D(0.5) μm | Particle Size | | | | | | Yield (%) | Variations |
|---|---|---|---|---|---|---|---|---|---|---|---|---|---|---|---|---|---|---|---|---|---|---|---|---|---|
| | Name | Mass (g) | % w/w | Name | Mass (g) | % w/w | Name | Mass (g) | % w/w | Name | Mass (g) | % w/w | Name | Mass (g) | % w/w | | | % <0.20 μm | % <0.30 μm | % <0.5 μm | % <1.0 μm | % <2.0 μm | No.Ave.(nm) | | |
| A | MEL | 40 | 5 | MAN | 732 | 91.5 | P188 | 24 | 3 | LEC | 4 | 0.5 | | | | 40 | 0.116 | 84 | 97 | 100 | 100 | 100 | | 96 | 1,I |
| B | MEL | 40 | 5 | MAN | 732 | 91.5 | P188 | 24 | 3 | LEC | 4 | 0.5 | | | | 45 | 0.122 | 82 | 97 | 100 | 100 | 100 | | 95 | 1,I |
| C | MEL | 40 | 5 | MAN | 732 | 91.5 | P188 | 24 | 3 | LEC | 4 | 0.5 | | | | 40 | 0.124 | 80 | 96 | 100 | 100 | 100 | | 97 | 1,I |
| D | MEL | 52.5 | 5 | LAC | 960.8 | 91.5 | P188 | 31.5 | 3 | LEC | 5.25 | 0.5 | | | | 50 | 0.156 | 64 | 81 | 89 | 90 | 93 | | 88 | 1,H |
| E | MEL | 40.0 | 5 | MAN | 732.0 | 91.5 | P188 | 24 | 3 | LEC | 4 | 0.5 | | | | 40 | 0.142 | 71 | 88 | 93 | 93 | 95 | | 96 | 1,I |
| F | SAL | 100.0 | 10 | LAC | 890.0 | 89 | LEC | 10.00 | 1 | | | | | | | 15 | 0.137 | 72 | 85 | 89 | 90 | 92 | 75 | 92 | L |
| G | SAL | 100.0 | 10 | LAC | 900.0 | 90 | | | | | | | | | | 15 | 4.954 | 0 | 0 | 2 | 11 | 24 | | 95 | L |
| H | IND | 130.0 | 13 | LAC | 870.0 | 87 | | | | | | | | | | 36 | 0.18 | 56 | 74 | 89 | 96 | 98 | 80 | 65 | |
| I | IND | 130.1 | 13 | LAC | 860.1 | 86 | SDS | 10.00 | 1 | | | | | | | 36 | 0.192 | 52 | 73 | 90 | 95 | 97 | 83 | 85 | |
| J | IND | 130.1 | 13 | LAA | 870.0 | 87 | | | | | | | | | | 36 | 0.186 | 54 | 72 | 86 | 93 | 97 | 80 | 51 | |
| K | DIC | 150.1 | 15 | LAA | 850.3 | 85 | | | | | | | | | | 36 | 0.242 | 41 | 60 | 79 | 92 | 99 | 87 | 27 | |
| L | MEL | 105.0 | 10 | LAC | 913.5 | 87 | SDS | 31.50 | 3 | | | | | | | 20 | 0.137 | 74 | 90 | 95 | 95 | 96 | 79 | 94 | G |
| M | MEL | 105.1 | 10 | LAC | 945 | 90.0 | | | | | | | TA | 215 | 21.5 | 20 | | | | | | | | | 1,G |
| N | IND | 130.0 | 13 | LAA | 860 | 86 | SDS | 10 | 1 | | | | | | | 36 | 0.161 | 62 | 79 | 90 | 93 | 95 | | 80 | 11,N |
| O | IND | 130.0 | 13 | LAA | 645 | 64.5 | SDS | 10 | 1 | | | | | | | 36 | 0.160 | 62 | 79 | 90 | 94 | 96 | | 87 | 11,N |
| P | DIC | 150 | 15 | LAA | 840 | 84 | SDS | 10 | 1 | | | | | | | 36 | 0.152 | 66 | 84 | 95 | 98 | 99 | | 80 | 11,N |
| Q | MEL | 75 | 7.1 | LAC | 943.5 | 90.0 | SDS | 31.5 | 3 | | | | | | | 30 | 0.129 | 78 | 94 | | 100 | | | 89 | 1,M |
| R | MEL | 71.6 | 6.8 | LAC | 946.9 | 90.2 | SDS | 31.5 | 3 | | | | | | | 30 | 0.312 | 72 | 89 | 94 | 94 | 96 | | 92 | 1,F |
| S | IND | 120 | 12 | LAC | 435 | 43.5 | SDS | 10 | 1 | | | | TA | 435 | 43.5 | 44 | 0.168 | 60 | 79 | 92 | 98 | 100 | | 80 | 11,K |

Figure 9A

| Sample No. | Active material Name | Mass (g) | % w/w | Primary Matrix Name | Mass (g) | % w/w | Surfactant #1 Name | Mass (g) | % w/w | Surfactant #2 Name | Mass (g) | % w/w | Matrix 2 Name | Mass (g) | % w/w | Time (mins.) | D(0.5) μm | % <0.20 μm | % <0.30 μm | % < 0.5 μm | % < 1.0 μm | % < 2.0 μm | No.Ave. (nm) | Yield (%) | Variations |
|---|---|---|---|---|---|---|---|---|---|---|---|---|---|---|---|---|---|---|---|---|---|---|---|---|---|
| T | IND | 130 | 13 | LAC | 645 | 64.5 | SDS | 10 | 1 | | | | TA | 215 | 21.5 | 36 | 0.160 | 63 | 79 | 93 | 97 | 99 | | | 11 |
| U | IND | 130 | 13 | LAC | 645 | 64.5 | SDS | 10 | 1 | | | | TA | 215 | 21.5 | 36 | 0.179 | 56 | 72 | 89 | 95 | 97 | | | 11 |
| V | IND | 130 | 13 | LAC | 645 | 64.5 | SDS | 10 | 1 | | | | TA | 215 | 21.5 | 40 | 0.182 | 55 | 70 | 83 | 87 | 92 | | | 11 |
| W | DIC | 150 | 15 | LAC | 840 | 84 | SDS | 10 | 1 | | | | | | | 36 | 0.183 | 55 | 72 | 91 | 96 | 97 | | | 11 |
| X | DIC | 150 | 15 | LAC | 840 | 84 | SDS | 10 | 1 | | | | | | | 36 | 0.186 | 54 | 74 | 94 | 98 | 99 | | | 11 |
| Y | DIC | 150 | 15 | LAC | 840 | 84 | SDS | 10 | 1 | | | | | | | 36 | 0.203 | 49 | 69 | 92 | 97 | 98 | | | 11 |
| Z | NAA | 334 | 35.1 | MAN | 599 | 62.9 | SDS | 9.55 | 1.0 | PVP | 9.55 | 1.0 | | | | 60 | 0.399 | 33 | 44 | 53 | 59 | 69 | | | |
| AA | NAA | 334 | 35.1 | MAN | 599 | 62.9 | SDS | 9.55 | 1.0 | PVP | 9.55 | 1.0 | | | | 60 | 0.337 | 34 | 47 | 58 | 65 | 71 | | | |
| AB | NAA | 334 | 35.1 | MAN | 599 | 62.9 | SDS | 9.55 | 1.0 | PVP | 9.55 | 1.0 | | | | 60 | 0.300 | 37 | 50 | 61 | 69 | 76 | | | |
| AC | NAA | 334 | 35.1 | MAN | 599 | 62.9 | SDS | 9.55 | 1.0 | PVP | 9.55 | 1.0 | | | | 60 | 0.360 | 34 | 46 | 56 | 61 | 69 | | | |
| AD | NAA | 334 | 35.1 | MAN | 599 | 62.9 | SDS | 9.55 | 1.0 | PVP | 9.55 | 1.0 | | | | 60 | 0.366 | 33 | 45 | 55 | 61 | 69 | | | |
| AE | NAA | 334 | 35.1 | MAN | 599 | 62.9 | SDS | 9.55 | 1.0 | PVP | 9.55 | 1.0 | | | | 60 | 0.301 | 36 | 50 | 62 | 69 | 75 | | | |
| AF | NAA | 334 | 35.1 | MAN | 599 | 62.9 | SDS | 9.55 | 1.0 | PVP | 9.55 | 1.0 | | | | 60 | 0.298 | 37 | 50 | 62 | 68 | 74 | | | |
| AG | NAA | 334 | 35.1 | MAN | 599 | 62.9 | SDS | 9.55 | 1.0 | PVP | 9.55 | 1.0 | | | | 60 | 0.195 | 51 | 65 | 74 | 78 | 83 | | | |
| AH | NAA | 334 | 35.1 | MAN | 599 | 62.9 | SDS | 9.55 | 1.0 | PVP | 9.55 | 1.0 | | | | 60 | 0.294 | 37 | 51 | 62 | 68 | 76 | | | |
| AI | MEL | 105 | 11 | LAC | 864 | 86.4 | SDS | 31.5 | 3 | | | | | | | 20 | 0.189 | 53 | 72 | 84 | 88 | 94 | | | F |
| AJ | MEL | 105 | 11 | LAC | 864 | 86.4 | SDS | 31.5 | 3 | | | | | | | 25 | 0.153 | 65 | 84 | 94 | 95 | 98 | | | F |
| AK | MEL | 105 | 11 | LAC | 864 | 86.4 | SDS | 31.5 | 3 | | | | | | | 30 | 0.138 | 74 | 91 | 96 | 96 | 97 | | | F |
| AL | MEL | 105 | 11 | LAC | 864 | 86.4 | SDS | 31.5 | 3 | | | | | | | 35 | 0.126 | 79 | 96 | 100 | 100 | 100 | | 90 | F |

Figure 9B

| Sample No. | Active material Name | Active material Mass (g) | Active material % w/w | Active material % v/v | Primary Matrix Name | Primary Matrix Mass (g) | Primary Matrix % w/w | Surfactant #1 Name | Surfactant #1 Mass (g) | Surfactant #1 % w/w | Time (mins.) | D(0.5) μm | % <0.20 μm | % <0.30 μm | % < 0.5 μm | % < 1.0 μm | % < 2.0 μm | Yield (%) | Variations |
|---|---|---|---|---|---|---|---|---|---|---|---|---|---|---|---|---|---|---|---|
| A | DIC | 2.50 | 10 | | MAN | 22.5 | 89 | SDS | 0.25 | 1 | 30 | 0.237 | 40 | 63 | 83 | 93 | 97 | | |
| B | NAA | 70 | 35 | | LAC | 128 | 64 | SDS | 2 | 1 | 60 | 0.224 | 72 | 81 | 92 | 81 | 92 | | |
| C | NAA | 70 | 35 | | MAN | 128 | 64 | SDS | 2 | 1 | 60 | 0.177 | 57 | 74 | 86 | 90 | 93 | | |
| D | NAA | 80 | 40 | 40 | LAC | 118 | 60 | | | | 45 | 2.039 | 19 | 26 | 31 | 36 | 49 | | |
| E | DIC | 1650 | 15 | | LAC | 9240 | 84 | SDS | 110 | 1 | 20 | 0.24 | 42 | 58 | 74 | 86 | 94 | 91 | |
| F | DIC | 3750 | 15 | | LAC | 21000 | 84 | SDS | 250 | 1 | 25 | 0.214 | 49 | 68 | 82 | 93 | 97 | 97 | |

Figure 10A

| Sample No. | Active material | | | | Primary Matrix | | | Surfactant #1 | | | Surfactant #2 | | | Surfactant #3 | | | Disintegrant | | | Time (mins.) | Particle Size | | | | | | Yield (%) | Variations |
|---|---|---|---|---|---|---|---|---|---|---|---|---|---|---|---|---|---|---|---|---|---|---|---|---|---|---|---|---|
| | Name | Mass (g) | % w/w | % v/v | Name | Mass (g) | % w/w | Name | Mass (g) | % w/w | Name | Mass (g) | % w/w | Name | Mass (g) | % w/w | Name | Mass (g) | % w/w | | D(0.5) μm | % <0.20 μm | % <0.30 μm | % <0.5 μm | % <1.0 μm | % <2.0 μm | | |
| A | NAA | 105 | 35 | 39 | MAN | 189 | 63 | SDS | 3 | 1 | | | | | | | | | | 80 | 0.19 | 53 | 71 | 84 | 91 | 95 | 90 | |
| B | NAA | 105 | 35 | 39 | MAN | 189 | 63 | SDS | 3 | 1 | P3000 | 3 | 1 | | | | | | | 40 | 0.89 | 26 | 36 | 45 | 51 | 57 | | |
| C | NAA | 105 | 35 | 39 | MAN | 189 | 63 | SDS | 3 | 1 | P407 | 3.1 | 1 | | | | | | | 60 | 0.31 | 36 | 49 | 61 | 69 | 76 | | |
| D | NAA | 105 | 35 | 39 | MAN | 189 | 63 | SDS | 3 | 1 | P407 | 3.1 | 1 | | | | | | | 80 | 0.19 | 52 | 70 | 84 | 90 | 93 | 82 | |
| E | NAA | 105.1 | 35 | 39 | MAN | 192 | 64 | SDS | 3 | 1 | P407 | 3.1 | 1 | | | | | | | 80 | 0.24 | 43 | 59 | 72 | 78 | 81 | 84.6 | |
| F | NAA | 105 | 35 | 39 | MAN | 171 | 57 | SDS | 3 | 1 | P3000 | 3 | 1 | PVP | 3 | 1 | PML | 15 | 5 | 80 | 0.27 | 39 | 54 | 67 | 74 | 78 | 89.2 | 12 |
| G | NAA | 105 | 35 | 39 | MAN | 171 | 57 | SDS | 3 | 1 | P407 | 3 | 1 | PVP | 3.02 | 1 | PML | 15.1 | 5 | 80 | | | | | | | 88.2 | |
| H | NAA | 105.2 | 35 | 39 | MAN | 174 | 58 | SDS | 3 | 1 | PVP | 3 | 1 | | | | PML | 15.0 | 5 | 80 | | | | | | | 87.1 | |
| I | NAA | 105 | 35 | 39 | MAN | 189 | 63 | SDS | 3 | 1 | P3000 | 3 | 1 | PVP | 3.01 | 1 | | | | 80 | 0.25 | 27 | 67 | 91 | 100 | 100 | 88 | |
| J | NAA | 105.7 | 35 | 39 | MAN | 186 | 64 | SDS | 3 | 1 | P3000 | 3 | 1 | | | | | | | 80 | 0.24 | 29 | 68 | 90 | 99 | 100 | 89.7 | |
| K | NAA | 105.1 | 35.0 | 39 | MAN | 195 | 65.0 | | | | | | | | | | | | | 80 | 0.19 | 53 | 70 | 82 | 87 | 91 | 81 | |
| L | NAA | 105 | 35.0 | | MAN | 180 | 60.0 | | | | | | | | | | MCC | 15 | 5 | 80 | 0.26 | 40 | 54 | 65 | 69 | 75 | 66 | 12,D |
| M | NAA | 105 | 35.0 | | MAN | 180 | 60.0 | | | | | | | | | | PML | 15 | 5 | 80 | 0.24 | 42 | 58 | 69 | 76 | 85 | 51 | 12,D |

Figure 11A

| Sample No. | Active material Name | Mass (g) | % w/w | Primary Matrix Name | Mass (g) | % w/w | Surfactant #1 Name | Mass (g) | % w/w | Surfactant #2 Name | Mass (g) | % w/w | Time (mins.) | D(0.5) μm | % <0.20 μm | % <0.30 μm | % < 0.5 μm | % < 1.0 μm | % < 2.0 μm | Yield (%) | Variations |
|---|---|---|---|---|---|---|---|---|---|---|---|---|---|---|---|---|---|---|---|---|---|
| A | NAA | 1.5 | 30 | LAC | 3.2 | 64 | SDS | 0.05 | 1 | MCC | 0.25 | 5 | 40 | 2.6 | 29 | 41 | 47 | 61 | 77 | 86 |  |
| B | 14A |  |  |  |  |  |  |  |  |  |  |  |  | 0.2 | 68 | 79 | 84 | 94 | 99 |  | 12 |
| C | NAA | 1.5 | 30 | LAC | 3.45 | 69 | SDS | 0.05 | 1 |  |  |  | 40 | 0.2 | 79 | 95 | 98 | 100 | 100 | 95 |  |
| D | 14C |  |  |  |  |  |  |  |  |  |  |  |  | 0.2 | 80 | 94 | 97 | 100 | 100 |  | 12 |
| E | 14C | 2.5 | 95 | MCC | 0.13 | 5 |  |  |  |  |  |  | 1 | 1.3 | 34 | 49 | 52 | 56 | 60 | 88 |  |
| F | 14C | 2.5 | 91 | MCC | 0.25 | 9 |  |  |  |  |  |  | 1 | 0.8 | 36 | 52 | 56 | 62 | 72 | 83 |  |
| G | 14E |  |  |  |  |  |  |  |  |  |  |  |  | 0.2 | 79 | 92 | 96 | 99 | 100 |  | 12 |
| H | 14F |  |  |  |  |  |  |  |  |  |  |  |  | 0.2 | 79 | 93 | 97 | 99 | 100 |  | 12 |
| I | NAA | 1.5 | 30 | LAC | 2.95 | 59 | SDS | 0.05 | 1 | MCC | 0.5 | 10 | 40 | 6.4 | 12 | 19 | 25 | 43 | 64 | 96 |  |
| J | NAA | 1.5 | 30 | LAC | 2.45 | 49 | SDS | 0.05 | 1 | MCC | 1 | 20 | 40 | 8.6 | 0 | 0 | 7 | 31 | 56 | 95 |  |
| K | 14I |  |  |  |  |  |  |  |  |  |  |  |  | 1.7 | 32 | 44 | 53 | 77 | 94 |  | 12 |
| L | 14J |  |  |  |  |  |  |  |  |  |  |  |  | 4.1 | 0 | 0 | 12 | 61 | 92 |  | 12 |

Figure 12A

FORMULATION OF DICLOFENAC

RELATED APPLICATIONS

This application is a continuation and claims priority to U.S. application Ser. No. 14/277,287, filed May 14, 2014, which is a continuation of U.S. application Ser. No. 14/167,652, filed Jan. 29, 2014, which is a continuation of U.S. application Ser. No. 13/266,122, filed Feb. 16, 2012, which is a U.S. national stage under 35 USC §371 of International Application Number PCT/AU2010/000471, filed on 23 Apr. 2010, which claims priority to AU Application No. 2009901748, filed on 24 Apr. 2009 and U.S. Application No. 61/172,291, filed on 24 Apr. 2009, the entire contents of which applications is hereby incorporated by reference.

FIELD OF THE INVENTION

The present invention relates to methods for producing particles of diclofenac using dry milling processes as well as compositions comprising diclofenac, medicaments produced using diclofenac in particulate form and/or compositions, and to methods of treatment of an animal, including man, using a therapeutically effective amount of diclofenac administered by way of said medicaments.

BACKGROUND

Poor bioavailability is a significant problem encountered in the development of compositions in the therapeutic, cosmetic, agricultural and food industries, particularly those materials containing a biologically active material that is poorly soluble in water at physiological pH. An active material's bioavailability is the degree to which the active material becomes available to the target tissue in the body or other medium after systemic administration through, for example, oral or intravenous means. Many factors affect bioavailability, including the form of dosage and the solubility and dissolution rate of the active material.

In therapeutic applications, poorly and slowly water-soluble materials tend to be eliminated from the gastrointestinal tract before being absorbed into the circulation. In addition, poorly soluble active agents tend to be disfavored or even unsafe for intravenous administration due to the risk of particles of agent blocking blood flow through capillaries.

It is known that the rate of dissolution of a particulate drug will increase with increasing surface area. One way of increasing surface area is decreasing particle size. Consequently, methods of making finely divided or sized drugs have been studied with a view to controlling the size and size range of drug particles for pharmaceutical compositions.

For example, dry milling techniques have been used to reduce particle size and hence influence drug absorption. However, in conventional dry milling the limit of fineness is reached generally in the region of about 100 microns (100,000 nm), at which point material cakes on the milling chamber and prevents any further diminution of particle size. Alternatively, wet grinding may be employed to reduce particle size, but flocculation restricts the lower particle size limit to approximately 10 microns (10,000 nm). The wet milling process, however, is prone to contamination, thereby leading to a bias in the pharmaceutical art against wet milling. Another alternative milling technique, commercial airjet milling, has provided particles ranging in average size from as low as about 1 to about 50 microns (1,000-50,000 nm).

There are several approaches currently used to formulate poorly soluble active agents. One approach is to prepare the active agent as a soluble salt. Where this approach cannot be employed, alternate (usually physical) approaches are employed to improve the solubility of the active agent. Alternate approaches generally subject the active agent to physical conditions that change the agent's physical and or chemical properties to improve its solubility. These include process technologies such as micronization, modification of crystal or polymorphic structure, development of oil based solutions, use of co-solvents, surface stabilizers or complexing agents, micro-emulsions, supercritical fluid and production of solid dispersions or solutions. More than one of these processes may be used in combination to improve formulation of a particular therapeutic material. Many of these approaches commonly convert a drug into an amorphous state, which generally leads to a higher dissolution rate. However, formulation approaches that result in the production of amorphous material are not common in commercial formulations due to concerns relating to stability and the potential for material to re-crystallize.

These techniques for preparing such pharmaceutical compositions tend to be complex. By way of example, a principal technical difficulty encountered with emulsion polymerization is the removal of contaminants, such as unreacted monomers or initiators (which may have undesirable levels of toxicity), at the end of the manufacturing process.

Another method of providing reduced particle size is the formation of pharmaceutical drug microcapsules, which techniques include micronizing, polymerisation and co-dispersion. However, these techniques suffer from a number of disadvantages including at least the inability to produce sufficiently small particles such as those obtained by milling, and the presence of co-solvents and/or contaminants such as toxic monomers which are difficult to remove, leading to expensive manufacturing processes.

Over the last decade, intense scientific investigation has been carried out to improve the solubility of active agents by converting the agents to ultra fine powders by methods such as milling and grinding. These techniques may be used to increase the dissolution rate of a particulate solid by increasing the overall surface area and decreasing the mean particle size.

U.S. Pat. No. 6,634,576 discloses examples of wet-milling a solid substrate, such as a pharmaceutically active compound, to produce a "synergetic co-mixture".

International Patent Application PCT/AU2005/001977 (Nanoparticle Composition(s) and Method for Synthesis Thereof) describes, inter alia, a method comprising the step of contacting a precursor compound with a co-reactant under mechanochemical synthesis conditions wherein a solid-state chemical reaction between the precursor compound and the co-reactant produces therapeutically active nanoparticles dispersed in a carrier matrix. Mechanochemical synthesis, as discussed in International Patent Application PCT/AU2005/001977, refers to the use of mechanical energy to activate, initiate or promote a chemical reaction, a crystal structure transformation or a phase change in a material or a mixture of materials, for example by agitating a reaction mixture in the presence of a milling media to transfer mechanical energy to the reaction mixture, and includes without limitation "mechanochemical activation", "mechanochemical processing", "reactive milling", and related processes.

International Patent Application PCT/AU2007/000910 (Methods for the preparation of biologically active compounds in nanoparticulate form) describes, inter alia, a method for dry milling raloxifene with lactose and NaCl which produced nanoparticulate raloxifene without significant aggregation problems.

One limitation of many of the prior art processes is that they are not suitable for commercial scale milling. The present invention provides methods for overcoming the problems identified by the prior art by providing a milling process which provides particles with increased surface area, yet can also be scaled up to a commercial scale.

One example of a therapeutic area where this technology could be applied in is the area of acute pain management. Many pain medications such as diclofenac are commonly prescribed as pain relief for chronic pain. As a result they are commonly taken on a daily basis to maintain an effective therapeutic level. Diclofenac is a poorly water soluble drug so dissolution and absorption to the body is slow. So a method such as the present invention which provides for improved dissolution, will likely provide much faster absorption resulting in a more rapid onset of the therapeutic effect. By using a method such as the present invention, which provides faster absorption, a drug such as diclofenac, could be used more readily to treat acute pain as well as chronic pain.

Although the background to the present invention is discussed in the context of improving the bioavailability of materials that are poorly or slowly water soluble, the applications of the methods of the present invention are not limited to such, as is evident from the following description of the invention.

Further, although the background to the present invention is largely discussed in the context of improving the bioavailability of therapeutic or pharmaceutical compounds, the applications of the methods of the present invention are clearly not limited to such. For example, as is evident from the following description, applications of the methods of the present invention include but are not limited to: nutraceutical and nutritional compounds, complementary medicinal compounds, veterinary therapeutic applications and agricultural chemical applications, such as pesticide, fungicide or herbicide.

Furthermore an application of the current invention would be to materials which contain a biologically active compound such as, but not limited to a therapeutic or pharmaceutical compound, a nutraceutical or nutrient, a complementary medicinal product such as active components in plant or other naturally occurring material, a veterinary therapeutic compound or an agricultural compound such as a pesticide, fungicide or herbicide. Specific examples would be the spice turmeric that contains the active compound curcumin, or flax seed that contains the nutrient ALA an omega 3 fatty acid. As these specific examples indicate this invention could be applied to, but not limited to, a range of natural products such as seeds, cocoa and cocoa solids, coffee, herbs, spices, other plant materials or food materials that contain a biologically active compound. The application of this invention to these types of materials would enable greater availability of the active compound in the materials when used in the relevant application. For example where material subject to this invention is orally ingested the active would be more bioavailable.

SUMMARY OF THE INVENTION

In one aspect the present invention is directed to the unexpected finding that particles of a biologically active material can be produced by dry milling processes at commercial scale. In one surprising aspect the particle size produced by the process is equal to or less than 2000 nm. In another surprising aspect the particle size produced by the process is equal to or less than 1000 nm. In another surprising aspect the crystallinity of the active material is unchanged or not substantially changed. In a preferred embodiment the present invention is directed to the unexpected finding that particles of diclofenac can be produced by dry milling processes at commercial scale.

Thus in a first aspect the invention comprises a method producing a composition, comprising the steps of dry milling a solid biologically active material and a millable grinding matrix in a mill comprising a plurality of milling bodies, for a time period sufficient to produce particles of the biologically active material dispersed in an at least partially milled grinding material.

In one preferred embodiment, the average particle size, determined on a particle number basis, is equal to or less than a size selected from the group 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm and 100 nm. Preferably, the average particle size is equal to or greater than 25 nm.

In another preferred embodiment, the particles have a median particle size, determined on a particle volume basis, equal or less than a size selected from the group 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm and 100 nm. Preferably, the median particle size is equal to or greater than 25 nm. Preferably, the percentage of particles, on a particle volume basis, is selected from the group consisting of: 50%, 60%, 70%, 80%, 90%, 95% and 100% less than 2000 nm (%<2000 nm). Preferably, the percentage of particles, on a particle volume basis, is selected from the group consisting of: 50%, 60%, 70%, 80%, 90%, 95% and 100% less than 1000 nm (%<1000 nm). Preferably, the percentage of particles, on a particle volume basis, is selected from the group consisting of: 0%, 10%, 20%, 30%, 40%, 50%, 60%, 70%, 80%, 90%, 95% and 100% less than 500 nm (%<500 nm). Preferably, the percentage of particles, on a particle volume basis, is selected from the group consisting of: 0%, 10%, 20%, 30%, 40%, 50%, 60%, 70%, 80%, 90%, 95% and 100% less than 300 nm (%<300 nm). Preferably, the percentage of particles, on a particle volume basis, is selected from the group consisting of: 0%, 10%, 20%, 30%, 40%, 50%, 60%, 70%, 80%, 90%, 95% and 100% less than 200 nm (%<200 nm). Preferably, the Dx of the particle size distribution, as measured on a particle volume basis, is selected from the group consisting of less than or equal to 10,000 nm, 5000 nm, 3000 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm, and 100 nm; wherein x is greater than or equal to 90.

In another preferred embodiment, the crystallinity profile of the biologically active material is selected from the group consisting of: at least 50% of the biologically active material is crystalline, at least 60% of the biologically active material is crystalline, at least 70% of the biologically active material is crystalline, at least 75% of the biologically active material is crystalline, at least 85% of the biologically active material is crystalline, at least 90% of the biologically active material is crystalline, at least 95% of the biologically active material is crystalline and at least 98% of the biologically active material is crystalline. More preferably, the crystallinity profile of the biologically active material is substantially equal to the crystallinity profile of the biologically active material before the material was subjected to the method as described herein.

In another preferred embodiment, the amorphous content of the biologically active material is selected from the group consisting of: less than 50% of the biologically active material is amorphous, less than 40% of the biologically active material is amorphous, less than 30% of the biologically active material is amorphous, less than 25% of the biologically active material is amorphous, less than 15% of the biologically active material is amorphous, less than 10% of the biologically active material is amorphous, less than 5% of the biologically active material is amorphous and less than 2% of the biologically active material is amorphous. Preferably, the biologically active material has no significant increase in amorphous content after subjecting the material to the method as described herein.

In another preferred embodiment, the milling time period is a range selected from the group consisting of: between 10 minutes and 2 hours, between 10 minutes and 90 minutes, between 10 minutes and 1 hour, between 10 minutes and 45 minutes, between 10 minutes and 30 minutes, between 5 minutes and 30 minutes, between 5 minutes and 20 minutes, between 2 minutes and 10 minutes, between 2 minutes and 5 minutes, between 1 minutes and 20 minutes, between 1 minute and 10 minutes, and between 1 minute and 5 minutes.

In another preferred embodiment, the milling medium is selected from the group consisting of: ceramics, glasses, polymers, ferromagnetics and metals. Preferably, the milling medium is steel balls having a diameter selected from the group consisting of: between 1 and 20 mm, between 2 and 15 mm and between 3 and 10 mm. In another preferred embodiment, the milling medium is zirconium oxide balls having a diameter selected from the group consisting of: between 1 and 20 mm, between 2 and 15 mm and between 3 and 10 mm. Preferably, the dry milling apparatus is a mill selected from the group consisting of: attritor mills (horizontal or vertical), nutating mills, tower mills, pearl mills, planetary mills, vibratory mills, eccentric vibratory mills, gravity-dependent-type ball mills, rod mills, roller mills and crusher mills. Preferably, the milling medium within the milling apparatus is mechanically agitated by 1, 2 or 3 rotating shafts. Preferably, the method is configured to produce the biologically active material in a continuous fashion.

Preferably, the total combined amount of biologically active material and grinding matrix in the mill at any given time is equal to or greater than a mass selected from the group consisting of: 200 grams, 500 grams, 1 kg, 2 kg, 5 kg, 10 kg, 20 kg, 30 kg, 50 kg, 75 kg, 100 kg, 150 kg, 200 kg.

Preferably, the total combined amount of biologically active material and grinding matrix is less than 2000 kg.

Preferably, the biologically active material is selected from the group consisting of: diclofenac or a derivative or salt thereof.

In another preferred embodiment, the grinding matrix is a single material or is a mixture of two or more materials in any proportion. Preferably, the single material or a mixture of two or more materials is selected from the group consisting of: mannitol, sorbitol, Isomalt, xylitol, maltitol, lactitol, erythritol, arabitol, ribitol, glucose, fructose, mannose, galactose, anhydrous lactose, lactose monohydrate, sucrose, maltose, trehalose, maltodextrins, dextrin, Inulin, dextrates, polydextrose, starch, wheat flour, corn flour, rice flour, rice starch, tapioca flour, tapioca starch, potato flour, potato starch, other flours and starches, milk powder, skim milk powders, other milk solids and derivatives, soy flour, soy meal or other soy products, cellulose, microcrystalline cellulose, microcrystalline cellulose based co-blended materials, pregelatinized (or partially) starch, HPMC, CMC, HPC, citric acid, tartaric acid, malic acid, maleic acid fumaric acid, ascorbic acid, succinic acid, sodium citrate, sodium tartrate, sodium malate, sodium ascorbate, potassium citrate, potassium tartrate, potassium malate, sodium acetate, potassium ascorbate, sodium carbonate, potassium carbonate, magnesium carbonate, sodium bicarbonate, potassium bicarbonate, calcium carbonate, dibasic calcium phosphate, tribasic calcium phosphate, sodium sulfate, sodium chloride, sodium metabisulphite, sodium thiosulfate, ammonium chloride, glauber's salt, ammonium carbonate, sodium bisulfate, magnesium sulfate, potash alum, potassium chloride, sodium hydrogen sulfate, sodium hydroxide, crystalline hydroxides, hydrogen carbonates, ammonium chloride, methylamine hydrochloride, ammonium bromide, silica, thermal silica, alumina, titanium dioxide, talc, chalk, mica, kaolin, bentonite, hectorite, magnesium trisilicate, clay based materials or aluminium silicates, sodium lauryl sulfate, sodium stearyl sulfate, sodium cetyl sulfate, sodium cetostearyl sulfate, sodium docusate, sodium deoxycholate, N-lauroylsarcosine sodium salt, glyceryl monostearate, glycerol distearate glyceryl palmitostearate, glyceryl behenate, glyceryl caprylate, glyceryl oleate, benzalkonium chloride, CTAB, CTAC, Cetrimide, cetylpyridinium chloride, cetylpyridinium bromide, benzethonium chloride, PEG 40 stearate, PEG 100 stearate, poloxamer 188, poloxamer 338, poloxamer 407 polyoxyl 2 stearyl ether, polyoxyl 100 stearyl ether, polyoxyl 20 stearyl ether, polyoxyl 10 stearyl ether, polyoxyl 20 cetyl ether, polysorbate 20, polysorbate 40, polysorbate 60, polysorbate 61, polysorbate 65, polysorbate 80, polyoxyl 35 castor oil, polyoxyl 40 castor oil, polyoxyl 60 castor oil, polyoxyl 100 castor oil, polyoxyl 200 castor oil, polyoxyl 40 hydrogenated castor oil, polyoxyl 60 hydrogenated castor oil, polyoxyl 100 hydrogenated castor oil, polyoxyl 200 hydrogenated castor oil, cetostearyl alcohol, macrogel 15 hydroxystearate, sorbitan monopalmitate, sorbitan monostearate, sorbitan trioleate, sucrose palmitate, sucrose stearate, sucrose distearate, sucrose laurate, glycocholic acid, sodium glycholate, cholic acid, sodium cholate, sodium deoxycholate, deoxycholic acid, sodium taurocholate, taurocholic acid, sodium taurodeoxycholate, taurodeoxycholic acid, soy lecithin, phosphatidylcholine, phosphatidylethanolamine, phosphatidylserine, phosphatidylinositol, PEG4000, PEG6000, PEG8000, PEG10000, PEG20000, alkyl naphthalene sulfonate condensate/Lignosulfonate blend, calcium dodecylbenzene sulfonate, sodium dodecylbenzene sulfonate, diisopropyl naphthaenesulphonate, erythritol distearate, naphthalene sulfonate formaldehyde condensate, nonylphenol ethoxylate (poe-30), tristyrylphenol ethoxylate, polyoxyethylene (15) tallowalkylamines, sodium alkyl naphthalene sulfonate, sodium alkyl naphthalene sulfonate condensate, sodium alkylbenzene sulfonate, sodium isopropyl naphthalene sulfonate, sodium methyl naphthalene formaldehyde sulfonate, sodium n-butyl naphthalene sulfonate, tridecyl alcohol ethoxylate (poe-18), triethanolamine isodecanol phosphate ester, triethanolamine tristyrylphosphate ester, tristyrylphenol ethoxylate sulfate, bis(2-hydroxyethyl)tallowalkylamines. Preferably, the concentration of the single (or first) material is selected from the group consisting of: 5-99% w/w, 10-95% w/w, 15-85% w/w, of 20-80% w/w, 25-75% w/w, 30-60% w/w, 40-50% w/w. Preferably, the concentration of the second or subsequent material is selected from the group consisting of: 5-50% w/w, 5-40% w/w, 5-30% w/w, of 5-20% w/w, 10-40% w/w, 10-30% w/w, 10-20% w/w, 20-40% w/w, or 20-30% w/w or if the second or subsequent material is a surfactant or water soluble polymer the concentration is selected from 0.1-10% w/w, 0.1-5% w/w, 0.1-2.5% w/w, of 0.1-2% w/w, 0.1-1%, 0.5-5% w/w, 0.5-3% w/w, 0.5-2% w/w, 0.5-1.5%, 0.5-1% w/w, of 0.75-1.25% w/w, 0.75-1% and 1% w/w.

Preferably, the grinding matrix is selected from the group consisting of:
(a) lactose monohydrate or lactose monohydrate combined with at least one material selected from the group consisting of: xylitol; lactose anhydrous; microcrystalline cellulose; sucrose; glucose; sodium chloride; talc; kaolin; calcium carbonate; malic acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(b) lactose anhydrous or lactose anhydrous combined with at least one material selected from the group consisting of: lactose monohydrate; xylitol; microcrystalline cellulose; sucrose; glucose; sodium chloride; talc; kaolin; calcium carbonate; malic acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(c) mannitol or mannitol combined with at least one material selected from the group consisting of: lactose monohydrate; xylitol; lactose anhydrous; microcrystalline cellulose; sucrose; glucose; sodium chloride; talc; kaolin; calcium carbonate; malic acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(d) Sucrose or sucrose combined with at least one material selected from the group consisting of: lactose monohydrate; lactose anhydrous; mannitol; microcrystalline cellulose; glucose; sodium chloride; talc; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate;

nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(e) Glucose or glucose combined with at least one material selected from the group consisting of: lactose monohydrate; lactose anhydrous; mannitol; microcrystalline cellulose; sucrose; sodium chloride; talc; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(f) Sodium chloride or sodium chloride combined with at least one material selected from the group consisting of: lactose monohydrate; lactose anhydrous; mannitol; microcrystalline cellulose; sucrose; glucose; talc; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(g) xylitol or xylitol combined with at least one material selected from the group consisting of: lactose monohydrate; lactose anhydrous; mannitol; microcrystalline cellulose; sucrose; glucose; sodium chloride; talc; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(h) Tartaric acid or tartaric acid combined with at least one material selected from the group consisting of: lactose monohydrate; lactose anhydrous; mannitol; microcrystalline cellulose; sucrose; glucose; sodium chloride; talc; kaolin; calcium carbonate; malic acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone;

sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(i) microcrystalline cellulose or microcrystalline cellulose combined with at least one material selected from the group consisting of: lactose monohydrate; xylitol; lactose anhydrous; mannitol; sucrose; glucose; sodium chloride; talc; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(j) Kaolin combined with at least one material selected from the group consisting of: lactose monohydrate; xylitol; lactose anhydrous; mannitol; microcrystalline cellulose; sucrose; glucose; sodium chloride; talc; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(k) Talc combined with at least one material selected from the group consisting of: lactose monohydrate; xylitol; lactose anhydrous; mannitol; microcrystalline cellulose; sucrose; glucose; sodium chloride; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

Preferably, the grinding matrix is selected from the group consisting of: a material considered to be 'Generally Regarded as Safe' (GRAS) for pharmaceutical products; a material considered acceptable for use in an agricultural formulation; and a material considered acceptable for use in a veterinary formulation.

In another preferred embodiment, a milling aid or combination of milling aids is used. Preferably, the milling aid is selected from the group consisting of: colloidal silica, a surfactant, a polymer, a stearic acid and derivatives thereof. Preferably, the surfactant is selected from the group consisting of: polyoxyethylene alkyl ethers, polyoxyethylene stearates, polyethylene glycols (PEG), poloxamers, poloxamines, sarcosine based surfactants, polysorbates, aliphatic alcohols, alkyl and aryl sulfates, alkyl and aryl polyether sulfonates and other sulfate surfactants, trimethyl ammonium based surfactants, lecithin and other phospholipids, bile salts, polyoxyethylene castor oil derivatives, polyoxyethylene sorbitan fatty acid esters, Sorbitan fatty acid esters, Sucrose fatty acid esters, alkyl glucopyranosides, alkyl maltopyranosides, glycerol fatty acid esters, Alkyl Benzene Sulphonic Acids, Alkyl Ether Carboxylic Acids, Alkyl and aryl Phosphate esters, Alkyl and aryl Sulphate esters, Alkyl and aryl Sulphonic acids, Alkyl Phenol Phosphates esters, Alkyl Phenol Sulphates esters, Alkyl and Aryl Phosphates, Alkyl Polysaccharides, Alkylamine Ethoxylates, Alkyl-Naphthalene Sulphonates formaldehyde condensates, Sulfosuccinates, lignosulfonates, Ceto-Oleyl Alcohol Ethoxylates, Condensed Naphthalene Sulphonates, Dialkyl and Alkyl Naphthalene Sulphonates, Di-alkyl Sulphosuccinates, Ethoxylated nonylphenols, Ethylene Glycol Esters, Fatty Alcohol Alkoxylates, Hydrogenated tallowalkylamines, Mono-alkyl Sulphosuccinamates, Nonyl Phenol Ethoxylates, Sodium Oleyl N-methyl Taurate, Tallowalkylamines, linear and branched dodecylbenzene sulfonic acids Preferably, the surfactant is selected from the group consisting of: sodium lauryl sulfate, sodium stearyl sulfate, sodium cetyl sulfate, sodium cetostearyl sulfate, sodium docusate, sodium deoxycholate, N-lauroylsarcosine sodium salt, glyceryl monostearate, glycerol distearate glyceryl palmitostearate, glyceryl behenate, glyceryl caprylate, glyceryl oleate, benzalkonium chloride, CTAB, CTAC, Cetrimide, cetylpyridinium chloride, cetylpyridinium bromide, benzethonium chloride, PEG 40 stearate, PEG 100 stearate, poloxamer 188, poloxamer 338, poloxamer 407 polyoxyl 2 stearyl ether, polyoxyl 100 stearyl ether, polyoxyl 20 stearyl ether, polyoxyl 10 stearyl ether, polyoxyl 20 cetyl ether, polysorbate 20, polysorbate 40, polysorbate 60, polysorbate 61, polysorbate 65, polysorbate 80, polyoxyl 35 castor oil, polyoxyl 40 castor oil, polyoxyl 60 castor oil, polyoxyl 100 castor oil, polyoxyl 200 castor oil, polyoxyl 40 hydrogenated castor oil, polyoxyl 60 hydrogenated castor oil, polyoxyl 100 hydrogenated castor oil, polyoxyl 200 hydrogenated castor oil, cetostearyl alcohol, macrogel 15 hydroxystearate, sorbitan monopalmitate, sorbitan monostearate, sorbitan trioleate, Sucrose Palmitate, Sucrose Stearate, Sucrose Distearate, Sucrose laurate, Glycocholic acid, sodium Glycholate, Cholic Acid, Soidum Cholate, Sodium Deoxycholate, Deoxycholic acid, Sodium taurocholate, taurocholic acid, Sodium taurodeoxycholate, taurodeoxycholic acid, soy lecithin, phosphatidylcholine, phosphatidylethanolamine, phosphatidylserine, phosphatidylinositol, PEG4000, PEG6000, PEG8000, PEG10000, PEG20000, alkyl naphthalene sulfonate condensate/Lignosulfonate blend, Calcium Dodecylbenzene Sulfonate, Sodium Dodecylbenzene Sulfonate, Diisopropyl naphthaenesulphonate, erythritol distearate, Naphthalene Sulfonate Formaldehyde Condensate, nonylphenol ethoxylate (poe-30), Tristyrylphenol Ethoxylate, Polyoxyethylene (15) tallowalkylamines, sodium alkyl naphthalene sulfonate, sodium alkyl naphthalene sulfonate condensate, sodium alkylbenzene sulfonate, sodium isopropyl naphthalene sulfonate, Sodium Methyl Naphthalene Formaldehyde Sulfonate, sodium n-butyl naphthalene sulfonate, tridecyl alcohol ethoxylate (poe-18), Triethanolamine isodecanol phosphate ester, Triethanolamine tristyrylphosphate ester, Tristyrylphenol Ethoxylate Sulfate, Bis(2-hydroxyethyl)tallowalkylamines.

Preferably the polymer is selected from the list of: polyvinylpyrrolidones (PVP), polyvinylalcohol, acrylic acid based polymers and copolymers of acrylic acid Preferably, the milling aid has a concentration selected from the group consisting of: 0.1-10% w/w, 0.1-5% w/w, 0.1-2.5% w/w, of 0.1-2% w/w, 0.1-1%, 0.5-5% w/w, 0.5-3% w/w, 0.5-2% w/w, 0.5-1.5%, 0.5-1 w/w, of 0.75-1.25% w/w, 0.75-1% and 1% w/w.

In another preferred embodiment of the invention, a facilitating agent is used or combination of facilitating agents is used. Preferably, the facilitating agent is selected from the group consisting of: surfactants, polymers, binding agents, filling agents, lubricating agents, sweeteners, flavouring agents, preservatives, buffers, wetting agents, disintegrants, effervescent agents, agents that may form part of a medicament, including a solid dosage form or a dry powder inhalation formulation and other material required for specific drug delivery. Preferably, the facilitating agent is added during dry milling. Preferably, the facilitating agent is added to the dry milling at a time selected from the group consisting of: with 1-5% of the total milling time remaining, with 1-10% of the total milling time remaining, with 1-20% of the total milling time remaining, with 1-30% of the total milling time remaining, with 2-5% of the total milling time remaining, with 2-10% of the total milling time remaining, with 5-20% of the total milling time remaining and with 5-20% of the total milling time remaining. Preferably, the disintegrant is selected from the group consisting of: crosslinked PVP, cross linked carmellose and sodium starch glycolate. Preferably, the facilitating agent is added to the milled biologically active material and grinding matrix and further processed in a mechanofusion process. Mechanofusion milling causes mechanical energy to be applied to powders or mixtures of particles in the micrometer and nanometer range.

The reasons for including facilitating agents include, but are not limited to providing better dispersibility, control of agglomeration, the release or retention of the active particles from the delivery matrix. Examples of facilitating agents include, but are not limited to crosslinked PVP (crospovidone), cross linked carmellose (croscarmellose), sodium starch glycolate, Povidone (PVP), Povidone K12, Povidone K17, Povidone K25, Povidone K29/32 and Povidone K30, stearic acid, magnesium stearate, calcium stearate, sodium stearyl fumarate, sodium stearyl lactylate, zinc stearate, sodium stearate or lithium stearate, other solid state fatty acids such as oleic acid, lauric acid, palmitic acid, erucic acid, behenic acid, or derivatives (such as esters and salts), Amino acids such as leucine, isoleucine, lysine, valine, methionine, phenylalanine, aspartame or acesulfame K. In a preferred aspect of manufacturing this formulation the facilitating agent is added to the milled mixture of biologically active material and co-grinding matrix and further processed in another milling device such as Mechnofusion, Cyclomixing, or impact milling such as ball milling, jet milling, or milling using a high pressure homogeniser, or combinations thereof. In a highly preferred aspect the facilitating agent is added to the milling of the mixture of biologically active material and co-grinding matrix as some time before the end of the milling process.

In another preferred embodiment, diclofenac is milled with lactose monohydrate and alkyl sulfates. Preferably diclofenac is milled with lactose monohydrate and sodium lauryl sulfate. Preferably diclofenac is milled with lactose monohydrate and sodium octadecyl sulfate. In another preferred embodiment, Diclofenac is milled with lactose monohydrate, alkyl sulfates and another surfactant or polymers. Preferably diclofenac is milled with lactose monohydrate, sodium lauryl sulfate and polyether sulfates. Preferably diclofenac is milled with lactose monohydrate, sodium lauryl sulfate and polyethylene glycol 40 stearate. Preferably diclofenac is milled with lactose monohydrate, sodium lauryl sulfate and polyethylene glycol 100 stearate. Preferably diclofenac is milled with lactose monohydrate, sodium lauryl sulfate and a poloxamer. Preferably diclofenac is milled with lactose monohydrate, sodium lauryl sulfate and poloxamer 407. Preferably diclofenac is milled with lactose monohydrate, sodium lauryl sulfate and poloxamer 338. Preferably diclofenac is milled with lactose monohydrate, sodium lauryl sulfate and poloxamer 188. Preferably diclofenac is milled with lactose monohydrate, sodium lauryl sulfate and a solid polyethylene glycol. Preferably diclofenac is milled with lactose monohydrate, sodium lauryl sulfate and polyethylene glycol 6000. Preferably diclofenac is milled with lactose monohydrate, sodium lauryl sulfate and polyethylene glycol 3000. In another preferred embodiment, Diclofenac is milled with lactose monohydrate and polyether sulfates. Preferably diclofenac is milled with lactose monohydrate and polyethylene glycol 40 stearate. Preferably diclofenac is milled with lactose monohydrate and polyethylene glycol 100 stearate In another preferred embodiment diclofenac is milled with lactose monohydrate and polyvinyl-pyrrolidine. Preferably diclofenac is milled with lactose monohydrate and polyvinyl-pyrrolidone with an approximate molecular weight of 30,000-40,000. In another preferred embodiment, diclofenac is milled with lactose monohydrate and alkyl sulfonates. Preferably diclofenac is milled with lactose monohydrate and docusate sodium. In another preferred embodiment, diclofenac is milled with lactose monohydrate and a surfactant. Preferably diclofenac is milled with lactose monohydrate and lecithin. Preferably diclofenac is milled with lactose monohydrate and sodium n-lauroyl sarcosine. Preferably diclofenac is milled with lactose monohydrate and polyoxyethylene alkyl ether surfactants. Preferably diclofenac is milled with lactose monohydrate and PEG 6000. In another preferred formulation diclofenac is milled with lactose monohydrate and silica. Preferably diclofenac is milled with lactose monohydrate and Aerosil R972 fumed silica. In another preferred embodiment, diclofenac is milled with lactose monohydrate, tartaric acid and sodium lauryl sulfate. In another preferred embodiment, diclofenac is milled with lactose monohydrate, sodium bicarbonate and sodium lauryl sulfate. In another preferred embodiment, diclofenac is milled with lactose monohydrate, potassium bicarbonate and sodium lauryl sulfate. In another preferred embodiment, diclofenac is milled with mannitol and alkyl sulfates. Preferably diclofenac is milled with mannitol and sodium lauryl sulfate. Preferably diclofenac is milled with mannitol and sodium octadecyl sulfate. In another preferred embodiment, Diclofenac is milled with mannitol, alkyl sulfates and another surfactant or polymers. Preferably diclofenac is milled with mannitol, sodium lauryl sulfate and polyether sulfates. Preferably diclofenac is milled with mannitol, sodium lauryl sulfate and polyethylene glycol 40 stearate. Preferably diclofenac is milled with mannitol, sodium lauryl sulfate and polyethylene glycol 100 stearate. Preferably diclofenac is milled with mannitol, sodium lauryl sulfate and a poloxamer. Preferably diclofenac is milled with mannitol, sodium lauryl sulfate and poloxamer 407. Preferably diclofenac is milled with mannitol, sodium lauryl sulfate and poloxamer 338. Preferably diclofenac is milled with mannitol, sodium lauryl sulfate and poloxamer 188. Preferably diclofenac is milled with mannitol, sodium lauryl sulfate and a solid polyethylene glycol. Preferably diclofenac is milled with mannitol, sodium lauryl sulfate and polyethylene glycol 6000. Preferably diclofenac is milled with mannitol, sodium lauryl sulfate and polyethylene glycol 3000. In another preferred embodiment, Diclofenac is milled with mannitol and polyether sulfates. Preferably diclofenac is milled with mannitol and polyethylene glycol 40 stearate. Preferably diclofenac is milled with mannitol and polyethylene glycol 100 stearate In another preferred embodiment diclofenac is milled with mannitol and polyvinyl-pyrrolidine. Preferably diclofenac is milled with mannitol and polyvinyl-pyrrolidone with an approximate molecular weight of 30,000-40,000. In another preferred embodiment, diclofenac is milled with mannitol and alkyl sulfonates. Preferably diclofenac is milled with mannitol and docusate sodium. In another preferred embodiment, diclofenac is milled with mannitol and a surfactant. Preferably diclofenac is milled with mannitol and lecithin. Preferably diclofenac is milled with mannitol and sodium n-lauroyl sarcosine. Preferably diclofenac is milled with mannitol and polyoxyethylene alkyl ether surfactants. Preferably diclofenac is milled with mannitol and PEG 6000. In another preferred formulation diclofenac is milled with mannitol and silica. Preferably diclofenac is milled with mannitol and Aerosil R972 fumed silica. In another preferred embodiment, diclofenac is milled with mannitol, tartaric acid and sodium lauryl sulfate. In another preferred embodiment, diclofenac is milled with mannitol, sodium bicarbonate and sodium lauryl sulfate. In another preferred embodiment, diclofenac is milled with mannitol, potassium bicarbonate and sodium lauryl sulfate.

In a second aspect the invention comprises a biologically active material produced by the method described herein and composition comprising the biologically active material as described herein. Preferably, the average particle size, determined on a particle number basis, is equal to or less than a size selected from the group 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm and 100 nm. Preferably, the average particle size is equal to or greater than 25 nm. Preferably, the particles have a median particle size, determined on a particle volume basis, equal or less than a size selected from the group 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm and 100 nm. Preferably, the median particle size is equal to or greater than 25 nm. Preferably, the percentage of particles, on a particle volume basis, is selected from the group consisting of: 50%, 60%, 70%, 80%, 90%, 95% and 100% less than 2000 nm (%<2000 nm). Preferably, the percentage of particles, on a particle volume basis, is selected from the group consisting of: 50%, 60%, 70%, 80%, 90%, 95% and 100% less than 1000 nm (%<1000 nm). Preferably, the percentage of particles, on a particle volume basis, is selected from the group consisting of: 0%, 10%, 20%, 30%, 40%, 50%, 60%, 70%, 80%, 90%, 95% and 100% less than 500 nm (%<500 nm). Preferably, the percentage of particles, on a particle volume basis, is selected from the group consisting of: 0%, 10%, 20%, 30%, 40%, 50%, 60%, 70%, 80%, 90%, 95% and 100% less than 300 nm (%<300 nm). Preferably, the percentage of particles, on a particle volume basis, is selected from the group consisting of: 0%, 10%, 20%, 30%, 40%, 50%, 60%, 70%, 80%, 90%, 95% and 100% less than 200 nm (%<200 nm). Preferably, the Dx of the particle size distribution, as measured on a particle volume basis, is selected from the group consisting of less than or equal to 10,000 nm, 5000 nm, 3000 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm, and 100 nm; wherein x is greater than or equal to 90. Preferably, the crystallinity profile of the biologically active material is selected from the group consisting of: at least 50% of the biologically active material is crystalline, at least 60% of the biologically active material is crystalline, at least 70% of the biologically active material is crystalline, at least 75% of the biologically active material is crystalline, at least 85% of the biologically active material is crystalline, at least 90% of the biologically active material is crystalline, at least 95% of the biologically active material is crystalline and at least 98% of the biologically active material is crystalline. Preferably, the crystallinity profile of the biologically active material is substantially equal to the crystallinity profile of the biologically active material before the material was subject to the method described herein. Preferably, the amorphous content of the biologically active material is selected from the group consisting of: less than 50% of the biologically active material is amorphous, less than 40% of the biologically active material is amorphous, less than 30% of the biologically active material is amorphous, less than 25% of the biologically active material is amorphous, less than 15% of the biologically active material is amorphous, less than 10% of the biologically active material is amorphous, less than 5% of the biologically active material is amorphous and less than 2% of the biologically active material is amorphous. Preferably, the biologically active material has had no significant increase in amorphous content following subjecting the material to the method as described herein.

In one preferred embodiment, the invention comprises compositions comprising the biologically active ingredient together with a grinding matrix, a mixture of grinding matrix materials, milling aids, mixtures of milling aids, facilitating agents and/or mixtures of facilitating agents as described herein, in concentrations and ratios as described herein under the methods of the invention.

In a third aspect the invention comprises a pharmaceutical composition comprising a biologically active material produced by the method described herein and compositions described herein. Preferably, the invention comprises pharmaceutical compositions comprising the biologically active ingredient together with a grinding matrix, a mixture of grinding matrix materials, milling aids, mixtures of milling aids, facilitating agents and/or mixtures of facilitating agents as described herein, in concentrations and ratios as described herein under the methods of the invention. Preferably, the average particle size, determined on a particle number basis, is equal to or less than a size selected from the group 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm and 100 nm. Preferably, the average particle size is equal to or greater than 25 nm. Preferably, the particles have a median particle size, determined on a particle volume basis, equal or less than a size selected from the group 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm and 100 nm. Preferably, the median particle size is equal to or greater than 25 nm. Preferably, the percentage of particles, on a particle volume basis, is selected from the group consisting of: less than 2000 nm (%<2000 nm) is selected from the group consisting of: 50%, 60%, 70%, 80%, 90%, 95% and 100%; less than 1000 nm (%<1000 nm) is selected from the group consisting of: 50%, 60%, 70%, 80%, 90%, 95% and 100%; less than 500 nm (%<500 nm) is selected from the group 0%, 10%, 20%, 30%, 40%, 50%, 60%, 70%, 80%, 90%, 95% and 100%; less than 300 nm (%<300 nm) is selected from the group 0%, 10%, 20%, 30%, 40%, 50%, 60%, 70%, 80%, 90%, 95% and 100%; and less than 200 nm (%<200 nm) is selected from the group 0%, 10%, 20%, 30%, 40%, 50%, 60%, 70%, 80%, 90%, 95% and 100%. Preferably, the composition has a $T_{max}$ less than that of the equivalent conventional composition administered at the same dosage, wherein the composition comprises diclofenac. Preferably, the composition has a $C_{max}$ greater than that of the equivalent conventional composition administered at the same dosage, wherein the composition comprises diclofenac. Preferably, the composition has an AUC greater than that of the equivalent conventional composition administered at the same dosage, wherein the composition comprises diclofenac.

In a fourth aspect the invention comprises a method of treating a human in need of such treatment comprising the step of administering to the human an effective amount of a pharmaceutical composition as described herein.

In a fifth aspect, the invention comprises the use of a pharmaceutical composition as described herein in the manufacture of a medicament for the treatment of a human in need of such treatment.

In a sixth aspect the invention comprises a method for manufacturing a pharmaceutical composition as described herein comprising the step of combining a therapeutically effective amount of a biologically active material prepared by a method described herein or a composition as described herein, together with a pharmaceutically acceptable carrier to produce a pharmaceutically acceptable dosage form.

In a seventh aspect the invention comprises a method for manufacturing a veterinary product comprising the step of combining a therapeutically effective amount of the biologically active material prepared by a method as described herein or a composition as described herein, together with an acceptable excipient to produce a dosage form acceptable for veterinary use. In an eighth aspect the invention comprises a method for manufacturing of a pharmaceutical formulation comprising the step of combining an effective amount of the biologically active material prepared by a method described herein together with acceptable excipients to produce a formulation that can deliver a therapeutically effective amount of active to the pulmonary or nasal area. Such a formulation could be, but is not limited to a dry powder formulation for oral inhalation to the lungs or a formulation for nasal inhalation. Preferably the method for manufacturing such a formulation uses lactose, mannitol, sucrose, sorbitol, xylitol or other sugars or polyols as the co-grinding matrix together with surfactant such as, but not limited to lecithin, DPPC (dipalmitoyl phosphatidylcholine), PG (phosphatidylglycerol), dipalmitoyl phosphatidyl ethanolamine (DPPE), dipalmitoyl phosphatidylinositol (DPPI) or other phospholipid. The particle size of the material produced by the invention disclosed herein results in the materials being readily aerosolized and suitable for methods of delivery to a subject in need thereof, including pulmonary and nasal delivery methods.

While the method of the present invention has particular application in the preparation of poorly water-soluble biologically active materials, the scope of the invention is not limited thereto. For example, the method of the present invention enables production of highly water-soluble biologically active materials. Such materials may exhibit advantages over conventional materials by way of, for example, more rapid therapeutic action or lower dose. In contrast, wet grinding techniques utilizing water (or other comparably polar solvents) are incapable of being applied to such materials, as the particles dissolve appreciably in the solvent.

Other aspects and advantages of the invention will become apparent to those skilled in the art from a review of the ensuing description.

BRIEF DESCRIPTION OF THE DRAWINGS

FIG. 1A. Powder charge composition and particle size distribution of material milled in SPEX mill, examples A to S.

FIG. 1B. Powder charge composition and particle size distribution of material milled in SPEX mill, examples T to AL.

FIG. 1C. Powder charge composition and particle size distribution of material milled in SPEX mill, examples AM to BE.

FIG. 1D. Powder charge composition and particle size distribution of material milled in SPEX mill, examples BF to BX.

FIG. 1E. Powder charge composition and particle size distribution of material milled in SPEX mill, examples BY to CQ.

FIG. 1F. Powder charge composition and particle size distribution of material milled in SPEX mill, examples CR to DJ.

FIG. 1G. Powder charge composition and particle size distribution of material milled in SPEX mill, examples DK to EC.

FIG. 1H. The figure shows the X-Ray diffraction patterns: (A) after milling of Naproxen sodium in tartaric acid; (B) unmilled Naproxen sodium and (C) unmilled Naproxen acid.

FIG. 2A. Powder charge composition and particle size distribution of material milled in 110 mL HD01 Attritor mill, examples A to F.

FIG. 3A. Powder charge composition and particle size distribution of material containing a mixture of 2 matrices, milled in SPEX mill, examples A to E.

FIG. 4A. Powder charge composition and particle size distribution of material milled in 1 L HD01 Attritor mill, examples A to G.

FIG. 5A. Powder charge composition and particle size distribution of material milled in 750 mL 1S Attritor mill, examples A to F.

FIG. 6A. Powder charge composition and particle size distribution of material milled in ½ Gallon 1S Attritor mill, examples A to R.

FIG. 6B. Powder charge composition and particle size distribution of material milled in ½ Gallon 1S Attritor mill, examples S to AK.

FIG. 6C. Powder charge composition and particle size distribution of material milled in ½ Gallon 15 Attritor mill, examples AL to AU.

FIG. 7A. Powder charge composition and particle size distribution of Metaxalone milled in a variety of mills, examples A to O.

FIG. 8A. Powder charge composition and particle size distribution of material milled in HICOM mill, examples A to P.

FIG. 9A. Powder charge composition and particle size distribution of material milled in 1½ Gallon 1S Attritor mill, examples A to S.

FIG. 9B. Powder charge composition and particle size distribution of material milled in 1½ Gallon 1S Attritor mill, examples T to AL.

FIG. 10A. Powder charge composition and particle size distribution of material milled in a variety of large scale mills, examples A to F.

FIG. 11A. Powder charge composition and particle size distribution of Naproxen Acid milled in Mannitol in a ½ Gallon 1S Attritor mill, examples A to M.

FIG. 12A. Powder charge composition and particle size distribution of Naproxen Acid milled in SPEX mill and particle size distribution after filtration, examples A to L.

DETAILED DESCRIPTION OF THE INVENTION

General

Those skilled in the art will appreciate that the invention described herein is susceptible to variations and modifications other than those specifically described. It is to be understood that the invention includes all such variations and modifications. The invention also includes all of the steps, features, compositions and materials referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

The invention described herein may include one or more ranges of values (e.g. size, concentration etc). A range of values will be understood to include all values within the range, including the values defining the range, and values adjacent to the range that lead to the same or substantially the same outcome as the values immediately adjacent to that value which defines the boundary to the range.

The entire disclosures of all publications (including patents, patent applications, journal articles, laboratory manuals, books, or other documents) cited herein are hereby incorporated by reference. Inclusion does not constitute an admission is made that any of the references constitute prior art or are part of the common general knowledge of those working in the field to which this invention relates.

Throughout this specification, unless the context requires otherwise, the word "comprise" or variations, such as "comprises" or "comprising" will be understood to imply the inclusion of a stated integer, or group of integers, but not the exclusion of any other integers or group of integers. It is also noted that in this disclosure, and particularly in the claims and/or paragraphs, terms such as "comprises", "comprised", "comprising" and the like can have the meaning attributed to it in US Patent law; e.g., they can mean "includes", "included", "including", and the like.

"Therapeutically effective amount" as used herein with respect to methods of treatment and in particular drug dosage, shall mean that dosage that provides the specific pharmacological response for which the drug is administered in a significant number of subjects in need of such treatment. It is emphasized that "therapeutically effective amount," administered to a particular subject in a particular instance will not always be effective in treating the diseases described herein, even though such dosage is deemed a "therapeutically effective amount" by those skilled in the art. It is to be further understood that drug dosages are, in particular instances, measured as oral dosages, or with reference to drug levels as measured in blood.

The term "inhibit" is defined to include its generally accepted meaning which includes prohibiting, preventing, restraining, and lowering, stopping, or reversing progression or severity, and such action on a resultant symptom. As such the present invention includes both medical therapeutic and prophylactic administration, as appropriate.

The term "biologically active material" is defined to mean a biologically active compound or a substance which comprises a biologically active compound. In this definition, a compound is generally taken to mean a distinct chemical entity where a chemical formula or formulas can be used to describe the substance. Such compounds would generally, but not necessarily be identified in the literature by a unique classification system such as a CAS number. Some compounds may be more complex and have a mixed chemical structure. For such compounds they may only have an empirical formula or be qualitatively identified. A compound would generally be a pure material, although it would be expected that up to 10%, 20%, 30%, 40%, 50%, 60%, 70%, 80%, 90% of the substance could be other impurities and the like. Examples of biologically active compounds are, but not limited to, pharmaceutical actives, and analogs, homologs and first order derivatives thereof. A substance that contains a biologically active compound is any substance which has as one of its components a biologically active compound. Examples of substances containing biologically active compounds are, but not limited to, pharmaceutical formulations and products.

Any of the terms, "biological(ly) active", "active", "active material" shall have the same meaning as biologically active material.

The term "grinding matrix" is defined as any inert substance that a biologically active material can or is combined with and milled. The terms "co-grinding matrix" and "matrix" are interchangeable with "grinding matrix".

Particle Size

There are a wide range of techniques that can be utilized to characterize the particle size of a material. Those skilled in the art also understand that almost all these techniques do not physically measure the actually particle size, as one might measure something with a ruler, but measure a physical phenomena which is interpreted to indicate a particle size. As part of the interpretation process some assumptions need to be made to enable mathematical calculations to be made. These assumptions deliver results such as an equivalent spherical particle size, or a hydrodynamic radius.

Amongst these various methods, two types of measurements are most commonly used. Photon correlation spectroscopy (PCS), also known as 'dynamic light scattering' (DLS) is commonly used to measure particles with a size less than 10 micron. Typically this measurement yields an equivalent hydrodynamic radius often expressed as the average size of a number distribution. The other common particle size measurement is laser diffraction which is commonly used to measure particle size from 100 nm to 2000 micron. This technique calculates a volume distribution of equivalent spherical particles that can be expressed using descriptors such as the median particle size or the % of particles under a given size.

Those skilled in the art recognize that different characterization techniques such as photon correlation spectroscopy and laser diffraction measure different properties of a particle ensemble. As a result multiple techniques will give multiple answers to the question, "what is the particle size." In theory one could convert and compare the various parameters each technique measures, however, for real world particle systems this is not practical. As a result the particle size used to describe this invention will be given as two different sets of values that each relate to these two common measurement techniques, such that measurements could be made with either technique and then evaluated against the description of this invention.

For measurements made using a photo correlation spectroscopy instrument, or an equivalent method known in the art, the term "number average particle size" is defined as the average particle diameter as determined on a number basis.

For measurements made using a laser diffraction instrument, or an equivalent method known in the art, the term "median particle size" is defined as the median particle diameter as determined on an equivalent spherical particle volume basis. Where the term median is used, it is understood to describe the particle size that divides the population in half such that 50% of the population is greater than or less than this size. The median particle size is often written as D50, D(0.50) or D[0.5] or similar. As used herein D50, D(0.50) or D[0.5] or similar shall be taken to mean 'median particle size'.

The term "Dx of the particle size distribution" refers to the xth percentile of the distribution; thus, D90 refers to the $90^{th}$ percentile, D95 refers to the $95^{th}$ percentile, and so forth. Taking D90 as an example this can often be written as, D(0.90) or D[0.9] or similar. With respect to the median particle size and Dx an upper case D or lowercase d are interchangeable and have the same meaning. Another commonly used way of describing a particle size distribution measured by laser diffraction, or an equivalent method known in the art, is to describe what % of a distribution is under or over a nominated size. The term "percentage less than" also written as "%<" is defined as the percentage, by volume, of a particle size distribution under a nominated size—for example the %<1000 nm. The term "percentage greater than" also written as "%>" is defined as the percentage, by volume, of a particle size distribution over a nominated size—for example the %>1000 nm.

The particle size used to describe this invention should be taken to mean the particle size as measured at or shortly before the time of use. For example, the particle size is measured 2 months after the material is subject to the milling method of this invention. In a preferred form, the particle size is measured at a time selected from the group consisting of: 1 day after milling, 2 days after milling, 5 days after milling, 1 month after milling, 2 months after milling, 3 months after milling, 4 months after milling, 5 months after milling, 6 months after milling, 1 year after milling, 2 years after milling, 5 years after milling.

For many of the materials subject to the methods of this invention the particle size can be easily measured. Where the active material has poor water solubility and the matrix it is milled in has good water solubility the powder can simply be dispersed in an aqueous solvent. In this scenario the matrix dissolves leaving the active material dispersed in the solvent. This suspension can then be measured by techniques such as PCS or laser diffraction.

Suitable methods to measure an accurate particle size where the active material has substantive aqueous solubility or the matrix has low solubility in a water based dispersant are outlined below.

1. In the circumstance where insoluble matrix such as microcrystalline cellulose prevents the measurement of the active material separation techniques such as filtration or centrifugation could be used to separate the insoluble matrix from the active material particles. Other ancillary techniques would also be required to determine if any active material was removed by the separation technique so that this could be taken into account.
2. In the case where the active material is too soluble in water other solvents could be evaluated for the measurement of particle size. Where a solvent could be found that active material is poorly soluble in but is a good solvent for the matrix a measurement would be relatively straight forward. If such a solvent is difficult to find another approach would be to measure the ensemble of matrix and active material in a solvent (such as iso-octane) which both are insoluble in. Then the powder would be measured in another solvent where the active material is soluble but the matrix is not. Thus with a measurement of the matrix particle size and a measurement of the size of the matrix and active material together an understanding of the active material particle size can be obtained.
3. In some circumstances image analysis could be used to obtain information about the particle size distribution of the active material. Suitable image measurement techniques might include transmission electron microscopy (TEM), scanning electron microscopy (SEM), optical microscopy and confocal microscopy. In addition to these standard techniques some additional technique would be required to be used in parallel to differentiate the active material and matrix particles. Depending on the chemical makeup of the materials involved possible techniques could be elemental analysis, raman spectroscopy, FTIR spectroscopy or fluorescence spectroscopy.

Other Definitions

Throughout this specification, unless the context requires otherwise, the phrase "dry mill" or variations, such as "dry milling", should be understood to refer to milling in at least the substantial absence of liquids. If liquids are present, they are present in such amounts that the contents of the mill retain the characteristics of a dry powder.

"Flowable" means a powder having physical characteristics rendering it suitable for further processing using typical equipment used for the manufacture of pharmaceutical compositions and formulations.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

The term "millable" means that the grinding matrix is capable of being physically degraded under the dry milling conditions of the method of the invention. In one embodiment of the invention, the milled grinding matrix is of a comparable particle size to the biologically active material. In another embodiment of the invention the particle size of the matrix is substantially reduced but not as small as the biologically active material Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Specific

In one embodiment, the present invention is directed to a method for producing a composition, comprising the steps of: dry milling a solid biologically active material and a millable grinding matrix in a mill comprising a plurality of milling bodies, for a time period sufficient to produce particles of the biologically active material dispersed in an at least partially milled grinding material.

The mixture of active material and matrix may then be separated from the milling bodies and removed from the mill.

In one aspect the mixture of active material and matrix is then further processed. In another aspect, the grinding matrix is separated from the particles of biologically active material. In a further aspect, at least a portion of the milled grinding matrix is separated from the particulate biologically active material.

The milling bodies are essentially resistant to fracture and erosion in the dry milling process. The quantity of the grinding matrix relative to the quantity of biologically active material in particulate form, and the extent of milling of the grinding matrix, is sufficient to inhibit re-agglomeration of the particles of the active material.

The present invention also relates to biologically active materials produced by said methods, to medicaments produced using said biologically active materials and to methods of treatment of an animal, including man, using a therapeutically effective amount of said biologically active materials administered by way of said medicaments.

Commercial Scale

The present invention is directed to the unexpected finding that particles of a biologically active material can be produced by dry milling processes as described herein at commercial scale. In one surprising aspect the particle size produced by the process is equal to or less than 2000 nm. In another surprising aspect the particle size produced by the process is equal to or less than 1000 nm. This can result in a more efficient and cost effective process.

One of the key goals of reducing manufacturing costs is the encapsulation of the nanoparticles into materials that do not have to be removed. This enables a simple manufacturing process where conventional formulation technologies can be used to progress the matrix encapsulated nanoparticles directly to a final product. In order to do this the materials used within the matrix must be acceptable to industry regulators. In some cases materials may be acceptable for use but only in limited quantities. Another aspect of matrix choice is functionality. Some matrices that produce good encapsulated nanoparticles may be acceptable from a safety perspective but these materials may make manufacture of a dosage form such as tablet limited.

Improving the Dissolution Profile

The process results in the biologically active material having an improved dissolution profile. An improved dissolution profile has significant advantages including the improvement of bioavailability of the biologically active material in vivo. Preferably, the improved dissolution profile is observed in vitro. Alternatively, the improved dissolution profile is observed in vivo by the observation of an improved bioavailability profile. Standard methods for determining the dissolution profile of a material in vitro are available in the art. A suitable method to determine an improved dissolution profile in vitro may include determining the concentration of the sample material in a solution over a period of time and comparing the results from the sample material to a control sample. An observation that peak solution concentration for the sample material was achieved in less time than the control sample would indicate (assuming it is statistically significant), that the sample material has an improved dissolution profile. The measurement sample is herein defined as the mixture of biologically active material with grinding matrix and/or other additives that has been subject to the processes of the invention described here. Herein a control sample is defined as a physical mixture (not subject to the processes described in this invention) of the components in the measurement sample with the same relative proportions of active, matrix and/or additive as the measurement sample. For the purposes of the dissolution testing a prototype formulation of the measurement sample could also be used. In this case the control sample would be formulated in the same way. Standard methods for determining the improved dissolution profile of a material in vivo are available in the art. A suitable method to determine an improved dissolution profile in a human may be after delivering the dose to measure the rate of active material absorption by measuring the plasma concentration of the sample compound over a period of time and comparing the results from the sample compound to a control. An observation that peak plasma concentration for the sample compound was achieved in less time than the control would indicate (assuming it is statistically significant) that the sample compound has improved bioavailability and an improved dissolution profile. Preferably, the improved dissolution profile is observed at a relevant gastrointestinal pH, when it is observed in vitro. Preferably, the improved dissolution profile is observed at a pH which is favourable at indicating improvements in dissolution when comparing the measurement sample to the control compound. Suitable methods for quantifying the concentration of a compound in an in vitro sample or an in vivo sample are widely available in the art. Suitable methods could include the use of spectroscopy or radioisotope labeling. In one preferred embodiment the method of quantification of dissolution is determined in a solution with a pH selected from the group consisting of: pH 1, pH 2, pH 3, pH 4, pH 5, pH 6, pH 7, pH 7.3, pH 7.4, pH 8, pH 9, pH 10, pH 11, pH 12, pH 13, pH 14 or a pH with 0.5 of a pH unit of any of this group.

Crystallization Profile

Methods for determining the crystallinity profile of the biologically active material are widely available in the art. Suitable methods may include X-ray diffraction, differential scanning calorimetry, raman or IR spectroscopy.

Amorphicity Profile

Methods for determining the amorphous content of the biologically active material are widely available in the art. Suitable methods may include X-ray diffraction, differential scanning calorimetry, raman or IR spectroscopy.

Grinding Matrix

As will be described subsequently, selection of an appropriate grinding matrix affords particular advantageous applications of the method of the present invention.

A highly advantageous application of the method of the invention is the use of a water-soluble grinding matrix in conjunction with a poorly water-soluble biologically active material. This affords at least two advantages. The first being when the powder containing the biologically active material is placed into water—such as the ingestion of the powder as part of an oral medication—the matrix dissolves, releasing the particulate active material such that there is maximum surface area exposed to solution, thereby allowing a rapid dissolution of the active compound. The second key advantage is the ability, if required, to remove or partially remove the matrix prior to further processing or formulation.

Another advantageous application of the method of the invention is the use of a water-insoluble grinding matrix, particularly in the area of agricultural use, when a biologically active material such as a fungicide is commonly delivered as part of a dry powder or a suspension. The presence of a water insoluble matrix will afford benefits such as increased rain fastness.

Without wishing to be bound by theory, it is believed that the physical degradation (including but not limited to particle size reduction) of the millable grinding matrix affords the advantage of the invention, by acting as a more effective diluent than grinding matrix of a larger particle size.

Again, as will be described subsequently, a highly advantageous aspect of the present invention is that certain grinding matrixes appropriate for use in the method of the invention are also appropriate for use in a medicament. The present invention encompasses methods for the production of a medicament incorporating both the biologically active material and the grinding matrix or in some cases the biologically active material and a portion of the grinding matrix, medicaments so produced, and methods of treatment of an animal, including man, using a therapeutically effective amount of said biologically active materials by way of said medicaments.

Analogously, as will be described subsequently, a highly advantageous aspect of the present invention is that certain grinding matrixes appropriate for use in the method of the invention are also appropriate for use in a carrier for an agricultural chemical, such as a pesticide, fungicide, or herbicide. The present invention encompasses methods for the production of an agricultural chemical composition incorporating both the biologically active material in particulate form and the grinding matrix, or in some cases the biologically active material, and a portion of the grinding matrix, and agricultural chemical compositions so produced. The medicament may include only the biologically active material together with the milled grinding matrix or, more preferably, the biologically active material and milled grinding matrix may be combined with one or more pharmaceutically acceptable carriers, as well as any desired excipients or other like agents commonly used in the preparation of medicaments.

Analogously, the agricultural chemical composition may include only the biologically active material together with the milled grinding matrix or, more preferably, the biologically active materials and milled grinding matrix may be combined with one or more carriers, as well as any desired excipients or other like agents commonly used in the preparation of agricultural chemical compositions.

In one particular form of the invention, the grinding matrix is both appropriate for use in a medicament and readily separable from the biologically active material by methods not dependent on particle size. Such grinding matrixes are described in the following detailed description of the invention. Such grinding matrixes are highly advantageous in that they afford significant flexibility in the extent to which the grinding matrix may be incorporated with the biologically active material into a medicament.

In a highly preferred form, the grinding matrix is harder than the biologically active material, and is thus capable of reducing the particle size of the active material under the dry milling conditions of the invention. Again without wishing to be bound by theory, under these circumstances it is believed that the millable grinding matrix affords the advantage of the present invention through a second route, with the smaller particles of grinding matrix produced under the dry milling conditions enabling greater interaction with the biologically active material. The quantity of the grinding matrix relative to the quantity of biologically active material, and the extent of physical degradation of the grinding matrix, is sufficient to inhibit re-agglomeration of the particles of the active material Preferably, the quantity of the grinding matrix relative to the quantity of biologically active material, and the extent of physical degradation of the grinding matrix, is sufficient to inhibit re-agglomeration of the particles of the active material in nanoparticulate form. The grinding matrix is not generally selected to be chemically reactive with the biologically active material under the milling conditions of the invention, excepting for example, where the matrix is deliberately chosen to undergo a mechanico-chemical reaction. Such a reaction might be the conversion of a free base or acid to a salt or vice versa.

As stated above, the method of the present invention requires the grinding matrix to be milled with the biologically active material; that is, the grinding matrix will physically degrade under the dry milling conditions of the invention to facilitate the formation and retention of particulates of the biologically active material with reduced particle size. The precise extent of degradation required will depend on certain properties of the grinding matrix and the biologically active material, the ratio of biologically active material to grinding matrix, and the particle size distribution of the particles comprising the biologically active material.

The physical properties of the grinding matrix necessary to achieve the requisite degradation are dependent on the precise milling conditions. For example, a harder grinding matrix may degrade to a sufficient extent provided it is subjected to more vigorous dry milling conditions. Physical properties of the grinding matrix relevant to the extent that the agent will degrade under dry milling conditions include hardness, friability, as measured by indicia such as hardness, fracture toughness and brittleness index.

A low hardness (typically a Mohs Hardness less than 7) of the biologically active material is desirable to ensure fracture of the particles during processing, so that composite microstructures develop during milling. Preferably, the hardness is less than 3 as determined using the Mohs Hardness scale.

Preferably, the grinding matrix is of low abrasivity. Low abrasivity is desirable to minimise contamination of the mixture of the biologically active material in the grinding matrix by the milling bodies and/or the milling chamber of the media mill. An indirect indication of the abrasivity can be obtained by measuring the level of milling-based contaminants.

Preferably, the grinding matrix has a low tendency to agglomerate during dry milling. While it is difficult to objectively quantify the tendency to agglomerate during milling, it is possible to obtain a subjective measure by observing the level of "caking" of the grinding matrix on the milling bodies and the milling chamber of the media mill as dry milling progresses.

The grinding matrix may be an inorganic or organic substance.

In one embodiment, the grinding matrix is selected from the following, either as a single substance or a combination of two or more substances: Polyols (sugar alcohols) for example (but not limited to) mannitol, sorbitol, isomalt, xylitol, maltitol, lactitol, erythritol, arabitol, ribitol, monosaccharides for example (but not limited to) glucose, fructose, mannose, galactose, disaccharides and trisaccharides for example (but not limited to) anhydrous lactose, lactose monohydrate, sucrose, maltose, trehalose, polysaccharides for example (but not limited to) maltodextrins, dextrin, Inulin, dextrates, polydextrose, other carbohydrates for example (but not limited to) starch, wheat flour, corn flour, rice flour, rice starch, tapioca flour, tapioca starch, potato flour, potato starch, other flours and starches, soy flour, soy meal or other soy products, cellulose, microcrystalline cellulose, microcrystalline cellulose based co blended excipients, chemically modified excipients such as pregelatinized (or partially) starch, modified celluloses such as HPMC, CMC, HPC, enteric polymer coatings such as hypromellose phthalate, cellulose acetate phthalate (Aquacoat®), polyvinyl acetate phthalate (Sureteric®), hypromellose acetate succinate (AQOAT®), and polymethacrylates (Eudragit® and Acryl-EZE®), Milk products for example (but not limited to) milk powder, skim milk powders, other milk solids and derivatives, other functional Excipients, organic acids for example (but not limited to) citric acid, tartaric acid, malic acid, maleic acid fumaric acid, ascorbic acid, succinic acid, the conjugate salt of organic acids for example (but not limited to) sodium citrate, sodium tartrate, sodium malate, sodium ascorbate, potassium citrate, potassium tartrate, potassium malate, potassium ascorbate, inorganics such as sodium carbonate, potassium carbonate, magnesium carbonate, sodium bicarbonate, potassium bicarbonate and calcium carbonate. dibasic calcium phosphate, tribasic calcium phosphate, sodium sulfate, sodium chloride, sodium metabisulphite, sodium thiosulfate, ammonium chloride, Glauber's salt, ammonium carbonate, sodium bisulfate, magnesium sulfate, potash alum, potassium chloride, sodium hydrogen sulfate, sodium hydroxide, crystalline hydroxides, hydrogen carbonates, hydrogen carbonates of pharmaceutical acceptable alkali metals, such as but not limited by, sodium, potassium, lithium, calcium, and barium, ammonium salts (or salts of volatile amines), for example (but not limited to) ammonium chloride, methylamine hydrochloride, ammonium bromide, other inorganics for example (but not limited to), thermal silica, chalk, mica, silica, alumina, titanium dioxide, talc, kaolin, bentonite, hectorite, magnesium trisilicate, other clay or clay derivatives or aluminium silicates, a surfactant for example (but not limited to) sodium lauryl sulfate, sodium stearyl sulfate, sodium cetyl sulfate, sodium cetostearyl sulfate, sodium docusate, sodium deoxycholate, N-lauroylsarcosine sodium salt, glyceryl monostearate, glycerol distearate glyceryl palmitostearate, glyceryl behenate, glyceryl caprylate, glyceryl oleate, benzalkonium chloride, CTAB, CTAC, Cetrimide, cetylpyridinium chloride, cetylpyridinium bromide, benzethonium chloride, PEG 40 stearate, PEG 100 stearate, poloxamer 188, poloxamer 407, poloxamer 338, polyoxyl 2 stearyl ether, polyoxyl 100 stearyl ether, polyoxyl 20 stearyl ether, polyoxyl 10 stearyl ether, polyoxyl 20 cetyl ether, polysorbate 20, polysorbate 40, polysorbate 60, polysorbate 61, polysorbate 65, polysorbate 80, polyoxyl 35 castor oil, polyoxyl 40 castor oil, polyoxyl 60 castor oil, polyoxyl 100 castor oil, polyoxyl 200 castor oil, polyoxyl 40 hydrogenated castor oil, polyoxyl 60 hydrogenated castor oil, polyoxyl 100 hydrogenated castor oil, polyoxyl 200 hydrogenated castor oil, cetostearyl alcohol, macrogel 15 hydroxystearate, sorbitan monopalmitate, sorbitan monostearate, sorbitan trioleate, Sucrose Palmitate, Sucrose Stearate, Sucrose Distearate, Sucrose laurate, Glycocholic acid, sodium Glycholate, Cholic Acid, Soidum Cholate, Sodium Deoxycholate, Deoxycholic acid, Sodium taurocholate, taurocholic acid, Sodium taurodeoxycholate, taurodeoxycholic acid, soy lecithin, phosphatidylcholine, phosphatidylethanolamine, phosphatidylserine, phosphatidylinositol, PEG4000, PEG6000, PEG8000, PEG10000, PEG20000, alkyl naphthalene sulfonate condensate/Lignosulfonate blend, Calcium Dodecylbenzene Sulfonate, Sodium Dodecylbenzene Sulfonate, Diisopropyl naphthaenesulphonate, erythritol distearate, Naphthalene Sulfonate Formaldehyde Condensate, nonylphenol ethoxylate (poe-30), Tristyrylphenol Ethoxylate, Polyoxyethylene (15) tallowalkylamines, sodium alkyl naphthalene sulfonate, sodium alkyl naphthalene sulfonate condensate, sodium alkylbenzene sulfonate, sodium isopropyl naphthalene sulfonate, Sodium Methyl Naphthalene Formaldehyde Sulfonate, sodium n-butyl naphthalene sulfonate, tridecyl alcohol ethoxylate (poe-18), Triethanolamine isodecanol phosphate ester, Triethanolamine tristyrylphosphate ester, Tristyrylphenol Ethoxylate Sulfate, Bis(2-hydroxyethyl)tallowalkylamines.

In a preferred embodiment, the grinding matrix is a matrix that is considered GRAS (generally regarded as safe) by persons skilled in the pharmaceutical arts.

In another preferred aspect a combination of two or more suitable matrices, such as those listed above, can be used as the grinding matrix to provide improved properties such as the reduction of caking, and greater improvement of the dissolution profile. Combination matrices may also be advantageous when the matrices have different solubility's allowing the removal or partial removal of one matrix, while leaving the other or part of the other to provide encapsulation or partial encapsulation of the biologically active material.

Another highly preferred aspect of the method is the inclusion of a suitable milling aid in the matrix to improve milling performance. Improvements to milling performance would be things such as, but not limited to, a reduction in caking or higher recovery of powder from the mill. Examples of suitable milling aids include surfactants, polymers and inorganics such as silica (including colloidal silica), aluminium silicates and clays.

There are a wide range of surfactants that will make suitable milling aids. The highly preferred form is where the surfactant is a solid, or can be manufactured into a solid. Preferably, the surfactant is selected from the group consisting of: polyoxyethylene alkyl ethers, polyoxyethylene stearates, polyethylene glycols (PEG), poloxamers, poloxamines, sarcosine based surfactants, polysorbates, aliphatic alcohols, alkyl and aryl sulfates, alkyl and aryl polyether sulfonates and other sulfate surfactants, trimethyl ammonium based surfactants, lecithin and other phospholipids, bile salts, polyoxyethylene castor oil derivatives, polyoxyethylene sorbitan fatty acid esters, Sorbitan fatty acid esters, Sucrose fatty acid esters, alkyl glucopyranosides, alkyl maltopyranosides, glycerol fatty acid esters, Alkyl Benzene Sulphonic Acids, Alkyl Ether Carboxylic Acids, Alkyl and aryl Phosphate esters, Alkyl and aryl Sulphate esters, Alkyl and aryl Sulphonic acids, Alkyl Phenol Phosphates esters, Alkyl Phenol Sulphates esters, Alkyl and Aryl Phosphates, Alkyl Polysaccharides, Alkylamine Ethoxylates, Alkyl-Naphthalene Sulphonates formaldehyde condensates, Sulfosuccinates, lignosulfonates, Ceto-Oleyl Alcohol Ethoxylates, Condensed Naphthalene Sulphonates, Dialkyl and Alkyl Naphthalene Sulphonates, Di-alkyl Sulphosuccinates, Ethoxylated nonylphenols, Ethylene Glycol Esters, Fatty Alcohol Alkoxylates, Hydrogenated tallowalkylamines, Mono-alkyl Sulphosuccinamates, Nonyl Phenol Ethoxylates, Sodium Oleyl N-methyl Taurate, Tallowalkylamines, linear and branched dodecylbenzene sulfonic acids Preferably, the surfactant is selected from the group consisting of: sodium lauryl sulfate, sodium stearyl sulfate, sodium cetyl sulfate, sodium cetostearyl sulfate, sodium docusate, sodium deoxycholate, N-lauroylsarcosine sodium salt, glyceryl monostearate, glycerol distearate glyceryl palmitostearate, glyceryl behenate, glyceryl caprylate, glyceryl oleate, benzalkonium chloride, CTAB, CTAC, Cetrimide, cetylpyridinium chloride, cetylpyridinium bromide, benzethonium chloride, PEG 40 stearate, PEG 100 stearate, poloxamer 188, poloxamer 338, poloxamer 407 polyoxyl 2 stearyl ether, polyoxyl 100 stearyl ether, polyoxyl 20 stearyl ether, polyoxyl 10 stearyl ether, polyoxyl 20 cetyl ether, polysorbate 20, polysorbate 40, polysorbate 60, polysorbate 61, polysorbate 65, polysorbate 80, polyoxyl 35 castor oil, polyoxyl 40 castor oil, polyoxyl 60 castor oil, polyoxyl 100 castor oil, polyoxyl 200 castor oil, polyoxyl 40 hydrogenated castor oil, polyoxyl 60 hydrogenated castor oil, polyoxyl 100 hydrogenated castor oil, polyoxyl 200 hydrogenated castor oil, cetostearyl alcohol, macrogel 15 hydroxystearate, sorbitan monopalmitate, sorbitan monostearate, sorbitan trioleate, Sucrose Palmitate, Sucrose Stearate, Sucrose Distearate, Sucrose laurate, Glycocholic acid, sodium Glycholate, Cholic Acid, Sodium Cholate, Sodium Deoxycholate, Deoxycholic acid, Sodium taurocholate, taurocholic acid, Sodium taurodeoxycholate, taurodeoxycholic acid, soy lecithin, phosphatidylcholine, phosphatidylethanolamine, phosphatidylserine, phosphatidylinositol, PEG4000, PEG6000, PEG8000, PEG10000, PEG20000, alkyl naphthalene sulfonate condensate/Lignosulfonate blend, Calcium Dodecylbenzene Sulfonate, Sodium Dodecylbenzene Sulfonate, Diisopropyl naphthaenesulphonate, erythritol distearate, Naphthalene Sulfonate Formaldehyde Condensate, nonylphenol ethoxylate (poe-30), Tristyrylphenol Ethoxylate, Polyoxyethylene (15) tallowalkylamines, sodium alkyl naphthalene sulfonate, sodium alkyl naphthalene sulfonate condensate, sodium alkylbenzene sulfonate, sodium isopropyl naphthalene sulfonate, Sodium Methyl Naphthalene Formaldehyde Sulfonate, sodium n-butyl naphthalene sulfonate, tridecyl alcohol ethoxylate (poe-18), Triethanolamine isodecanol phosphate ester, Triethanolamine tristyrylphosphate ester, Tristyrylphenol Ethoxylate Sulfate, Bis(2-hydroxyethyl)tallowalkylamines.

Preferably the polymer is selected from the list of: polyvinylpyrrolidones (PVP), polyvinylalcohol, Acrylic acid based polymers and copolymers of acrylic acid Preferably, the milling aid has a concentration selected from the group consisting of: 0.1-10% w/w, 0.1-5% w/w, 0.1-2.5% w/w, of 0.1-2% w/w, 0.1-1%, 0.5-5% w/w, 0.5-3% w/w, 0.5-2% w/w, 0.5-1.5%, 0.5-1 w/w, of 0.75-1.25% w/w, 0.75-1% and 1% w/w.

Milling Bodies

In the method of the present invention, the milling bodies are preferably chemically inert and rigid. The term "chemically-inert", as used herein, means that the milling bodies do not react chemically with the biologically active material or the grinding matrix.

As described above, the milling bodies are essentially resistant to fracture and erosion in the milling process.

The milling bodies are desirably provided in the form of bodies which may have any of a variety of smooth, regular shapes, flat or curved surfaces, and lacking sharp or raised edges. For example, suitable milling bodies can be in the form of bodies having ellipsoidal, ovoid, spherical or right cylindrical shapes. Preferably, the milling bodies are provided in the form of one or more of beads, balls, spheres, rods, right cylinders, drums or radius-end right cylinders (i.e., right cylinders having hemispherical bases with the same radius as the cylinder).

Depending on the nature of the biologically active material and the grinding matrix, the milling media bodies desirably have an effective mean particle diameter (i.e. "particle size") between about 0.1 and 30 mm, more preferably between about 1 and about 15 mm, still more preferably between about 3 and 10 mm.

The milling bodies may comprise various substances such as ceramic, glass, metal or polymeric compositions, in a particulate form. Suitable metal milling bodies are typically spherical and generally have good hardness (i.e. RHC 60-70), roundness, high wear resistance, and narrow size distribution and can include, for example, balls fabricated from type 52100 chrome steel, type 316 or 440C stainless steel or type 1065 high carbon steel.

Preferred ceramics, for example, can be selected from a wide array of ceramics desirably having sufficient hardness and resistance to fracture to enable them to avoid being chipped or crushed during milling and also having sufficiently high density. Suitable densities for milling media can range from about 1 to 15 g/cm$^{3'}$, preferably from about 1 to 8 g/cm$^3$. Preferred ceramics can be selected from steatite, aluminum oxide, zirconium oxide, zirconia-silica, yttria-stabilized zirconium oxide, magnesia-stabilized zirconium oxide, silicon nitride, silicon carbide, cobalt-stabilized tungsten carbide, and the like, as well as mixtures thereof.

Preferred glass milling media are spherical (e.g. beads), have a narrow size distribution, are durable, and include, for example, lead-free soda lime glass and borosilicate glass. Polymeric milling media are preferably substantially spherical and can be selected from a wide array of polymeric resins having sufficient hardness and friability to enable them to avoid being chipped or crushed during milling, abrasion-resistance to minimize attrition resulting in contamination of the product, and freedom from impurities such as metals, solvents, and residual monomers.

Preferred polymeric resins, for example, can be selected from crosslinked polystyrenes, such as polystyrene crosslinked with divinylbenzene, styrene copolymers, polyacrylates such as polymethylmethacrylate, polycarbonates, polyacetals, vinyl chloride polymers and copolymers, polyurethanes, polyamides, high density polyethylenes, polypropylenes, and the like. The use of polymeric milling media to grind materials down to a very small particle size (as opposed to mechanochemical synthesis) is disclosed, for example, in U.S. Pat. Nos. 5,478,705 and 5,500,331. Polymeric resins typically can have densities ranging from about 0.8 to 3.0 g/cm$^3$. Higher density polymeric resins are preferred. Alternatively, the milling media can be composite particles comprising dense core particles having a polymeric resin adhered thereon. Core particles can be selected from substances known to be useful as milling media, for example, glass, alumina, zirconia silica, zirconium oxide, stainless steel, and the like. Preferred core substances have densities greater than about 2.5 g/cm$^3$.

In one embodiment of the invention, the milling media are formed from a ferromagnetic substance, thereby facilitating removal of contaminants arising from wear of the milling media by the use of magnetic separation techniques.

Each type of milling body has its own advantages. For example, metals have the highest specific gravities, which increase grinding efficiency due to increased impact energy. Metal costs range from low to high, but metal contamination of final product can be an issue. Glasses are advantageous from the standpoint of low cost and the availability of small bead sizes as low as 0.004 mm. However, the specific gravity of glasses is lower than other media and significantly more milling time is required. Finally, ceramics are advantageous from the standpoint of low wear and contamination, ease of cleaning, and high hardness.

Dry Milling

In the dry milling process of the present invention, the biologically active material and grinding matrix, in the form of crystals, powders, or the like, are combined in suitable proportions with the plurality of milling bodies in a milling chamber that is mechanically agitated (i.e. with or without stirring) for a predetermined period of time at a predetermined intensity of agitation. Typically, a milling apparatus is used to impart motion to the milling bodies by the external application of agitation, whereby various translational, rotational or inversion motions or combinations thereof are applied to the milling chamber and its contents, or by the internal application of agitation through a rotating shaft terminating in a blade, propeller, impeller or paddle or by a combination of both actions.

During milling, motion imparted to the milling bodies can result in application of shearing forces as well as multiple impacts or collisions having significant intensity between milling bodies and particles of the biologically active material and grinding matrix. The nature and intensity of the forces applied by the milling bodies to the biologically active material and the grinding matrix is influenced by a wide variety of processing parameters including: the type of milling apparatus; the intensity of the forces generated, the kinematic aspects of the process; the size, density, shape, and composition of the milling bodies; the weight ratio of the biologically active material and grinding matrix mixture to the milling bodies; the duration of milling; the physical properties of both the biologically active material and the grinding matrix; the atmosphere present during activation; and others.

Advantageously, the media mill is capable of repeatedly or continuously applying mechanical compressive forces and shear stress to the biologically active material and the grinding matrix. Suitable media mills include but are not limited to the following: high-energy ball, sand, bead or pearl mills, basket mill, planetary mill, vibratory action ball mill, multi-axial shaker/mixer, stirred ball mill, horizontal small media mill, multi-ring pulverizing mill, and the like, including small milling media. The milling apparatus also can contain one or more rotating shafts.

In a preferred form of the invention, the dry milling is performed in a ball mill. Throughout the remainder of the specification reference will be made to dry milling being carried out by way of a ball mill. Examples of this type of mill are attritor mills, nutating mills, tower mills, planetary mills, vibratory mills and gravity-dependent-type ball mills. It will be appreciated that dry milling in accordance with the method of the invention may also be achieved by any suitable means other than ball milling. For example, dry milling may also be achieved using jet mills, rod mills, roller mills or crusher mills.

Biologically Active Material

The biologically active material includes active compounds, including compounds for veterinary and human use such as but not limited to, pharmaceutical actives and the like.

The biologically active material is ordinarily a material for which one of skill in the art desires improved dissolution properties. The biologically active material may be a conventional active agent or drug, although the process of the invention may be employed on formulations or agents that already have reduced particle size compared to their conventional form.

Biologically active materials suitable for use in the invention include diclofenac.

As discussed in the context of the background to the invention, biologically active materials that are poorly water soluble at gastrointestinal pH will particularly benefit from being prepared, and the method of the present invention is particularly advantageously applied to materials that are poorly water soluble at gastrointestinal pH.

Conveniently, the biologically active material is capable of withstanding temperatures that are typical in uncooled dry milling, which may exceed 80° C. Therefore, materials with a melting point about 80° C. or greater are highly suitable. For biologically active materials with lower melting points, the media mill may be cooled, thereby allowing materials with significantly lower melting temperatures to be processed according to the method of the invention. For instance, a simple water-cooled mill will keep temperatures below 50°

C., or chilled water could be used to further lower the milling temperature. Those skilled in the art will understand that a high energy ball mill could be designed to run at any temperature between say −30 to 200° C. For some biologically active materials it may be advantageous to control the milling temperature to temperatures significantly below the melting points of the biologically active materials.

The biologically active material is obtained in a conventional form commercially and/or prepared by techniques known in the art.

It is preferred, but not essential, that the particle size of the biologically active material be less than about 1000 μm, as determined by sieve analysis. If the coarse particle size of the biologically active material is greater than about 1000 μm, then it is preferred that the particles of the biologically active material substrate be reduced in size to less than 1000 μm using another standard milling method.

Processed Biologically Active Material

Preferably, the biologically active materials, which have been subject to the methods of the invention, comprises particles of biologically active material of an average particle size, determined on a particle number basis, is equal to or less than a size selected from the group 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm and 100 nm.

Preferably, the biologically active materials, which have been subject to the methods of the invention, comprises particles of biologically active material of a median particle size, determined on a particle volume basis, equal or less than a size selected from the group 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm and 100 nm.

Preferably, the biologically active materials, which have been subject to the methods of the invention, comprises particles of biologically active material and wherein the Dx of the particle size distribution, as measured on a particle volume basis, is selected from the group consisting of less than or equal to 10,000 nm, 5000 nm, 3000 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm, and 100 nm; wherein x is greater than or equal to 90, These sizes refer to particles either fully dispersed or partially agglomerated.

Agglomerates of Biologically Active Material after Processing

Agglomerates comprising particles of biologically active material, said particles having a particle size within the ranges specified above, should be understood to fall within the scope of the present invention, regardless of whether the agglomerates exceed the ranges specified above.

Agglomerates comprising particles of biologically active material, said agglomerates having a total agglomerate size within the ranges specified above, should be understood to fall within the scope of the present invention.

Agglomerates comprising particles of biologically active material should be understood to fall within the scope of the present invention if at the time of use, or further processing, the particle size of the agglomerate is within the ranges specified above.

Agglomerates comprising particles of biologically active material, said particles having a particle size within the ranges specified above, at the time of use, or further processing, should be understood to fall within the scope of the present invention, regardless of whether the agglomerates exceed the ranges specified above.

Processing Time

Preferably, the biologically active material and the grinding matrix are dry milled for the shortest time necessary to form the mixture of the biologically active material in the grinding matrix such that the active material has improved dissolution to minimise any possible contamination from the media mill and/or the plurality of milling bodies. This time varies greatly, depending on the biologically active material and the grinding matrix, and may range from as short as 1 minute to several hours. Dry milling times in excess of 2 hours may lead to degradation of the biologically active material and an increased level of undesirable contaminants.

Suitable rates of agitation and total milling times are adjusted for the type and size of milling apparatus as well as the milling media, the weight ratio of the biologically active material and grinding matrix mixture to the plurality of milling bodies, the chemical and physical properties of the biologically active material and grinding matrix, and other parameters that may be optimized empirically.

Inclusion of the Grinding Matrix with the Biologically Active Material and Separation of the Grinding Matrix from the Biologically Active Material In a preferred aspect, the grinding matrix is not separated from the biologically active material but is maintained with the biologically active material in the final product. Preferably the grinding matrix is considered to be Generally Regarded as Safe (GRAS) for pharmaceutical products.

In an alternative aspect, the grinding matrix is separated from the biologically active material. In one aspect, where the grinding matrix is not fully milled, the unmilled grinding matrix is separated from the biologically active material. In a further aspect, at least a portion of the milled grinding matrix is separated from the biologically active material.

Any portion of the grinding matrix may be removed, including but not limited to 10%, 25%, 50%, 75%, or substantially all of the grinding matrix.

In some embodiments of the invention, a significant portion of the milled grinding matrix may comprise particles of a size similar to and/or smaller than the particles comprising the biologically active material. Where the portion of the milled grinding matrix to be separated from the particles comprising the biologically active material comprises particles of a size similar to and/or smaller than the particles comprising the biologically active material, separation techniques based on size distribution are inapplicable.

In these circumstances, the method of the present invention may involve separation of at least a portion of the milled grinding matrix from the biologically active material by techniques including but not limited to electrostatic separation, magnetic separation, centrifugation (density separation), hydrodynamic separation, froth flotation.

Advantageously, the step of removing at least a portion of the milled grinding matrix from the biologically active material may be performed through means such as selective dissolution, washing, or sublimation.

An advantageous aspect of the invention would be the use of grinding matrix that has two or more components where at least one component is water soluble and at least one component has low solubility in water. In this case washing can be used to remove the matrix component soluble in water leaving the biologically active material encapsulated in the remaining matrix components. In a highly advantageous aspect of the invention the matrix with low solubility is a functional excipient.

A highly advantageous aspect of the present invention is that certain grinding matrixes appropriate for use in the method of the invention (in that they physically degrade to the desired extent under dry milling conditions) are also pharmaceutically acceptable and thus appropriate for use in a medicament. Where the method of the present invention does not involve complete separation of the grinding matrix from the biologically active material, the present invention encompasses methods for the production of a medicament incorporating both the biologically active material and at least a portion of the milled grinding matrix, medicaments so produced and methods of treatment of an animal, including man, using a therapeutically effective amount of said biologically active materials by way of said medicaments.

The medicament may include only the biologically active material and the grinding matrix or, more preferably, the biologically active materials and grinding matrix may be combined with one or more pharmaceutically acceptable carriers, as well as any desired excipients or other like agents commonly used in the preparation of medicaments.

Analogously, a highly advantageous aspect of the present invention is that certain grinding matrixes appropriate for use in the method of the invention (in that they physically degrade to a desirable extent under dry milling conditions) are also appropriate for use in an agricultural chemical composition. Where the method of the present invention does not involve complete separation of the grinding matrix from the biologically active material, the present invention encompasses methods for the production of a agricultural chemical composition incorporating both the biologically active material and at least a portion of the milled grinding matrix, agricultural chemical composition so produced and methods of use of such compositions.

The agricultural chemical composition may include only the biologically active material and the grinding matrix or, more preferably, the biologically active materials and grinding matrix may be combined with one or more acceptable carriers, as well as any desired excipients or other like agents commonly used in the preparation of agricultural chemical compositions.

In one particular form of the invention, the grinding matrix is both appropriate for use in a medicament and readily separable from the biologically active material by methods not dependent on particle size. Such grinding matrixes are described in the following detailed description of the invention. Such grinding matrixes are highly advantageous in that they afford significant flexibility in the extent to which the grinding matrix may be incorporated with the biologically active material into a medicament.

The mixture of biologically active material and grinding matrix may then be separated from the milling bodies and removed from the mill.

In one embodiment, the grinding matrix is separated from the mixture of biologically active material and grinding matrix. Where the grinding matrix is not fully milled, the unmilled grinding matrix is separated from the biologically active material. In a further aspect, at least a portion of the milled grinding matrix is separated from the biologically active material.

The milling bodies are essentially resistant to fracture and erosion in the dry milling process.

The quantity of the grinding matrix relative to the quantity of biologically active material, and the extent of milling of the grinding matrix, is sufficient to provide reduced particle size of the biologically active material.

The grinding matrix is neither chemically nor mechanically reactive with the pharmaceutical material under the dry milling conditions of the method of the invention except, for example, where the matrix is deliberately chosen to undergo a mechanico-chemical reaction. Such a reaction might be the conversion of a free base or acid to a salt or vice versa.

Preferably, the medicament is a solid dosage form, however, other dosage forms may be prepared by those of ordinary skill in the art.

In one form, after the step of separating said mixture of biologically active material and grinding matrix from the plurality of milling bodies, and before the step of using said mixture of biologically active material and grinding matrix in the manufacture of a medicament, the method may comprise the step of:

removing a portion of the grinding matrix from said mixture of biologically active material and grinding matrix to provide a mixture enriched in the biologically active material;

and the step of using said mixture of biologically active material and grinding matrix in the manufacture of a medicament, more particularly comprises the step of using the mixture of biologically active material and grinding matrix enriched in the biologically active material form in the manufacture of a medicament.

The present invention includes medicaments manufactured by said methods, and methods for the treatment of an animal, including man, by the administration of a therapeutically effective amount of the biologically active materials by way of said medicaments.

In another embodiment of the invention, a facilitating agent or a combination of facilitating agents is also comprised in the mixture to be milled. Such facilitating agents appropriate for use in the invention include diluents, surfactants, polymers, binding agents, filling agents, lubricating agents, sweeteners, flavouring agents, preservatives, buffers, wetting agents, disintegrants, effervescent agents and agents that may form part of a medicament, including a solid dosage form, or other excipients required for other specific drug delivery, such as the agents and media listed below under the heading Medicinal and Pharmaceutical Compositions, or any combination thereof.

Biologically Active Materials and Compositions

The present invention encompasses pharmaceutically acceptable materials produced according to the methods of the present invention, compositions including such materials, including compositions comprising such materials together with the grinding matrix with or without milling aids, facilitating agents, with at least a portion of the grinding matrix or separated from the grinding matrix.

The pharmaceutically acceptable materials within the compositions of the invention are present at a concentration of between about 0.1% and about 99.0% by weight. Preferably, the concentration of pharmaceutically acceptable materials within the compositions will be about 5% to about 80% by weight, while concentrations of 10% to about 50% by weight are highly preferred. Desirably, the concentration will be in the range of about 10 to 15% by weight, 15 to 20% by weight, 20 to 25% by weight, 25 to 30% by weight, 30 to 35% by weight, 35 to 40% by weight, 40 to 45% by weight, 45 to 50% by weight, 50 to 55% by weight, 55 to 60% by weight, 60 to 65% by weight, 65 to 70% by weight, 70 to 75% by weight or 75 to 80% by weight for the composition prior to any later removal (if desired) of any portion of the grinding matrix. Where part or all of the grinding matrix has been removed, the relative concentration of pharmaceutically acceptable materials in the composition may be considerably higher depending on the amount of the grinding matrix that is removed. For example, if all of the grinding matrix is removed the concentration of particles in the preparation may approach 100% by weight (subject to the presence of facilitating agents).

Compositions produced according to the present invention are not limited to the inclusion of a single species of pharmaceutically acceptable materials. More than one species of pharmaceutically acceptable materials may therefore be present in the composition. Where more than one species of pharmaceutically acceptable materials is present, the composition so formed may either be prepared in a dry milling step, or the pharmaceutically acceptable materials may be prepared separately and then combined to form a single composition.

Medicaments

The medicaments of the present invention may include the pharmaceutically acceptable material, optionally together with the grinding matrix or at least a portion of the grinding matrix, with or without milling aids, facilitating agents, combined with one or more pharmaceutically acceptable carriers, as well as other agents commonly used in the preparation of pharmaceutically acceptable compositions.

As used herein "pharmaceutically acceptable carrier" includes any and all solvents, dispersion media, coatings, antibacterial and antifungal agents, isotonic and absorption delaying agents, and the like that are physiologically compatible. Preferably, the carrier is suitable for parenteral administration, intravenous, intraperitoneal, intramuscular, sublingual, pulmonary, transdermal or oral administration. Pharmaceutically acceptable carriers include sterile aqueous solutions or dispersions and sterile powders for the extemporaneous preparation of sterile injectable solutions or dispersion. The use of such media and agents for the manufacture of medicaments is well known in the art. Except insofar as any conventional media or agent is incompatible with the pharmaceutically acceptable material, use thereof in the manufacture of a pharmaceutical composition according to the invention is contemplated.

Pharmaceutical acceptable carriers according to the invention may include one or more of the following examples:

(1) surfactants and polymers including, but not limited to polyethylene glycol (PEG), polyvinylpyrrolidone (PVP), polyvinylalcohol, crospovidone, polyvinylpyrrolidone-polyvinylacrylate copolymer, cellulose derivatives, hydroxypropylmethyl cellulose, hydroxypropyl cellulose, carboxymethylethyl cellulose, hydroxypropylmethyl cellulose phthalate, polyacrylates and polymethacrylates, urea, sugars, polyols, and their polymers, emulsifiers, sugar gum, starch, organic acids and their salts, vinyl pyrrolidone and vinyl acetate (2) binding agents such as various celluloses and cross-linked polyvinylpyrrolidone, microcrystalline cellulose; and or (3) filling agents such as lactose monohydrate, lactose anhydrous, microcrystalline cellulose and various starches; and or (4) lubricating agents such as agents that act on the flowability of the powder to be compressed, including colloidal silicon dioxide, talc, stearic acid, magnesium stearate, calcium stearate, silica gel; and or (5) sweeteners such as any natural or artificial sweetener including sucrose, xylitol, sodium saccharin, cyclamate, aspartame, and acesulfame K; and or (6) flavouring agents; and or (7) preservatives such as potassium sorbate, methylparaben, propylparaben, benzoic acid and its salts, other esters of parahydroxybenzoic acid such as butylparaben, alcohols such as ethyl or benzyl alcohol, phenolic chemicals such as phenol, or quarternary compounds such as benzalkonium chloride; and or (8) buffers; and or (9) Diluents such as pharmaceutically acceptable inert fillers, such as microcrystalline cellulose, lactose, dibasic calcium phosphate, saccharides, and/or mixtures of any of the foregoing; and or

(10) wetting agents such as corn starch, potato starch, maize starch, and modified starches, croscarmellose sodium, crosspovidone, sodium starch glycolate, and mixtures thereof; and or

(11) disintegrants; and or

(12) effervescent agents such as effervescent couples such as an organic acid (e.g., citric, tartaric, malic, fumaric, adipic, succinic, and alginic acids and anhydrides and acid salts), or a carbonate (e.g. sodium carbonate, potassium carbonate, magnesium carbonate, sodium glycine carbonate, L-lysine carbonate, and arginine carbonate) or bicarbonate (e.g. sodium bicarbonate or potassium bicarbonate); and or

(13) other pharmaceutically acceptable excipients.

Medicaments of the invention suitable for use in animals and in particular in man typically must be stable under the conditions of manufacture and storage. The medicaments of the invention comprising the biologically active material can be formulated as a solid, a solution, a microemulsion, a liposome, or other ordered structures suitable to high drug concentration. Actual dosage levels of the biologically active material in the medicament of the invention may be varied in accordance with the nature of the biologically active material, as well as the potential increased efficacy due to the advantages of providing and administering the biologically active material (e.g., increased solubility, more rapid dissolution, increased surface area of the biologically active material, etc.). Thus as used herein "therapeutically effective amount" will refer to an amount of biologically active material required to effect a therapeutic response in an animal. Amounts effective for such a use will depend on: the desired therapeutic effect; the route of administration; the potency of the biologically active material; the desired duration of treatment; the stage and severity of the disease being treated; the weight and general state of health of the patient; and the judgment of the prescribing physician. In another embodiment, the biologically active material, optionally together with the grinding matrix or at least a portion of the grinding matrix, of the invention may be combined into a medicament with another biologically active material, or even the same biologically active material. In the latter embodiment, a medicament may be achieved which provides for different release characteristics—early release from the biologically active material, and later release from a larger average size biologically active material.

Pharmacokinetic Properties of Diclofenac Compositions

Suitable animal models to determine pharmacokinetic parameters are described in the prior art, such as the beagle dog model described in U.S. Pat. No. 7,101,576.

Fast Onset of Activity

The diclofenac compositions of the invention exhibit faster therapeutic effects.

In one example, following administration the diclofenac compositions of the invention comprising diclofenac have a $T_{max}$ of less than about 5 hours, less than about 4.5 hours, less than about 4 hours, less than about 3.5 hours, less than about 3 hours, less than about 2.75 hours, less than about 2.5 hours, less than about 2.25 hours, less than about 2 hours, less than about 1.75 hours, less than about 1.5 hours, less than about 1.25 hours, less than about 1.0 hours, less than about 50 minutes, less than about 40 minutes, less than about 30 minutes, less than about 25 minutes, less than about 20 minutes, less than about 15 minutes, less than about 10 minutes, less than about 5 minutes, or less than about 1 minute.

Increased Bioavailability

The diclofenac compositions of the invention preferably exhibit increased bioavailability (AUC) and require smaller doses as compared to prior conventional compositions administered at the same dose. Any drug composition can have adverse side effects. Thus, lower doses of drugs which can achieve the same or better therapeutic effects as those observed with larger doses of conventional compositions are desired. Such lower doses can be realized with the compositions of the invention because the greater bioavailability observed with the compositions as compared to conventional drug formulations means that smaller doses of drug are required to obtain the desired therapeutic effect.

The Pharmacokinetic Profiles of the Compositions of the Invention are not Substantially Affected by the Fed or Fasted State of the Subject Ingesting the Compositions The invention encompasses diclofenac compositions wherein the pharmacokinetic profile of the composition is not substantially affected by the fed or fasted state of a subject ingesting the composition. This means that there is no substantial difference in the quantity of composition or the rate of composition absorption when the compositions are administered in the fed versus the fasted state. Thus, the compositions of the invention substantially eliminate the effect of food on the pharmacokinetics of the composition.

The difference in absorption of the diclofenac composition of the invention, when administered in the fed versus the fasted state, is less than about 35%, less than about 30%, less than about 25%, less than about 20%, less than about 15%, less than about 10%, less than about 5%, or less than about 3%. This is an especially important feature in treating patients with difficulty in maintaining a fed state.

In addition, preferably the difference in the rate of absorption (i.e., $T_{max}$) of the diclofenac compositions of the invention, when administered in the fed versus the fasted state, is less than about 100%, less than about 90%, less than about 80%, less than about 70%, less than about 60%, less than about 50%, less than about 40%, less than about 30%, less than about 20%, less than about 15%, less than about 10%, less than about 5%, less than about 3%, or essentially no difference. Benefits of a dosage form which substantially eliminates the effect of food include an increase in subject convenience, thereby increasing subject compliance, as the subject does not need to ensure that they are taking a dose either with or without food.

Preferably, the $T_{max}$ of an administered dose of a diclofenac composition of the invention is less than that of a conventional drug active composition, administered at the same dosage. A preferred diclofenac composition of the invention exhibits in comparative pharmacokinetic testing with a standard conventional drug active composition, in oral suspension, capsule or tablet form, a $T_{max}$ which is less than about 100%, less than about 90%, less than about 80%, less than about 70%, less than about 60%, less than about 50%, less than about 40%, less than about 30%, less than about 25%, less than about 20%, less than about 15%, or less than about 10% of the $T_{max}$ exhibited by the standard conventional drug active composition.

In addition, preferably the $C_{max}$ of a diclofenac composition of the invention is greater than the $C_{max}$ of a conventional drug active composition, administered at the same dosage. A preferred diclofenac composition of the invention exhibits in comparative pharmacokinetic testing with a standard conventional drug active composition, in oral suspension, capsule or tablet form, a $C_{max}$ which is greater than about 5%, greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, or greater than about 150% than the $C_{max}$ exhibited by the standard conventional drug active composition.

In addition, preferably the diclofenac composition has an AUC greater than that of the equivalent conventional composition administered at the same dosage. A preferred diclofenac composition of the invention exhibits in comparative pharmacokinetic testing with a standard conventional drug active composition, in oral suspension, capsule or tablet form, a AUC which is greater than about 5%, greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, or greater than about 150% than the AUC exhibited by the standard conventional drug active composition.

Any standard pharmacokinetic protocol can be used to determine blood plasma concentration profile in humans following administration of a composition, and thereby establish whether that composition meets the pharmacokinetic criteria set out herein. For example, a randomized single-dose crossover study can be performed using a group of healthy adult human subjects. The number of subjects should be sufficient to provide adequate control of variation in a statistical analysis, and is typically about 10 or greater, although for certain purposes a smaller group can suffice. Each subject receives by oral administration at time zero a single dose (e.g., 300 mg) of a test formulation of composition, normally at around 8 am following an overnight fast. The subjects continue to fast and remain in an upright position for about 4 hours after administration of the composition. Blood samples are collected from each subject prior to administration (e.g., 15 minutes) and at several intervals after administration. For the present purpose it is preferred to take several samples within the first hour, and to sample less frequently thereafter. Illustratively, blood samples could be collected at 15, 30, 45, 60, and 90 minutes after administration, then every hour from 2 to 10 hours after administration. Additional blood samples may also be taken later, for example at 12 and 24 hours after administration. If the same subjects are to be used for study of a second test formulation, a period of at least 7 days should elapse before administration of the second formulation. Plasma is separated from the blood samples by centrifugation and the separated plasma is analyzed for composition by a validated high performance liquid chromatography (HPLC) or liquid chromatography mass spectrometry (LCMS) procedure. Plasma concentrations of composition referenced herein are intended to mean total concentrations including both free and bound composition.

Any formulation giving the desired pharmacokinetic profile is suitable for administration according to the present methods. Exemplary types of formulations giving such profiles are liquid dispersions and solid dose forms of composition. If the liquid dispersion medium is one in which the composition has very low solubility, the particles are present as suspended particles. The smaller the particles the higher the probability that the formulation will exhibit the desired pharmacokinetic profile.

Thus, an diclofenac composition of the invention, upon administration to a subject, provides improved pharmacokinetic and/or pharmacodynamic properties compared with a standard reference diclofenac composition as measured by at least one of speed of absorption, dosage potency, efficacy, and safety.

Modes of Administration of Medicaments Comprising Biologically Active Materials

Medicaments of the invention can be administered to animals, including man, in any pharmaceutically acceptable manner, such as orally, rectally, pulmonary, intravaginally, locally (powders, ointments or drops), transdermal, parenteral administration, intravenous, intraperitoneal, intramuscular, sublingual or as a buccal or nasal spray Solid dosage forms for oral administration include capsules, tablets, pills, powders, pellets, and granules. Further, incorporating any of the normally employed excipients, such as those previously listed, and generally 5-95% of the biologically active agent, and more preferably at a concentration of 10%-75% will form a pharmaceutically acceptable non-toxic oral composition.

Medicaments of the invention may be parenterally administered as a solution of the biologically active agent suspended in an acceptable carrier, preferably an aqueous carrier. A variety of aqueous carriers may be used, e.g. water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration.

For aerosol administration, medicaments of the invention are preferably supplied along with a surfactant or polymer and propellant. The surfactant or polymer must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed.

The surfactant or polymer may constitute 0.1%-20% by weight of the composition, preferably 0.25-5%. The balance of the composition is ordinarily propellant. A carrier can also be included, as desired, as with, e.g., lecithin for intranasal delivery.

Medicaments of the invention may also be administered via liposomes, which serve to target the active agent to a particular tissue, such as lymphoid tissue, or targeted selectively to cells. Liposomes include emulsions, foams, micelles, insoluble monolayers, liquid crystals, phospholipid dispersions, lamellar layers and the like. In these preparations the composite microstructure composition is incorporated as part of a liposome, alone or in conjunction with a molecule that binds to or with other therapeutic or immunogenic compositions.

As described above, the biologically active material can be formulated into a solid dosage form (e.g., for oral or suppository administration), together with the grinding matrix or at least a portion of it. In this case there may be little or no need to add stabilizing agents since the grinding matrix may effectively act as a solid-state stabilizer.

However, if the biologically active material is to be utilized in a liquid suspension, the particles comprising the biologically active material may require further stabilization once the solid carrier has been substantially removed to ensure the elimination, or at least minimisation of particle agglomeration.

Therapeutic Uses

Therapeutic uses of the medicaments of the invention include pain relief, anti-inflammatory, migraine, asthma, and other disorders that require the active agent to be administered with a high bioavailability.

One of the main areas when rapid bioavailability of a biologically active material is required is in the relief of pain. The minor analgesics, such as cyclooxgenase inhibitors (aspirin related drugs) may be prepared as medicaments according to the present invention.

Medicaments of the invention may also be used for treatment of eye disorders. That is, the biologically active material may be formulated for administration on the eye as an aqueous suspension in physiological saline, or a gel. In addition, the biologically active material may be prepared in a powder form for administration via the nose for rapid central nervous system penetration.

Treatment of cardiovascular disease may also benefit from biologically active materials according to the invention, such as treatment of angina pectoris and, in particular, molsidomine may benefit from better bioavailability.

Other therapeutic uses of the medicaments of the present invention include treatment of hair loss, sexual dysfunction, or dermal treatment of psoriasis.

The present invention will now be described with reference to the following non-limiting Examples. The description of the Examples is in no way limiting on the preceding paragraphs of this specification, but is provided for exemplification of the methods and compositions of the invention.

EXAMPLES

It will be apparent to persons skilled in the milling and pharmaceutical arts that numerous enhancements and modifications can be made to the above described processes without departing from the basic inventive concepts. For example, in some applications the biologically active material may be pretreated and supplied to the process in the pretreated form. All such modifications and enhancements are considered to be within the scope of the present invention, the nature of which is to be determined from the foregoing description and the appended claims. Furthermore, the following Examples are provided for illustrative purposes only, and are not intended to limit the scope of the processes or compositions of the invention.

The Following Materials were Used in the Examples

Active pharmaceutical ingredients were sourced from commercial suppliers, excipients from either commercial suppliers such as Sigma-Aldrich or retailers, while food ingredients were sourced from retailers.

The Following Mills were Used for the Grinding Experiments

Spex-Type Mill:

Small scale milling experiments were conducted using a vibratory Spex 8000D mixer/mill. Twelve ⅜" stainless steel balls were used as the grinding media. The powder charge and grinding media were loaded into a hardened steel vial with an internal volume of approximately 75 mL. Following milling, the milled material was discharged from the vial and sieved to remove grinding media.

Attritor-Type Mill:

Small scale attritor milling experiments were performed using a 1 HD Union Process attritor mill with a 110 mL grinding chamber. The grinding media consisted of 330 g 5/16" stainless steel balls. The mill was loaded through the loading port, with dry materials added initially, followed by the grinding media. The milling process was conducted with the jacket cooled at 10-20° C. and the shaft rotating at 500 rpm. Upon completion of milling, the milled material was discharged from the mill and sieved to remove the grinding media.

Medium scale attritor milling experiments were performed using a 1HD Union Process attritor mill with a 1 L grinding chamber or a 1S Union Process attritor mill with a 750 mL grinding chamber. The grinding media consisted of 3 kg of 5/16" stainless steel balls or 1.5 kg of 3/8" stainless steel balls for the 1S attritor. The 1HD mill was loaded through the loading port, with dry materials added initially, followed by the grinding media, while the grinding media was added initially, followed by the dry materials in the 1S attritor mill. The milling process was conducted with the jacket cooled at 10-20° C. with the shaft rotating at 350 rpm in the 1HD attritor or 550 rpm in the 1S attritor. Upon completion of milling, the milled material was discharged from the mill and sieved to remove the grinding media.

Medium to large scale attritor milling experiments were performed using a 1S Union Process attritor mill with a ½ gallon grinding chamber. The grinding media consisted of 7 kg of 3/8" stainless steel balls. The mill was loaded through the loading port, with the grinding media added initially, followed by the dry powders. The milling process was conducted with the jacket cooled at 18° C. and the shaft rotating at 550-555 rpm. Upon completion of milling, the milled powder was discharged from the mill through the bottom discharge port at 77 rpm for 5 min.

Large scale attritor milling experiments were performed using a 1S Union Process attritor mill with a 1½ gallon grinding chamber. The grinding media consisted of 20 kg of 3/8" stainless steel balls. The mill was loaded through the loading port, with the grinding media added initially, then followed by the dry powders. The milling process was conducted with the jacket cooled to ambient temperature and the shaft rotating at 300 rpm. Upon completion of milling, the milled powder was discharged from the mill through the bottom discharge port at 77 rpm for 5 min.

The largest scale attritor millings were done in a 30S Union Process mill with a 25 gallon grinding chamber (Union Process, Akron Ohio, USA). The grinding media consisted of 454 kg of 3/8" stainless steel balls. The mill was loaded through its split top lid, with the grinding media added initially, then followed by the dry powders (25 kg). The milling process was conducted with the jacket cooled to 10° C. and the shaft rotating at 130 rpm. Upon completion of milling, the milled powder was discharged from the mill through the bottom discharge port at 77 rpm for 5 min.

Siebtechnik Mill

Medium scale milling experiments were also performed in a Siebtechnik GSM06 (Siebtechnik, GmbH, Germany) with two 1 L milling chambers. Each chamber was filled with 2.7 kg stainless steel media with a diameter of 3/8". The media and powder were loaded with the lid off. The mill was operated at ambient temperature. The vibration speed was the standard mill settings. Upon completion of the milling the media was separated from the powder by sieving.

Simoloyer Mill

Medium scale milling experiments were performed in a Simoloyer CM01 (ZOZ GmbH, Germany) with a 2 L milling chamber. The grinding media consisted of 2.5 kg stainless steel media with a diameter of 5 mm. the media was loaded though the loading port followed by the dry materials. The milling vessel was cooled using water at a temperature of about 18° C. The mill speed was operated in cycle mode: at 1300 rpm for two minutes and at 500 rpm for 0.5 min and so forth. Upon completion of the milling the media was discharged from the mill using a grated valve to retain the grinding media.

Large scale milling experiments were performed in a Simoloyer CM100 (ZOZ GmbH, Germany) with a 100 L milling chamber. The grinding media consisted of 100 kg stainless steel media with a diameter of 3/16". The powder charge (11 kg) was added to the milling chamber, which already contained the grinding media, through a loading port. The milling chamber was cooled to 18° C. and the powder was milled for a total of 20 minutes using a cycling mode equivalent to a tip speed at 1300/500 rpm for 2/0.5 min in the CM-01 type mill. Upon completion of the milling the mill was discharged by sucking the powder into a cyclone.

Hicom Mill

Millings performed in a nutating Hicom mill utilized 14 kg of stainless steel 0.25" grinding media together with a powder charge of 480 g. The mill was loaded by pre-mixing media and powder, then adding the mixture to the grinding chamber through the loading port at the top of the mill. The milling was done at 1000 rpm and the mill discharged by inverting the mill and emptying through the loading port. The recovered material was sieved to separate the grinding media from the powder.

Variations to the milling conditions set out above are indicated in the variations column in the data tables. The key to these variations is shown in Table A.

Particle Size Measurement:

The particle size distribution (PSD) was determined using a Malvern Mastersizer 2000 fitted with a Malvern Hydro 2000S pump unit. Measurement settings used: Measurement Time: 12 seconds, Measurement cycles: 3. Final result generated by averaging the 3 measurements. Samples were prepared by adding 200 mg of milled material to 5.0 mL of 1% PVP in 10 mM hydrochloric acid (HCl), vortexing for 1 min and then sonicating. From this suspension enough was added into the dispersant (10 mM HCl) to attain a desired obscuration level. If necessary an extra 1-2 minutes of sonication was applied using the internal sonication probe in the measurement cell. The refractive index of the active ingredient to be measured was in the range of 1.49-1.73. Any variations to this general method are summarized in Table B.

XRD Analysis:

Powder X-Ray diffraction (XRD) patterns were measured with a Diffractometer D 5000, Kristalloflex (Siemens). The measurement range was from 5-18 degrees 2-Theta. The slit width was set to 2 mm and the cathode ray tube was operated at 40 kV and 35 mA. Measurements were recorded at room temperature. The recorded traces were subsequently processed using Bruker EVA software to obtain the diffraction pattern.

TABLE A

Variations to milling conditions. Only conditions reported in the table have changed as compared to conditions reported above.

| Variation # | Mill type | Milling Speed (rpm) | Media size (inch) | Media Mass (kg) | Offload spped (rpm) |
|---|---|---|---|---|---|
| A | 1HD 1 L | | 0.25 | | |
| B | 1S 0.5 gal | | | 5 | |
| C | 1S 0.5 gal | | | 4 | |
| D | 1S 0.5 gal | 500 | | | |
| E | 1S 0.5 gal | 550-555 | | | |
| F | 1S 1.5 gal | 316-318 | | 21 | |
| G | 1S 1.5 gal | 500 | | 21 | |
| H | 1S 1.5 gal | 355 | | 21 | |
| I | 1S 1.5 gal | 355 | | 18 | |
| J | 1S 1.5 gal | | | 21 | |
| K | 1S 1.5 gal | | | 18.4 | |
| L | 1S 1.5 gal | 400 | | | |

TABLE A-continued

Variations to milling conditions. Only conditions reported in the table have changed as compared to conditions reported above.

| Variation # | Mill type | Milling Speed (rpm) | Media size (inch) | Media Mass (kg) | Offload spped (rpm) |
|---|---|---|---|---|---|
| M | 1S 1.5 gal | | | 21 | 57 |
| N | 1S 1.5 gal | | | | 57 |
| O | 1S 0.5 gal | 400 | | | 400 |
| P | 1S 0.5 gal | 500 | | | 350 |
| Q | HICOM | | ⅛ | | |
| R | HICOM | | | 11.7 | |

TABLE B

Variations to particle size measurement conditions.

| Variation # | Sample Dispersant | Measurement Dispersant | Addition Method |
|---|---|---|---|
| 1 | | 0.1% PVP in DI water | Powder addition |
| 2 | 0.2% Pluronic L81 in DI water | DI water | |
| 3 | | Saturated glyphosate in DI water | Powder addition |
| 4 | | Saturated glyphosate in DI water | Powder addition |
| 5 | 1% PVP in DI water | DI water | |
| 6 | | DI water | Powder addition |
| 7 | 1% PVP in DI water | Saturated creatine in DI water | |
| 8 | 1% PVP in DI water | 10 mM HCl | |
| 9 | 0.2% Pluronic L81 in DI water | Acidified with 1M HCl | |
| 10 | 1% PVP in DI water | 0.1% PVP in DI water | |
| 11 | 1% PVP in DI water | 1% PVP in DI water | |
| 12 | | | Filtered before PSD measurement |

Abbreviations:
HCl: Hydrochloric acid
Nap: Naproxen acid
PSD: Particles size distribution
PVP: Polyvinyl pyrrolidone
RI: Refractive index
Rpm: Revolutions per minute
SLS: Sodium lauryl sulphate
SSB: Stainless Steel Balls
XRD: X-Ray Diffraction Other abbreviations used in the data tables are listed below in Table C (for actives), Table D (for matrices) and Table E (for surfactants). In the data tables single letter with example number abbreviations have been used to identify specific sample numbers within the table. The data tables shown in the figures the use of surfactant, matrix are interchangeable and do not necessarily define the nature of that material.

TABLE C

Abbreviations used for active pharmaceutical ingredients.

| API Name | Abbreviation |
|---|---|
| 2,4-Dichlorophenoxyacetic acid | 2,4D |
| Anthraquinone | ANT |
| Celecoxib | CEL |
| Cilostazol | CIL |
| Ciprofloxacin | CIP |
| Creatine Monohydrate | CRM |
| Cyclosporin A | CYA |
| Diclofenac Acid | DIC |
| Glyphosate | GLY |
| Halusulfuron | HAL |
| Diclofenac | IND |
| Mancozeb | MAN |
| Meloxicam | MEL |
| Metaxalone | MTX |
| Metsulfuron | MET |
| Naproxen Acid | NAA |
| Naproxen Sodium | NAS |
| Progesterone | PRO |
| Salbutamol | SAL |
| Sulfur | SUL |
| Tribenuran | TRI |

TABLE D

Abbreviations used for excipients.

| Matrix Name | Abbreviation |
|---|---|
| Calcium Carbonate | CAC |
| Glucose | GLU |
| Lactose Anhydrous | LAA |
| Lactose Monohydrate | LAC |
| Lactose Monohydrate Food Grade | LFG |
| Malic Acid | MAA |
| Maltitol | MAL |
| Mannitol | MAN |
| Sodium Bicarbonate | SB |
| Sodium Chloride | SC |
| Sorbitol | SOR |
| Sucrose | SUC |
| Tartaric Acid | TA |
| TriSodium Citrate Dihydrate | TCD |
| Whey Powder | WP |
| Xylitol | XYL |

TABLE E

Abbreviations used for surfactants

| Surfactant Name | Abbreviation |
|---|---|
| Aerosil R972 Silica | AS |
| Benzalkonium Chloride | BC |
| Brij700 | B700 |
| Brij76 | B76 |
| Cremophor EL | CEL |
| Cremophor RH-40 | C40 |
| Dehscofix 920 | D920 |
| Docusate Sodium | DS |
| Kollidon 25 | K25 |
| Kraftsperse 1251 | K1251 |
| Lecithin | LEC |
| Poloxamer 188 | P188 |
| Microcrystalline Cellulose | MCC |
| Poloxamer 407 | P407 |
| Polyethylene Glycol 3000 | P3000 |
| Polyethylene Glycol 8000 | P8000 |
| Polyoxyethylene 40 Stearate | P40S |
| Polyvinyl Pyrrolidone (Kollidon 30) | PVP |
| Primellose | PML |
| Primojel | PRI |
| Sodium Deoxycholate | SDC |
| Sodium Dodecyl Sulphate | SDS |
| Sodium Dodecylbenzenesulphonic | SDA |

TABLE E-continued

Abbreviations used for surfactants

| Surfactant Name | Abbreviation |
|---|---|
| Acid | |
| Sodium N-Lauroyl Sarcosine | SNS |
| Sodium Octadecyl Sulphate | SOS |
| Sodium Pentane Sulphonate | SPS |
| Soluplus HS15 | SOL |
| Teric 305 | T305 |
| Tersperse 2700 | T2700 |
| Terwet 1221 | T1221 |
| Terwet 3785 | T3785 |
| Tween 80 | T80 |

Example 1

Spex Milling

A range of actives, matrices and surfactants in a variety of combinations were milled using the Spex mill. The details of these millings are shown in FIGS. 1A-1G together with the particle size distributions of actives that were milled.

These millings demonstrate that the addition of a small amount of surfactant to the milling matrix delivers a smaller particle size compared to millings of just an active and a single matrix. Some examples of this are samples Z and AA compared to sample Y; Sample AB compared to sample AC; sample AE compared to sample AD; sample AG compared to sample AF; sample AP compared to sample AO; sample AR compared to sample AQ, sample AT compared to sample AS; Samples AX, AY and AZ compared to sample AW; sample BC compared to sample BD; sample BI compared to BH; samples BL-BR compared to sample BK; samples CS-DB compared to sample DC. This last example is particularly noteworthy as these millings were undertaken at 45% v/v. This demonstrates the broad applicability of this invention. Some other examples of surfactant addition being beneficial for size reduction are samples DD-DG and DI-DK compared to sample DH; sample DM compared to sample DL. Other samples such as samples DY-EC compared to sample DX; sample AV compared to sample AU; samples B-H compared to sample A and samples K-M compared to sample J show this ti be also true when particle size statistics such the %<1 micron as used.

Note that this applies to mechanochemical matrix milling as well. This is demonstrated by sample BI where naproxen sodium is milled with tartaric acid and converted to naproxen acid. FIG. 1H shows XRD data that demonstrates the transformation.

Other samples such as CB-CR show examples were surfactants suitable for use with IV formulations can be used to manufacture very small particles.

It is also noteworthy that samples DS and DT could be sized using a saturated solution of the active (salbutamol) demonstrating that actives with high water solubility can be measured as long as care is taken when measuring the size.

Two sets of data, samples N-Q and samples R-U, also demonstrate that the invention described herein is unique. In these samples the active milled with a matrix and surfactant produces small particles. When milled with matrix alone the particles sizes are larger, in the case of sample Q they are not even nanoparticles. When the active is milled with just 1% surfactant the resultant particle size is very large. Even when 80% surfactant is used the size is large.

Example 2

110 mL Attritor

A range of actives, matrices and surfactants in a variety of combinations were milled using the 110 ml stirred attritor mill. The details of these millings are shown in FIG. 2A together with the particle size distributions of actives that were milled.

These millings also demonstrate that the addition of a small amount of surfactant to the milling matrix delivers a smaller particle size compared to millings of just an active and a single matrix in a small scale stirred mill as well as the vibratory Spex mill. Sample F also demonstrates that small particles can be achieved at high % actives when a surfactant is present. Sample D and E also show that the addition of the surfactant also increased the yield of powder from the mill.

Example 3

Second Matrix

In this example naproxen was milled with a mixture of two matrices using the Spex mill. The details of these millings are shown in FIG. 3A together with the particle size distributions of actives that were milled. Samples A and B were milled in a primary matrix of lactose monohydrate and 20% of second matrix. The particle size of these millings is smaller than the same milling with just lactose monohydrate (See example 1 sample No AH, FIG. 1B). The particle size is also smaller than naproxen milled in the secondary matrices (See example 1 sample No AI and AJ, FIG. 1B). This shows the mixed matrices have synergy together.

Samples C-E were milled in anhydrous lactose with 20% of a second matrix. All these samples had a particle size much smaller than naproxen milled in anhydrous lactose alone (See example 1 sample No AK, FIG. 1B).

These millings demonstrate that the addition of a second matrix to the primary milling matrix delivers a smaller particle size compared to millings with just a single matrix.

Example 4

1 L Attritor

Two actives with various combinations of lactose monohydrate and SDS were milled using the 1 L stirred attritor mill. The details of these millings are shown in FIG. 4A together with the particle size distributions of actives that were milled.

Sample A and B are millings of meloxicam at 20%. While sample B has a slightly smaller particle size than sample A there is a dramatic difference in the amount of material recovered from the milling. Sample A, milled with 3% SDS has a high yield of 90% whereas sample B with no surfactant has practically no yield with all the powder caked in the mill.

In samples C-F the milling of 13% diclofenac shows that the use of a second matrix (tartaric acid) in combination with 1% SDS delivers the best outcome of a good particle size and high yield. Sample D which has just the mixed matrix has very good particle size but poor yield.

These results show that the addition of a small amount of surfactant improves milling performance.

Example 5

750 mL Attritor

Two actives with various combinations surfactants were milled using the 750 ml stirred attritor mill. The details of these millings are shown in FIG. 5A together with the particle size distributions of actives that were milled.

In samples A-C three millings of naproxen are shown. Sample A has just 1% SDS as a surfactant. Samples B and C have a second surfactant present and these samples have a smaller particle size as measured by the %<500 nm, %<1000 nm and %<2000 nm.

In samples D-F three millings of diclofenac are shown. Sample D has just 1% SDS as a surfactant. Samples E and F have a second surfactant present and these samples have a smaller particle size compared to sample D.

These examples demonstrate that the use of combination of surfactants can be useful to achieve better reduction in particle size.

Example 6

½ Gallon 1S

A range of actives, matrices and surfactants in a variety of combinations were milled using the ½ gallon 1S mill. The details of these millings are shown in FIGS. 6A-C together with the particle size distributions of actives that were milled.

The following examples demonstrate the increased yield obtained when milling an active in a ½ gallon 1S attritor mill with a surfactant as compared to no surfactant, with all other factors being identical. Sample C and D (FIG. 6A) shows Naproxen acid milled in Mannitol with yields of 92% and 23%, with and without surfactant. Sample S and AL (FIGS. 6B and C) show the same for glyphosate with yields of 95% and 26%, respectively. Sample AI and AJ (FIG. 6B) show Ciprofloxacin yields of 94% and 37% with and without surfactant while sample AM an AN (FIG. 6C) show Celecoxib yields of 86% and 57% with and without surfactants. Finally, samples AP and AQ (FIG. 6C) shows milling Mancozeb with or without surfactants results in yields of 90% and 56%, respectively.

The following examples illustrates that milling an active in a ½ gallon 1S attritor mill with a surfactant as compared to without surfactant and all other factors identical, leads to smaller particle size after milling. Sample C and D (FIG. 6A) shows a D(0.5) of 0.181 and 0.319 with or without surfactant, while sample AM and AN (FIG. 6C) shows D(0.5) of 0.205 and 4.775 with and without surfactants.

The series of samples Q-S are timepoints taken from a single glyphosate milling. The data demonstrates that the size of the actives decreases with milling time.

Other samples such as V-AA show examples were surfactants suitable for use with IV formulations can be used to manufacture very small particles.

Some of the particle size data in FIGS. 6A-C was converted to a number average particle size and is shown in the tables. This number was calculated in the following way. The Volume distribution was transformed to the number distribution using the Malvern Mastersizer software. For each size bin the size of the bin was multiplied by the % of particles in the bin. This numbers were added together and divided by 100 to give the number average particle size.

Example 7

Metaxalone

Metaxalone was milled with various combinations of matrices and surfactants using a variety of mills. The details of these millings are shown in FIG. 7A together with the particle size distributions of actives that were milled. Samples A, B, E, G, H and I were milled in a Spex mill. Samples C, D and F were milled in the 750 ml atrittor. The remaining samples were milled in the ½ gallon 1S mill.

Samples A compared to sample B and sample H compared to sample G demonstrate that the addition of one or more surfactants enables the production of smaller active particles. Other millings such as samples C-F show that metaxalone can be milled small at very high active loadings. Sample I shows that disintegrant can be added during milling and not effect the production of small active particles. Note that the particle size in sample I is after filtration through a 10 micron filter. Sample N shows an alternative way to manufacture a formulation with small particles and disintegrants. In this example the powder from sample M was left in the mill and a wetting agent (PVP) and disintegrant were added. The powder was milled for a further 2 minutes and then unloaded with a very high yield of 97%.

The series of samples J-M are timepoints taken from a single milling. The data demonstrates that the size of the actives decreases with milling time.

Example 8

Hicom

A range of actives, matrices and surfactants in a variety of combinations were milled using the Hicom mill. The details of these millings are shown in FIG. 8A together with the particle size distributions of actives that were milled.

The data shows that the invention described herein can be used with the Hicom mill with its nutating action. The data in FIG. 8A shows that a variety of actives can be milled small in very short times and give very good yields at 500 gram scale.

Sample N and O show that cocoa powder can be reduced to very fine sizes in short times using the invention describes here in combination with the Hicom nutating mill. Likewise Sample P shows that this is also the case for cocoa nibs.

Example 9

1.5 Gallon 1S

A range of actives, matrices and surfactants in a variety of combinations were milled using the 1.5 Gallon 1S mill. The details of these millings are shown in FIGS. 9A-B together with the particle size distributions of actives that were milled.

The following examples demonstrate the increased yield obtained when milling an active in a 1.5 gallon 1S attritor mill with a surfactant as compared to no surfactant, with all other factors being identical. Sample J and N (FIG. 9A) shows yields of 51% and 80%, without and with surfactant. Sample K and P (FIG. 9A) show yields of 27% and 80%, without and with surfactant, while sample L (FIG. 9A) show a yield of 94% with surfactant and the control without surfactant (sample M, FIG. 9A) resulted in no yield due to caking within the mill.

The following examples illustrates that milling an active in a 1.5 gallon 15 attritor mill with a surfactant as compared to without surfactant and all other factors identical, leads to smaller particle size after milling. Sample F and G (FIG. 9A) shows a D(0.5) of 0.137 and 4.94 with or without surfactant, while sample K and P (FIG. 9A) shows D(0.5) of 0.242 and 0.152 without and with surfactants.

The series of samples AI-AL are timepoints taken from a single meloxicam milling. The data demonstrates that the size of the actives decreases with milling time.

Other samples such as A-E show examples were surfactants suitable for use with IV formulations can be used to manufacture very small particles.

Sample M was a milling of meloxicam in lactose monohydrate without surfactant. 3 minutes into the milling the mill refused to turn. The milling was stopped and started again but only ran for another 3 minutes before stopping again. At this point the mill was taken apart and no evidence of caking was found. However the powder had a gritty feeling to it and was locking the medium and shaft such that it was not possible to turn. The media was weighed and it as found that 150 grams of powder was on the media indicating that it was sticking to the media and making it hard to move. At this point the mill was re-assembled and the powder and media put back in. 30.4 grams of SDS was included in the milling making it similar to milling L. After the addition of the surfactant the mill was run for another 14 minutes (giving a total of 20 mins) without incident. After offloading the powder the media was weighed and the weigh of powder on the media was only 40.5 grams. This indicates the addition of surfactant has improved the milling performance and ability to mill the powder.

Some of the particle size data in FIGS. 9A-B was converted to a number average particle size and is shown in the tables. This number was calculated in the following way. The Volume distribution was transformed to the number distribution using the Malvern Mastersizer software. For each size bin the size of the bin was multiplied by the % of particles in the bin. This numbers were added together and divided by 100 to give the number average particle size.

Example 10

Large Scale 25/11 kg

Sample A (FIG. 10A) was milled in the Siebtechnik mill for 15 minutes. After this time the powder was completely caked onto the walls of the mill and the media. No powder could be removed to measure the particle size. At this point 0.25 g (1 w/w %) SLS was added to mill chamber and milling was then undertaken for a further 15 minutes. After the second period of milling in the presence of SLS powder was no longer caked onto the media and some free powder was also present. The observations made before and after the addition of the SLS demonstrate that the addition of the surfactant lessens the problem of caking. With the addition of surfactant the caked material could be recovered to become free powder again with small particle size.

Sample B-E was milled in horizontal Simoloyer mills. The details of these millings are shown in FIG. 10A together with the particle size distributions of actives that were milled.

The data shows that the invention described herein can be used with Simoloyer mills with their horizontal attritor action. Of particular note is example E which was milled at 11 kg scale. This demonstrates the invention described herein is suitable for commercial scale milling.

Sample F was milled in a vertical attritor mill (Union Process S-30). The details of this milling is shown in FIG. 10A together with the particle size distribution of the active milled.

The data shows that the invention described herein can be used with a S-30 mills with its vertical attritor action. Of particular note is that this milling was at 25 kg scale. This demonstrates the invention described herein is suitable for commercial scale milling.

Example 11

Naproxen

Naproxen was milled in mannitol with a range of surfactants using the ½ Gallon 1S mill. The details of these millings are shown in FIG. 11A together with the particle size distributions of actives that were milled.

Naproxen acid milled in Mannitol with a surfactant (Sample A, D-J in FIG. 11A) leads to higher yields, as compared to Naproxen acid milled in Mannitol without surfactant (Sample K, FIG. 11A). Naproxen acid milled in Mannitol and either microcrystalline cellulose or the disintegrant primellose (sample L or M, FIG. 11A) leads to small particle size with D(0.5) around 0.25 in both cases.

Example 12

Filtration

Some matrices, milling aids or facilitating agents that are used by this invention are not water soluble. Examples of these are microcrystalline cellulose and disintegrants such as croscarmellose and sodium starch glycolate. In order to more easily characterise the particle size of the active after milling with these materials filtration methods can be used to remove them allowing a characterisation of the active. In the following examples naproxen was milled with lactose monohydrate and microcrystalline cellulose (MCC). The particle size was characterised before and after filtration and the ability of the filters to let through the naproxen was demonstrated using HPLC assays. The milling details and the particle size are shown in FIG. 12a. Note in this table the particle size with milling details is un-filtered. The particle size in the rows with no milling details is after filtration. The sample that was filtered is indicated in the Active material section. The HPLC assays were performed by taking samples before and after filtration through 10 micron poroplast filters. The samples taken were diluted to give a nominal concentration of 100 µg/ml. The HPLC assay data is shown in Table 12

Sample A was milled with 5% MCC. Before filtration the D50 was 2.5 µm, after filtration (sample B) the D50 was 183 nm. When sample B was assayed the concentration was 94 µg/ml indicating that filtration process retained little naproxen. A second milling (sample C) was undertaken without MCC. The D50 was 160 nm as would be expected. After filtration (sample D) the particle size was unchanged indicating that if the filtration process did remove any naproxen then it was removed in an even way. Some of sample C was then milled with MCC for 1 minute. This is long enough to incorporate the MCC into the powder but not long enough to affect the particle size distribution. Two millings were undertaken. Sample E incorporated 5% w/w MCC into the powder and Sample F 9% w/w. After incorporation of the MCC the particle size increased dramatically. These samples where then filtered (Sample E and F) and the size remeasured. After filtration the particle size is the same as Sample C which was the starting material. The assay of samples E-H indicates that filtration did not remove any naproxen of any significance. The combination of particle size and assay data clearly shows that material such as MCC can easily and successfully be removed allowing the true particle size of the active to be measured.

Samples I and J were millings conducted with 10 and 20% w/w MCC. The particle size post filtration is show as sample K and L. Again the filtration has delivered a reduction in particle size due to the removal of the MCC component. And again the HPLC assay of sample I-L shows little naproxen was lost during filtration.

This data also demonstrates that MCC can successfully be used as co matrix in the invention disclosed herein.

TABLE 12

The HPLC assay of naproxen before and after filtration of samples.

| Sample No. | HPLC Assay (µg/ml) |
|---|---|
| B | 94 |
| D | 93 |
| E | 99 |
| F | 96 |
| G | 98 |
| H | 97 |
| I | 94 |
| J | 89 |
| K | 91 |
| L | 84 |

Example 13

Manufacture of Diclofenac Nanoformulation Capsules

Example 13(a)

18 mg

Diclofenac milled powder (666.2 g, from Example 9, Sample W) was charged into the bowl of a KG-5 high shear granulator. Separately, a 30% w/w solution of povidone K30 was prepared by dissolving 60.0 g of povidone K30 in 140.0 g of purified water. The granulator was operated at a chopper speed of 250 rpm and impeller speed of 2500 rpm. A portion of the povidone solution (88.6 g) was introduced into the granulation over a period of approximately 9 minutes with a peristaltic pump. An additional 30 g of water was then added to the granulation.

The wet granules were spread on to paper-lined trays and dried in an oven at 70° C. for 2 hours.

They were then manually screened through a 10 mesh hand screen. After approximately 2.25 hours of drying time, the loss on drying was determined to be 0.559%.

The dried granules were processed in a Quadro CoMill fitted with a 200 mesh screen and 0.225 inch spacer, run at 1265 rpm. The process yielded 539.0 g of milled, dried granules.

The granules were filled into size 4 white opaque hard gelatin capsules using an IN-CAP® automated capsule filling machine (Dott. Bonapace & C., Milano, Italy). The machine was set up with size 4 change parts and a 10 mm dosing disc. The target fill weight was 124.8 mg, and the average weight of an empty capsule shell was 38 mg. The machine was run at speed setting #2. Tamping pin #4 was set to 21 mm; all other tamping pin settings were N/A.

The filled capsules were polished in a capsule polishing machine, and the net yield of filled capsules was 480.2 g (approximately 2,910 capsules).

Example 13(b)

35 mg

Two separate granulation sublots were used for the manufacture of Diclofenac Nanoformulation Capsules 35 mg.

Granulation sublot A: 642.7 g of milled diclofenac powder (Example 9, Sample X) was charged into the bowl of a KG-5 high shear granulator. Separately, a 30% w/w solution of povidone K30 was prepared by dissolving 60.0 g of povidone K30 in 140.0 g of purified water. The granulator was operated at an impeller speed of 250 rpm and a chopper speed of 2500 rpm. A portion of the binder solution (85.5 g) was introduced into the granulation over a period of approximately 8.5 minutes via a peristaltic pump. An additional 30 g of purified water was then added to the granulation at the same rate. The wet granules were spread on to paper-lined trays to a thickness of approximately ½".

Granulation sublot B: 519.6 g of milled diclofenac powder (Example 9, Sample Y) was charged into the bowl of a KG-5 high shear granulator. Separately, a 30% povidone solution was prepared by dissolving 60.0 g of povidone K30 in 140.0 g of purified water. The granulator was operated at an impeller speed of 250 rpm and a chopper speed of 2500 rpm. A portion of the povidone solution (69.1 g) was added to the granulation over a period of approximately 6.5 minutes. An additional 30 g of water was then added at the same rate. The wet granules were spread on to paper-lined trays to a thickness of approximately ½".

The wet granules from sublots A and B were dried in an oven at 70° C. for approximately 2 hours. They were then manually screened through a 10 mesh hand screen and tested for loss on drying. The LOD result was 0.316%.

The dried granules were milled in a Quadro CoMill fitted with a 200 mesh screen and 0.225 inch spacer, operated at 2500 rpm. The milled granules were charged into an 8 qt V-blender and mixed for 5 minutes, yielding 1020.2 g of granules.

The granules were filled into size 3 white opaque hard gelatin capsules using a MiniCap Capsule Filling Machine equipped with size 3 change parts. The target fill weight was 242.7 mg and the average weight of an empty capsule shell was 47 mg. The granules were filled into the capsule shells manually using a scraper. Vibration and tamping were adjusted to achieve the target fill weight. The filled capsules were polished on a capsule polishing machine, yielding 1149.2 g of filled capsules (approximately 3,922 capsules).

Example 14

Dissolution Rate of Milled Diclofenac

In this example, dissolution rate is compared between 18 mg and 35 mg nanoformulations of the invention (Example 13(a) and 13(b)), and commercial reference diclofenac Voltarol Dispersible Tablets 50 mg (Novartis, U.K) which contain 46.5 mg of diclofenac free acid, equivalent to 50 mg of diclofenac sodium. The dissolution method used was Apparatus I (baskets) according to USP <711> with a stirring speed of 100 rpm. The dissolution media was 0.05% sodium lauryl sulfate and citric acid solution buffered to pH 5.75. The dissolution volume was 900 mL and dissolution medium temperature was 37° C. Samples were tested at 15, 30, 45, and 60 minutes and at infinity. Infinity was defined as an additional 15 minutes at a higher rotation speed. A sample of 1 ml was taken at each time point, filtered and assayed by HPLC with the detection wavelength set at 290 nm. The data in Table 14a below report the percent dissolved of the amount of active in each test article, for the specified time points.

TABLE 14a

Dissolution Profiles for Voltarol ® Dispersible Tablets 50 mg,
Diclofenac Nanoformulation Capsules 18 mg, and
Diclofenac Nanoformulation Capsules 35 mg

| Time | Percent Label Claim Dissolved (%) | | |
|---|---|---|---|
| | Voltarol Dispersible Tablets 50 mg | Diclofenac Nanoformulation Capsules 18 mg | Diclofenac Nanoformulation Capsules 35 mg |
| 0 | 0 | 0 | 0 |
| 15 | 52 | 91 | 82 |
| 30 | 59 | 94.0 | 95 |
| 45 | 63 | 94 | 95 |
| 60 | 65 | 94 | 95 |
| 75 | 87 | 94 | 95 |

The results demonstrate that the milled diclofenac capsules dissolve more quickly and more completely than the commercial reference diclofenac. Those of skill in the art will readily appreciate the advantages conferred by more rapid dissolution—more active agent is available at any given time point. Put another way, an equal quantity of dissolved diclofenac may be obtained with an initially smaller dosage amount of milled diclofenac, as opposed to the larger initial dose required for the reference diclofenac to reach to the same quantity of dissolved diclofenac. Additionally, as the results make clear, the reference diclofenac does not achieve complete dissolution even by the final time point, while the milled diclofenac achieves about 90% dissolution within 15 minutes. Again, a smaller dose of milled diclofenac yields a quantity of dissolved diclofenac for which a larger dose of reference diclofenac would be required to equal.

Example 15

Bioavailability of Milled Diclofenac

This example describes a Single-Dose, Five-Way Crossover, Relative Bioavailability Study of Diclofenac Nanoformulation 18 mg and 35 mg capsules and Cataflam® 50 mg Tablets in Healthy Subjects under Fed and Fasting Conditions.

The pharmacokinetic study described in this example used Diclofenac Nanoformulation Capsules 18 mg and 35 mg manufactured as described in Example 13(a) and 13(b).

Objectives:
1) To determine the relative bioavailability of diclofenac from the 35 mg Test capsule versus the 50 mg Reference tablet when administered to healthy subjects under fasting conditions.
2) To determine the effect of food on the rate and extent of absorption of a single dose of the 35 mg Test capsule formulation of diclofenac nanoformulation administered to healthy subjects under fed and fasting conditions.
3) To determine the effect of food on the rate and extent of absorption of a single dose of the 50 mg Reference tablet formulation of diclofenac potassium administered to healthy subjects under fed and fasting conditions.
4) To evaluate the dose proportionality between 18 mg and 35 mg Test capsule formulations of diclofenac nanoformulation administered to healthy subjects under fasting conditions.

Methodology:
This was a single-center, single-dose, randomized, open-label, 5-period, 5-treatment, 10-sequence crossover study that investigated the relative bioavailability and dose-proportionality of the Test product (i.e., 18 mg and 35 mg nanoformulation capsules of diclofenac acid) vs. the Reference product (50 mg immediate-release tablet of diclofenac potassium [Cataflam]) administered under fed and fasting conditions. Forty (40) healthy adult male and female subjects who met all study eligibility criteria were randomized equally on a 1:1:1:1:1 basis to one of 10 sequences of treatment administration. Each subject received 5 treatments in order of their assigned sequence according to the randomization code. Subjects entered the clinic on Day −1 of Treatment Period 1 and fasted overnight. On the morning of Day 1, subjects were administered the Test or Reference products in the fasted state or 30 minutes after the start of a FDA High-Fat Breakfast (depending on the study treatment). Blood samples for the pharmacokinetic (PK) evaluation of diclofenac plasma concentrations were obtained before and over 12 hours following dosing. Subjects were then discharged and returned to the clinic after a 7-day washout interval to continue the treatment sequence for Periods 2, 3, 4, and 5. A blood sample for safety assessments was collected with the last PK sample in Treatment Period 5.

Adverse event (AE) information elicited during confinement or reported at outpatient visits was reviewed and documented.

Number of Subjects (Planned and Analyzed):
Number of subjects planned for enrollment: up to 40
Number of subjects enrolled in study: 40
Number of subjects completing study: 38
Number of subjects bioanalytically analyzed: 30
Number of subjects statistically analyzed: 30

Diagnosis and Main Criteria for Inclusion:
Subjects were males and females who provided written informed consent, were at least 18 years of age, and had a body weight of at least 110 pounds and a body mass index (BMI) between 18 and 30 $kg/m^2$, and were healthy on the basis of medical history, physical examination, electrocardiogram (ECG), and clinical laboratory test results. All females were non-pregnant and non-nursing; females of child-bearing potential agreed to take precautions to prevent pregnancy. Eligibility criteria required that subjects demonstrate negative test results for hepatitis B, hepatitis C, and human immunodeficiency virus, as well as a negative urine screen for drugs of abuse and breathalyzer test for alcohol.

Test Product, Dose, and Mode of Administration:
The Test products were diclofenac acid nanoformulation 18 mg and 35 mg capsules.

The 18 mg Test product was administered as Treatment A. Subjects assigned to Treatment A received a single 18 mg capsule by mouth with 240 mL of water after an overnight fast.

The 35 mg Test product was administered as Treatments B and C. Subjects assigned to Treatment B received a single 35 mg capsule by mouth with 240 mL of water after an overnight fast. Subjects assigned to Treatment C received a single 35 mg capsule by mouth with 240 mL of water 30 minutes after the start of a FDA High-Fat Breakfast.

Duration of Treatment:
The duration of treatment was a single dose in each period.

Reference Therapy, Mode of Administration, and Lot Number:
The Reference product was Cataflam (diclofenac potassium) 50 mg tablets, manufactured by Patheon Inc, Whitby Operations and distributed by Novartis Pharmaceutical Corporation. A single lot of the Reference product was used in this study (Lot number C7C02722). The Reference product was administered as Treatments D and E. Subjects assigned to Treatment D received a single 50 mg tablet by mouth with 240 mL of water after an overnight fast. Subjects assigned to Treatment E received a single 50 mg tablet by mouth with 240 mL of water 30 minutes after the start of a FDA High-Fat Breakfast.

Criteria for Evaluation:

Pharmacokinetic:

Blood samples for measurement of diclofenac concentrations in plasma were collected pre-dose and 0.083, 0.167, 0.25, 0.33, 0.50, 0.67, 1, 1.33, 1.67, 2, 2.33, 2.67, 3, 3.67, 4, 4.5, 5, 6, 8, 10, and 12 hours post-dose. Primary PK variables included: area under the concentration-time curve from time zero to the time of the last sample with a quantifiable concentration ($AUC_{0-t}$); area under the concentration time curve from time zero extrapolated to infinity ($AUC_{0-\infty}$); and, measured maximal concentrations ($C_{max}$). Secondary PK variables included: time to reach maximum concentration ($T_{max}$); terminal elimination rate constant ($K_e$); and terminal elimination half-life ($T_{1/2}$).

Safety:

A physical examination, serology test for HIV, Hepatitis B, and Hepatitis C, as well as a urine drug screen were performed at the Screening Visit. Samples for general clinical laboratory tests were collected, 12-lead ECG tracings were obtained, vital signs were measured, and pregnancy tests (for female subjects) were performed at the Screening Visit and at specified time points. During the study, subjects were monitored for clinical and laboratory evidence of adverse events.

Statistical Methods:

Pharmacokinetic:

Statistical analyses were performed using the mixed model procedure of the SAS® statistical program (PC Version 9.1.3) in a Windows XP Professional environment. The pharmacokinetic parameter estimates were evaluated using mixed model analyses (PROC MIXED). The model included fixed effects for sequence, period, and treatment; and random effects for subject nested within sequence. The least-squares means and the mean standard error values from these analyses were used to construct the 90% confidence intervals for the relative bioavailability evaluations according to the FDA's recommended procedures. The dose normalized AUC and $C_{max}$ values for the 18 mg and 35 mg Test products were ln-transformed and compared by Analysis of Variance (ANOVA). As specified in the protocol, dose proportionality was to be concluded if the overall treatment effect was not significant at the 5% level, or if the 90% confidence intervals for the ratios of geometric means contained the value "1.00".

Safety:

Adverse events were coded using the Medical Dictionary for Regulatory Activities (MedDRA) and listed by system organ class (SOC) and preferred term (PT). Treatment-emergent AEs were summarized by incidence, relatedness to study drug, and severity.

Summary-Results

Demographic Characteristics of Subjects:

Forty (40) subjects were randomized into treatment and 38 subjects (95%) completed all 5 study periods. Two subjects voluntarily withdrew consent prior to dosing in Period 2. The 40 subjects who received at least one dose of study drug were included in the full analysis set and ranged in age from 21 to 56 years, with a mean age of 34.6 years. There were 27 male subjects (67.5%) and 13 female subjects (32.5%). With regard to race/ethnicity, 32 subjects (80.0%) were Black, 6 subjects (15.0%) were Caucasian, and 2 subjects (5.0%) were Hispanic. The mean height was 172.9 cm, with a range of 151 to 189 cm. The mean body weight was 77.4 kg, with a range of 52.9 to 104.8 kg. The mean BMI was 25.8 kg/m², with a range of 20.0 to 29.7 kg/m². Demographic findings were reflective of a healthy adult population.

Pharmacokinetic Results:

Consistent with the Statistical Analysis Plan, all available data from the first 30 of the 38 subjects who completed all 5 periods were used in the pharmacokinetic analyses. Statistical test results on pharmacokinetic parameters for diclofenac are summarized in the Tables 15a-d below.

TABLE 15a

Treatments B:D (35 mg Test product vs. 50 mg Reference product [fasting conditions])
35 mg Test product vs. 50 mg Reference product - Fasted subjects

| Pharmacokinetic Parameter/Unit | | Test Product 35 mg Fasted[a] | Reference Product 50 mg Fasted[a] | Ratio[b] | 90% CI[c] |
|---|---|---|---|---|---|
| $AUC_{(0-t)}$ | hr * ng/mL | 1132 | 1432 | 0.791* | 0.758, 0.825 |
| $AUC_{(0-\infty)}$ | hr * ng/mL | 1152 | 1449 | 0.795* | 0.764, 0.828 |
| $C_{max}$ | ng/mL | 1179 | 1268 | 0.930* | 0.789, 1.096 |
| $T_{max}$[d] | hr | 0.559 (0.500) | 0.737 (0.667) | 0.758 | — |
| $K_e$ | 1/hr | 0.3977 | 0.3763 | 1.057 | — |
| $T_{1/2}$ | hr | 1.83 | 1.92 | 0.956 | — |

$AUC_{(0-t)}$ and $AUC_{(0-\infty)}$ values for the Test (35 mg capsule) product were approximately 20% lower than observed for the Reference product (50 mg tablet). $C_{max}$ for the Reference product was only 7% greater than the Test product and was not statistically significant ($\alpha=0.05$). The 35 mg Test capsules and the 50 mg Reference tablets (Cataflam) were not bioequivalent when given to fasted subjects.

Abbreviations: ANOVA (analysis of variance); $AUC_{(0-t)}$ (area under the concentration-time curve from zero to the last measurable concentration); $AUC_{(0-\infty)}$ (area under the concentration-time curve from zero to infinity); CI (confidence interval); $C_{max}$ (measured maximal plasma concentration); $K_e$ (terminal elimination rate constant); $T_{1/2}$ (terminal elimination half life); $T_{max}$ (time to achieve maximum concentration).

a. Least-squares geometric means for areas and peak concentrations. Least squares arithmetic means for other parameters.

b. Ratio calculated as Test Fasted least-squares mean divided by the Reference Fasted least-squares mean.

c. Confidence interval on the Test-to-Reference ratio.

d. Mean (median) reported for $T_{max}$.

* Comparisons were detected as statistically significant with $\alpha=0.05$.

TABLE 15b

Treatments C:B (35 mg Test product [fed vs. fasted subjects])
Food reduced $AUC_{(0-t)}$ and $AUC_{(0-\infty)}$ values by 9% and 7%, respectively. $C_{max}$ decreased by 58%. All parameters were statistically significant ($\alpha = 0.05$) indicating a food effect for the 35 mg Test product.
35 mg Test product - Fed versus Fasted Subjects

| Pharmacokinetic Parameter/Unit | | Test Product | | | |
|---|---|---|---|---|---|
| | | 35 mg Fed[a] | 35 mg Fasted[a] | Ratio[b] | 90% CI[c] |
| $AUC_{(0-t)}$ | hr * ng/mL | 1034 | 1132 | 0.913* | 0.876, 0.952 |
| $AUC_{(0-\infty)}$ | hr * ng/mL | 1073 | 1152 | 0.931* | 0.893, 0.970 |
| $C_{max}$ | ng/mL | 490 | 1179 | 0.416* | 0.353, 0.489 |
| $T_{max}$[d] | hr | 1.93 (1.67) | 0.559 (0.500) | 3.445* | — |
| $K_e$ | 1/hr | 0.3275 | 0.3977 | 0.824* | — |
| $T_{1/2}$ | hr | 2.26 | 1.83 | 1.234* | — |

Abbreviations: ANOVA (analysis of variance); $AUC_{(0-t)}$ (area under the concentration-time curve from zero to the last measurable concentration); $AUC_{(0-\infty)}$ (area under the concentration-time curve from zero to infinity); CI (confidence interval); $C_{max}$ (measured maximal plasma concentration); $K_e$ (terminal elimination rate constant); $T_{1/2}$ (terminal elimination half life); $T_{max}$ (time to achieve maximum concentration).

a. Least-squares geometric means for areas and peak concentrations. Least squares arithmetic means for other parameters.

b. Ratio calculated as Test Fed least-squares mean divided by the Test Fasted least-squares mean.

c. Confidence interval on the Test Fed-to-Test Fasted ratio.

d. Mean (median) reported for $T_{max}$.

* Comparisons were detected as statistically significant by ANOVA, with α=0.05.

TABLE 15c

Treatments E:D (50 mg Reference product [fed vs. fasted Subjects]) Food reduced $AUC_{(0-t)}$ and $AUC_{(0-\infty)}$ by 9% and 8%, respectively. $C_{max}$ decreased by 27%. These PK parameters were statistically significant (α = 0.05), indicating a food effect for the Reference product.
50 mg Reference Product - Fed versus Fasted Subjects

| Pharmacokinetic Parameter/Unit | | Reference Product | | Ratio[b] | 90% CI[c] |
|---|---|---|---|---|---|
| | | 50 mg Fed[a] | 50 mg Fasted[a] | | |
| $AUC_{(0-t)}$ | hr * ng/mL | 1308 | 1432 | 0.914* | 0.877, 0.952 |
| $AUC_{(0-\infty)}$ | hr * ng/mL | 1334 | 1449 | 0.920* | 0.884, 0.958 |
| $C_{max}$ | ng/mL | 922 | 1268 | 0.728* | 0.619, 0.856 |
| $T_{max}$[d] | hr | 1.70 (1.33) | 0.737 (0.667) | 2.299* | — |
| $K_e$ | 1/hr | 0.3424 | 0.3763 | 0.910 | — |
| $T_{1/2}$ | hr | 2.17 | 1.92 | 1.134* | — |

Abbreviations: ANOVA (analysis of variance); $AUC_{(0-t)}$ (area under the concentration-time curve from zero to the last measurable concentration); $AUC_{(0-\infty)}$ (area under the concentration-time curve from zero to infinity); CI (confidence interval); $C_{max}$ (measured maximal plasma concentration); $K_e$ (terminal elimination rate constant); $T_{1/2}$ (terminal elimination half life); $T_{max}$ (time to achieve maximum concentration).

a. Least-squares geometric means for areas and peak concentrations. Least squares arithmetic means for other parameters.

b. Ratio calculated as Reference Fed least-squares mean divided by the Reference Fasted least-squares mean.

c. Confidence interval on the Reference Fed-to-Reference Fasted ratio.

d. Mean (median) reported for $T_{max}$.

* Comparisons were detected as statistically significant by ANOVA, with α=0.05.

TABLE 15d

Dose proportionality for Treatments A:B (18 mg vs. 35 mg Test Product [Fasted Subjects])
18 mg Test Product versus 35 mg Test Product - Fasted Subjects

| Pharmacokinetic Parameter/Unit | | Test Product | | Ratio[b] | 90% CI[c] |
|---|---|---|---|---|---|
| | | 18 mg Fasted[a] | 35 mg Fasted[a] | | |
| $AUC_{(0-t)}$ | hr * ng/mL | 1061 | 1132 | 0.938* | 0.899, 0.977 |
| $AUC_{(0-\infty)}$ | hr * ng/mL | 1090 | 1152 | 0.946* | 0.909, 0.984 |
| $C_{max}$ | ng/mL | 1174 | 1179 | 0.996* | 0.847, 01.172 |
| $T_{max}$[d] | hr | 0.571 (0.500) | 0.559 (0.500) | 1.022 | — |
| $K_e$ | 1/hr | 0.4760 | 0.3977 | 1.197* | — |
| $T_{1/2}$ | hr | 1.50 | 1.83 | 0.821* | — |

Dose-normalized ln-transformed $AUC_{(0-t)}$ and $AUC_{(0-\infty)}$ differences were statistically significant (α<0.05), and the 90% confidence intervals for their ratios did not contain the value "1.00", thus these parameters did not pass the per protocol dose-proportionality test. Alternatively, dose-proportionality may still be concluded for the 18 mg and 35 mg Test products since (1) the 90% confidence intervals of the ratios of the dose-normalized ln-transformed $C_{max}$, AUC, and AUC were totally contained within the 0.800 and 1.250 acceptance range for bioequivalence; and (2) the ratios of dose-normalized geometric means between the 18 mg and 35 mg Test capsules were 0.996, 0.938, and 0.946, respectively for $C_{max}$, $AUC_{(0-t)}$, and $AUC_{(0-\infty)}$.

Abbreviations: ANOVA (analysis of variance); $AUC_{(0-t)}$ (area under the concentration-time curve from zero to the last measurable concentration); $AUC_{(0-\infty)}$ (area under the concentration-time curve from zero to infinity); CI (confidence interval); $C_{max}$ (measured maximal plasma concentration); $K_e$ (terminal elimination rate constant); $T_{1/2}$ (terminal elimination half life); $T_{max}$ (time to achieve maximum concentration).

a. Least-squares geometric means for areas and peak concentrations. Least squares arithmetic means for other parameters. $AUC_{(0-t)}$, $AUC_{(0-\infty)}$, and $C_{max}$ for the 18 mg were dose-normalized by multiplying the ratio of 35 mg divided by 18 mg (equal to 1.944).

b. Ratio calculated as dose-normalized least-squares mean for the 18 mg Test product divided by the least-squares mean for the 35 mg Test product.

c. Confidence interval on the dose-normalized 18 mg Test-to-35 mg Test ratio.

d. Mean (median) reported for $T_{max}$.

* Comparisons were detected as statistically significant by ANOVA, with α=0.05.

Safety Results:

A total of 40 (100%) subjects were included in the safety population. Thirteen (13) treatment-emergent adverse events (AEs) were experienced by 7 subjects (18.0%). Six (6) treatment-emergent AEs were reported by 5 subjects (12.5%) who received the Test product and 7 treatment-emergent AEs were reported by 2 subjects (5.0%) who received the Reference product. Ten (10) of the 13 treatment-emergent AEs (76.9%) were considered to be mild in severity; 3 (23.0%) were considered to be moderate (i.e., vomiting and headache [Subject 15]) and none were serious or life-threatening. Fatigue was the treatment-emergent AD with the highest incidence overall, i.e., reported by 3 subjects (8.0%) who received the Test product (diclofenac nanoformulation 35 mg capsule). Six (6) out of 40 subjects (15.0%) reported 9 treatment-emergent AEs that were determined to be at least possibly related to study drug administration. No clinically significant changes in laboratory results or vital signs occurred, in the opinion of the Investigator. There were no deaths or other serious adverse events in this study.

Conclusions:

This was a single-center, single-dose, randomized, open-label, 5-period, 5-treatment 10-sequence crossover study that investigated the relative bioavailability and dose-proportionality of the Test product (i.e., 18 mg and 35 mg nanoformulation capsules of diclofenac acid) vs. the Reference product (50 mg immediate-release tablet of diclofenac potassium [Cataflam]) administered under fed and fasting conditions. Forty (40) healthy male and female adults were enrolled in the study. Eligible subjects received 5 treatments in order of their assigned sequence according to the randomization schedule. There was a 7-day washout interval between each Treatment Period. Thirty-eight (38; 95%) subjects completed all 5 study periods. Two 92; 5%) subjects voluntarily withdrew prior to dosing in Period 2. Pharmacokinetic blood samples were obtained pre-dose and over 12 hours following dosing. During the study, subjects were monitored for clinical and laboratory evidence of adverse events.

A single dose of diclofenac (18 mg, 35 mg, or 50 mg) was safe and well-tolerated. Seven subjects (7; 18.0%) reported a total of 13 treatment-emergent AEs. Six (6; 15%) subjects reported 9 treatment-emergent AEs that were determined to be at least possibly related to study drug administration. All treatment-emergent AEs were considered to be mild in severity, except for vomiting and 2 occurrences of headache experienced by Subject 15. No deaths or serious adverse events occurred.

All available data from the first 30 subjects who completed all 5 periods of the study were used in the pharmacokinetic analyses. Conclusions based on statistical testing of the PK parameters for diclofenac are summarized below.

35 mg Test Product vs. 50 mg Reference Product (Fasted Subjects):

These two formulations were not bioequivalent under fasting conditions since the 90% confidence intervals on the geometric mean and peak concentration ratios for diclofenac were outside the interval 0.800 to 1.250.

35 mg Test Product (Fed vs. Fasted Subjects):

Food decreased $AUC_{(0-t)}$ and $AUC_{(0-\infty)}$ values by 9% and 7% respectively. $C_{max}$ was decreased by 58%. Conversely, $T_{max}$ was 22 minutes slower when the 35 mg Test product was administered under fed conditions.

50 mg Reference Product (Fed vs. Fasted Subjects):

Food decreased $AUC_{(0-t)}$ and $AUC_{(0-\infty)}$ values by 9% and 8% respectively. $C_{max}$ was decreased by 27%. Conversely, $T_{max}$ was 58 minutes slower when the 50 mg Reference product was administered under fed conditions.

35 mg Test Product vs. 50 mg Reference Product (Fed Subjects):

These two formulations were not bioequivalent under fed conditions since the 90% confidence intervals on the geometric mean and peak concentration ratios for diclofenac were outside the interval 0.800 to 1.250.

Dose Proportionality Evaluation (18 mg vs. 35 mg Test Product in Fasted Subjects):

Although the 18 mg and 35 mg Test products were not identified as dose-proportional based on the per protocol analysis, dose-proportionality may still be concluded since: (1) the 90% confidence intervals for the ratios of dose-normalized ln-transformed $C_{max}$, $AUC_{(0-t)}$, and $AUC_{(0-\infty)}$ were totally contained within the 0.800 and 1.250 acceptance range for bioequivalence; and (2) the ratios of dose-normalized geometric means between the 18 mg and 35 mg Test capsules were 0.996, 0.938, and 0.946 respectively, for $C_{max}$, $AUC_{(0-t)}$, and $AUC_{(0-\infty)}$.

Example 16

Efficacy and Safety of Milled Diclofenac

This Example describes a Phase 2, Phase 2, Randomized, Double-Blind, Single-Dose, Parallel-Group, Active- and Placebo-Controlled Study of Diclofenac Nanoformulation Capsules for the Treatment of Pain After Surgical Removal of Impacted Third Molars.

The phase II efficacy study described in this example uses Diclofenac Nanoformulation Capsules 18 mg and 35 mg manufactured as described in Example 13(a) and (b).

Objectives:

The primary objective of this study is to evaluate the analgesic efficacy and safety of Diclofenac Nanoformulation Capsules compared with placebo in subjects with acute dental pain after third molar extraction. The secondary objective of this study is to evaluate the time to onset of analgesia for Diclofenac Nanoformulation Capsules compared with the standard formulation of celecoxib.

Number of Subjects:

Planned enrollment (and/or completion): Approximately 200 subjects (50 in each treatment group) will be enrolled.

Subject Population:

Inclusion Criteria:

A subject will be eligible for study entry if all of the following inclusion criteria are met:

1. Is male or female≥18 and ≤50 years of age.
2. Requires extraction of 2 or more third molars. At least 1 of the third molars must be a fully or partially bone-impacted mandibular molar. If only 2 molars are removed, then they must be ipsilateral.
3. Experiences moderate to severe pain intensity within 6 hours after surgery, as measured by a Visual Analog Scale (VAS) score of 50 mm on a 100-mm scale.
4. Has a body weight of 45 kg and a body mass index (BMI) 35 kg/m².
5. If female and of childbearing potential, is nonlactating and nonpregnant (has negative pregnancy test results at screening [serum] and on the day of surgery prior to surgery [urine]).
6. If female, is either not of childbearing potential (defined as postmenopausal for at least 1 year or surgically sterile [bilateral tubal ligation, bilateral oophorectomy, or hysterectomy]) or practicing 1 of the following medically acceptable methods of birth control:
    a. Hormonal methods such as oral, implantable, injectable, or transdermal contraceptives for a minimum of 1 full cycle (based on the subject's usual menstrual cycle period) before the study drug administration.
    b. Total abstinence from sexual intercourse (since the last menses before study drug administration).
    c. Intrauterine device (IUD).
    d. Double-barrier method (condoms sponge, diaphragm, or vaginal ring with spermicidal jellies or cream).
7. Is in good health, in the opinion of the investigator.
8. Is able to provide written informed consent to participate in the study and able to understand the procedures and study requirements.
9. Must voluntarily sign and date an informed consent form (ICF) that is approved by an Institutional Review Board (IRB) prior to the conduct of any study procedure.

10. Is willing and able to comply with study requirements (including diet and smoking restrictions), complete the pain evaluations, remain at the study site overnight, and return for follow-up 7±2 days after surgery.

Exclusion Criteria:

A subject will not be eligible for study entry if any of the following exclusion criteria are met:

1. Has a known history of allergic reaction or clinically significant intolerance to acetaminophen, aspirin, or any nonsteroidal anti-inflammatory drug (NSAIDs, including diclofenac and celecoxib); history of NSAID-induced bronchospasm (subjects with the triad of asthma, nasal polyps, and chronic rhinitis are at greater risk for bronchospasm and should be considered carefully); or hypersensitivity, allergy, or significant reaction to sulfa (including sulfonamide) medicines, ingredients of the study drug, or any other drugs used in the study including anesthetics and antibiotics that may be required on the day of surgery.
2. Has tested positive either on the urine drug screen or on the alcohol breathalyzer test. Subjects who test positive at screening only and can produce a prescription for the medication from their physician may be considered for study enrollment at the discretion of the investigator.
3. Has known or suspected history of alcoholism or drug abuse or misuse within 2 years of screening or evidence of tolerance or physical dependence before dosing with the study drug.
4. Has received or will require any medication (except hormonal contraceptives, vitamins, or nutritional supplements) within 5 half-lives (or, if half-life is unknown, within 48 hours) before dosing with study drug.
5. Has any clinically significant unstable cardiac, respiratory, neurological, immunological, hematological, or renal disease or any other condition that, in the opinion of the investigator, could compromise the subject's welfare, ability to communicate with the study staff, or otherwise contraindicate study participation.
6. Has a history or current diagnosis of a significant psychiatric disorder that, in the opinion of the investigator, would affect the subject's ability to comply with the study requirements.
7. Is receiving systemic chemotherapy, has an active malignancy of any type, or has been diagnosed with cancer with 5 years of screening (excluding squamous or basal cell carcinoma of the skin).
8. Has a history of clinically significant (investigator opinion) gastrointestinal (GI) event within 6 months before screening or has any history of peptic or gastric ulcers or GI bleeding.
9. Has a surgical or medical condition of the GI or renal system that might significantly alter the absorption, distribution, or excretion of any drug substance.
10. Is considered by the investigator, for any reason (including, but not limited to, the risks described as precautions, warnings, and contraindications in the current version of the Investigator's Brochure [IB] for Diclofenac Nanoformulation Capsules), to be an unsuitable candidate to receive the study drug.
11. Has history of chronic use (defined as daily use for >2 weeks) of NSAIDs, opiates, or glucocorticoids (except inhaled nasal steroids and topical corticosteroids), for any condition within 6 months before dosing with study drug. Aspirin at a daily dose of 325 mg is allowed for cardiovascular (CV) prophylaxis if the subject has been on a stable dose regimen for 30 days before screening and has not experienced any relevant medical problem.
12. Has a significant renal or hepatic disease, as indicated by the clinical laboratory assessment (results 3 times the upper limit of normal [ULN] for any liver function test, including aspartate aminotransferase [AST], alanine aminotransferase [ALT], and lactate dehydrogenase, or creatinine≥1.5 times the ULN) or has any clinically significant laboratory findings at screening that in the investigator's opinion contraindicate study participation.
13. Has significant difficulties swallowing capsules or is unable to tolerate oral medication.
14. Previously participated in another study of Diclofenac Nanoformulation Capsules, or received any investigational drug or device or investigational therapy within 30 days before screening.

Design:

This is a phase 2, multicenter, randomized, double-blind, single-dose, parallel-group, active- and placebo-controlled study to evaluate the efficacy and safety of Diclofenac Nanoformulation Capsules (18 mg and 35 mg) in subjects with postoperative dental pain. Eligible subjects will complete all screening procedures within 28 days before the surgery.

At screening, subjects will provide written informed consent to participate in the study before any protocol-specified procedures or assessments are completed. On Day 1, subjects who continue to be eligible for study participation after completing screening procedures and assessments are will undergo extraction of 2 or more third molars. At least 1 of the third molars must be a fully or partially bond-impacted mandibular molar. If only 2 molars are removed, then they must be ipsilateral. All subjects will receive local anesthesia (2% lidocaine with 1:100,000 epinephrine). Nitrous oxide will be allowed at the discretion of the investigator. Subjects who experience moderate to severe pain intensity (a score of 50 mm on a 100-mm VAS) within 6 hours after surgery and who continue to meet all study entry criteria will be randomized in a 1:1:1:1 ratio to receive 1 oral dose of Diclofenac Nanoformulation Capsules (18 mg or 35 mg), celecoxib capsules (400 mg), or placebo. Study drug will be administered by an unblended, third-party doser who will not conduct any efficacy or safety assessments.

Subjects will assess their baseline pain intensity (VAS) before receiving study drug (predose, Time 0) and their pain intensity (VAS) and pain relief (5-point categorical scale) at the following time points: 15, 30, and 45 minutes, and 1, 1.5, 2, 3, 4, 5, 6, 7, 8, 10, and 12 hours after Time 0; and immediately before the first dose of rescue medication. The 2-stopwatch method will be used to record the time to perceptible and time to meaningful pain relief, respectively. Subjects will complete a global evaluation of study drug 12 hours after Time 0 or immediately before the first dose of rescue medication (whichever occurs first). Vital signs will be recorded after the subject has been in a sitting position for 5 minutes at the following times: before surgery, before Time 0, 12 hours after Time 0, and/or immediately before the first dose of rescue medication. Adverse events (AEs) will be monitored and recorded from the time of signing of the ICF until the Follow-up Visit (or Early Termination Visit). During the 12 hours following Time 0, subjects will complete efficacy and safety assessments. Subjects will remain at the study site overnight and will be discharged the morning of Day 2. Upon discharge from the study site, subjects will be given a diary to record concomitant medications taken and AEs experienced after discharge.

Acetaminophen (1000 mg) will be permitted as the initial rescue medication. Subjects will be encouraged to wait at least 60 minutes after receiving study drug before taking rescue medication. Additional analgesic rescue medication may be administered at the discretion of the investigator if the protocol-specified rescue medication is deemed inadequate. Subjects are not permitted to take medications (except hormonal contraceptives, vitamins, nutritional supplements, and study drug) within 5 half-lives (or, if half-life is unknown, within 48 hours) before dosing with study drug until discharge from the study (Day 2). Other restrictions include the following: alcohol use is prohibited from 24 hours before surgery until discharge on Day 2; nothing by mouth (NPO) from midnight before surgery until 1 hour after surgery; clear liquids only are allowed starting 1 hour after surgery until 1 hour after dosing; 1 hour after dosing diet may be advanced according to standard practice.

Upon discharge from the study site, subjects may be prescribed pain medication for use at home according to the standard practice of the study site. On Day 8 (±2 days), subjects will return to the study site for an abbreviated confirmatory physical assessment and concomitant medication and AE assessments.

Study Drug:
  Diclofenac Nanoformulation Capsules (18 mg and 35 mg) for oral administration
Reference Products:
  Celecoxib 200-mg capsules administered as a 400-mg dose
Placebo
Treatment Regimens
  Eligible subjects meeting all study entry criteria will be randomized to receive 1 of the following treatments:
  One 18-mg Diclofenac Nanoformulation Capsule and 1 placebo capsule
  One 35-mg Diclofenac Nanoformulation Capsule and 1 placebo capsule
  Two 200-mg celecoxib capsules
  Two placebo capsules
Study Duration:
  Up to approximately 5 weeks for each subject, including a 4-week screening period and a posttreatment Follow-up Visit approximately 1 week after dosing with study drug.
Investigative Sites or Countries:
  Two study sites in the United States (US).
Study Endpoints:
Efficacy Endpoints:
  The primary efficacy endpoint is the sum of total pain relief (TOTPAR) over 0 to 12 hours (TOTPAR-12) after Time 0.
  The secondary endpoints are the following:
    TOTPAR over 0 to 4 hours (TOTPAR-4) and over 0 to 8 hours (TOTPAR-8) after Time 0.
    VAS pain intensity difference (VASPID) at each scheduled time point after Time 0.
    Time to onset of analgesia (measured as time to perceptible pain relief confirmed by meaningful pain relief).
    VAS pain intensity score at each scheduled time point.
    VAS summed pain intensity difference (VASSPID) over 0 to 4 hours (VASSPID-4), over 0 to 8 hours (VASSPID-8), and over 0 to 12 hours (VASSPID-12) after Time 0.
    Summed pain relief and intensity difference (sum of TOTPAR and VASSPID [SPRID]) over 0 to 4 hours (SPRID-4), over 0 to 8 hours (SPRID-8), and over 0 to 12 hours (SPRID-12) after Time 0.
    Pain relief score at each scheduled time point after Time 0.
    Peak pain relief.
    Time to peak pain relief.
    Time to first perceptible pain relief.
    Time to meaningful pain relief.
    Proportion of subjects using rescue medication.
    Time to first use of rescue medication (duration of analgesia).
    Patient's global evaluation of study drug.
Safety Endpoints:
  The safety endpoints are the incidence of treatment-emergent AEs (TEAEs) and changes in vital sign measurements.
Statistical Methods Summary:
Analysis Populations:
  The analysis populations include the following:
    The intent-to-treat (ITT) population will consist of all subjects who are treated with study drug and who have at least 1 pain relief assessment after Time 0. The ITT population is the primary population for the efficacy analysis.
    The per-protocol (PP) population will consist of all ITT subjects who remain in the study for at least 12 hours of treatment and who do not incur a major protocol violation that would challenge the validity of their data. This population will be utilized to evaluate the sensitivity of the primary efficacy analysis.
    The safety population will include all subjects who are treated with study drug. The safety population is the population for all safety assessments.
Subject Characteristics:
  Demographic and baseline characteristics (including age, sec, race, weight, height, BMI, medical history, surgery duration, and baseline values of efficacy variables) will be summarized for each treatment group and for the overall population by descriptive statistics. No formal statistical analyses will be performed.
Efficacy Analyses:
  The null hypothesis in this study is that TOTPAR-12 for placebo is equal to TOTPAR-12 for 35-mg Diclofenac Nanoformulation Capsules. It will be analyzed using analysis of covariance (ANCOVA) models, which include treatment effect and significant covariates. The effect of potential covariates, such as sex, baseline pain intensity, and surgical trauma rating, will be assessed using appropriate ANCOVA models. The analysis will be based on a 2-sided test as the significance level of 0.05.

Other comparisons between the treatment regimens, including 18-mg Diclofenac Nanoformulation Capsules versus placebo and 400-mg celecoxib capsules versus placebo will be considered secondary. No P value adjustment will be made for multiple endpoints or multiple comparisons. Each efficacy endpoint will be summarized descriptively by treatment group.

For continuous secondary endpoints such as pain intensity score, VASPID at each scheduled time point, peak pain intensity, TOTPAR-4, TOTPAR-8, VASSPID-4, VASSPID-8, VASSPID-12, SPRID-4, SPRID-8, and SPRID-12, descriptive statistics (such as mean, standard error, median, minimum, and maximum) will be provided for each treatment regimen. Nominal P values from 2-sample tests comparing the placebo group with other treatment groups will be provided, but no formal statistical inferences will be drawn on the basis of these tests.

For ordinal secondary endpoints, such as pain relief at each scheduled time point, peak pain relief, and global evaluation of study drug, descriptive summaries will be provided to include the number and percentage of subjects within each category for each treatment group. Nominal P values from Fisher's exact tests (or chi-square tests, as appropriate) comparing the placebo group with other treatment groups will be provided, but no formal statistical inferences will be drawn on the basis of these tests.

For each time-to-event endpoint, the Kaplan-Meier method will be used to evaluate the treatment effect. Time to onset of analgesia (measured as time to perceptible pain relief confirmed by meaningful pain relief) will be based on data collected using the 2-stopwatch method. Time to onset of analgesia will be right-censored at 12 hours for subjects who do not experience both perceptible pain relief and meaningful pain relief during the 12-hour interval after Time 0. The summary table will provide the number of subjects analyzed, the number of subjects censored, estimates for the quartiles, and 95% confidence intervals (CIs) for the estimated median and the restricted mean estimate. P values form the Wilcoxon or log-rank tests (as appropriate) will also be used to examine treatment effect. Cox proportional hazard models will be used to explore such potential covariates as sex, baseline pain intensity, and surgical trauma rating, if appropriate.

For the proportion of subjects using rescue medication, a logistic regression model that adjusts for baseline pain intensity, if appropriate, will be used to evaluate the treatment effect.

Subgroup analysis by sex may be performed if it is confirmed to be a statistically significant covariate for TOTPAR-12. Baseline values are defined as the last measurements taken before dosing with a study drug.

For pain intensity, missing observations will be imputed using baseline-observation-carried-forward (BOCF) for subjects who withdraw from the study due to lack of efficacy or an AE/intolerance to study drug. The BOCF imputation will be applied in place of all scheduled assessments after the time of early termination due to lack of efficacy or an AE/intolerance to study drug using the baseline observation taken before Time 0.

For subjects who withdraw from the study due to reasons other than lack of efficacy or an AE/intolerance to study drug, missing observations for pain intensity and pain relief will be imputed using last-observation-carried-forward (LOCF). The LOCF imputation will be applied in place of all scheduled assessments after the time of early termination due to reasons other than lack of efficacy or an AE/intolerance to the drug.

For subjects who take any dose of rescue medication, subsequent measures after the first dose of rescue medication will be disregarded. Instead, all scheduled assessments after the first dose of rescue medication will be imputed using BOCF using the baseline observation taken before Time 0. Single missing data points will be imputed using linear interpolation, if they do not occur at the end of the study. For other conditions before early termination or rescue medication, missing data will be imputed using LOCF.

Safety Analysis:

Data listings will be provided for protocol-specified safety data. The Medical Dictionary for Regulatory Activities (MedDRA) (Version 9.1 or higher) will be used to classify all AEs with respect to system organ class and preferred term. Adverse event summaries will include only TEAEs, which will be summarized for each treatment group. Fisher's 2-sided exact test will be used to compare the rates of occurrence between the placebo and Diclofenac Nanoformulation Capsule groups for all TEAEs.

For vital sign measurements, descriptive statistics will be provided at each scheduled time point for each treatment group. Changes from Baseline for vital signs will be calculated for each subject, and descriptive statistics will be provided on changes in vital signs from Baseline for each treatment group at each scheduled time point after Baseline. No formal statistical tests will be performed.

Sample Size:

The standard deviation of TOTPAR-12 is assumed to be 14.0. A sample size of 50 subjects per treatment group will provide 80% power to detect a minimal difference of 8.0 in TOTPAR-12 using a 2-sample t-test with a 0.05 two-sided significance level (nQuery v6.0).

TABLE 16a

Schedule of Events

| | | | $B^a$ | | | | | | | |
|---|---|---|---|---|---|---|---|---|---|---|
| | | | | | D | | | | | |
| | A | C | E | F | G | H | I | J | K |
| Written Informed Consent | X | | | | | | | | |
| Assign a screening number | X | | | | | | | | |
| Inclusion/exclusion criteria | X | X | | | | | | | |
| Demographics | X | | | | | | | | |
| Medical History | X | $X^b$ | | | | | | | |
| Physical Examination$^c$ | X | | | | | | | X | |
| Vital signs$^d$ | X | X | X | | | | | X | X |
| Height, weight, and BMI | X | | | | | | | | |
| Clinical laboratory tests (hematology, chemistry, urinalysis) | X | | | | | | | | |
| Pregnancy test for female subjects of childbearing potential$^e$ | X | X | | | | | | | |
| Urine drug screen | X | X | | | | | | | |
| Alcohol breathalyzer test | X | | | | | | | | |
| Oral radiography$^f$ | X | | | | | | | | |
| Review study restrictions with subject | X | | | | | | | | |
| Pain intensity (VAS)$^g$ | | | X | | X | X | X | | |
| Randomization | | X | | | | | | | |
| Dosing with study drug | | | | X | | | | | |
| Stopwatch assessment$^h$ | | | | X | | | | | |
| Pain relief (5-point categorical scale)$^g$ | | | | | X | X | X | | |
| Global evaluation of study drug$^i$ | | | | | | | X | | |
| Concomitant medications | | $X^b$ | X | X | X | X | X | X | X |
| Adverse events$^j$ | | X | X | X | X | X | X | X | X |
| Dispense rescue medication/ pain medications | | | | | | | | X | |
| Collect unused rescue medication/pain medications | | | | | | | | | X |
| Dispense/collect subject diary | | | | | | | | X | X |
| Discharge from study site | | | | | | | | X | |

$^a$ Times listed are relative to dosing with study drug.
$^b$ Medical history and concomitant medication use since screening will be updated on Day 1 before surgery.
$^c$ A complete physical examination (excluding the genitourinary examination) will be performed at screening. An abbreviated confirmatory physical assessment, including an examination of the subject's mouth and neck, will be performed at the Follow-Up visit (or Early Termination visit)
$^d$ Vital signs will be recorded after the subject has been in a sitting position for 5 minutes at the following times: at screening, before surgery, before Time 0, 12 hours after Time 0, and/or immediately before the first dose of rescue medication, and the Follow-up Visit (or Early Termination visit).
$^e$ Serum pregnancy test at screening and urine pregnancy test before surgery on Day 1 (female subjects of childbearing potential only). Test results must be negative for the subject to continue in the study.
$^f$ Oral radiographs taken within 1 year before screening will be acceptable and do not need to be repeated.
$^g$ Pain assessments will be conducted at 15, 30, and 45 minutes and 1, 1.5, 2, 3, 4, 5, 6, 7, 8, 10, and 12 hours after Time 0 and immediately before the first dose of rescue medication. Pain intensity will also be assessed predose. At each assessment time point, the pain intensity assessment will be completed first and the pain relief assessment will be completed second. Subjects will not be able to compare their responses with their previous responses.
$^h$ Two stopwatches will be started immediately after the subject has swallowed the study drug with 8 ounces of water (Time 0). Subjects will record the time to first perceptible and meaningful pain relief, respectively, by stopping the stopwatches.
$^i$ Subjects will complete a global evaluation of study drug 12 hours after Time 0 or immediately before the first dose of rescue medication (whichever occurs first).
$^j$ Adverse events will be monitored and recorded from the time of signing of the informed consent form (ICF) until the Follow-up Visit (or Early Termination visit).
A: Screening (Days −28 to −1); B: Day of Surgery (Day 1); C: Preop; D: Postop; E: Predose; F: 0 h; G: 15, 30, 45 min; H: 1, 1.5, 2, 3, 4, 5, 6, 7, 8, 10 h; I: 12 h; J: Day 2; K: Follow-up (Day 8±2 days or ET).

Abbreviations: BMI, body mass index; ET, early termination; h, hour; min, minute; preop, preoperative; postop, postoperative; VAS, Visual Analogue Scale.

The invention claimed is:

1. A method for treating pain comprising administering a solid oral unit dose of a pharmaceutical composition containing 18 mg of diclofenac acid to a subject, wherein the D(90) of the diclofenac acid, on a particle volume basis, is less than 5000 nm, and wherein the unit dose, when tested in vitro by USP Apparatus I (Basket) method of U.S. Pharmacopoeia at 100 rpm, at 37° C. in 900 ml of 0.05% sodium lauryl sulfate in citric acid solution buffered to pH 5.75, has a dissolution rate of diclofenac acid such that 94%, by weight, is released by 75 minutes.

2. The method of claim 1, wherein the D(90) of the diclofenac acid, on a particle volume basis, is less than 3000 nm.

3. The method of claim 2, wherein the unit dose has a dissolution rate of diclofenac acid such that 94%, by weight, is released by 60 minutes.

4. The method of claim 2, wherein the unit dose has a dissolution rate of diclofenac acid such that 94%, by weight, is released by 45 minutes.

5. The method of claim 2, wherein the unit dose has a dissolution rate of diclofenac acid such that 94%, by weight, is released by 30 minutes.

6. The method of claim 1, wherein the D(90) of the diclofenac acid, on a particle volume basis, is less than 2000 nm.

7. The method of claim 1, wherein the D(90) of the diclofenac acid, on a particle volume basis, is less than 1900 nm.

8. The method of claim 1, wherein the D(90) of the diclofenac acid, on a particle volume basis, is less than 1700 nm.

9. The method of claim 1, wherein the D(90) of the diclofenac acid, on a particle volume basis, is less than 1500 nm.

10. The method of claim 1, wherein the unit dose has a dissolution rate of diclofenac acid such that 94%, by weight, is released by 60 minutes.

11. The method of claim 1, wherein the unit dose has a dissolution rate of diclofenac acid such that 94%, by weight, is released by 45 minutes.

12. The method of claim 1, wherein the unit dose has a dissolution rate of diclofenac acid such that 94%, by weight, is released by 30 minutes.

13. The method of claim 1, wherein the pain is chronic pain or acute pain.

14. The method of claim 1, wherein the unit dose is administered at least once daily.

15. The method of claim 1, wherein a single unit dose provides perceptible pain relief.

16. A method for treating pain comprising administering a solid oral unit dose of a pharmaceutical composition containing 35 mg of diclofenac acid to a subject, wherein the D(90) of the diclofenac acid, on a particle volume basis, is less than 5000 nm, and wherein the unit dose, when tested in vitro by USP Apparatus I (Basket) method of U.S. Pharmacopoeia at 100 rpm at 37° C. in 900 ml of 0.05% sodium lauryl sulfate in citric acid solution buffered to pH 5.75, has a dissolution rate of diclofenac acid such that 95%, by weight, is released by 75 minutes.

17. The method of claim 16, wherein the D(90) of the diclofenac acid, on a particle volume basis, is less than 3000 nm.

18. The method of claim 17, wherein the unit dose has a dissolution rate of diclofenac acid such that 94%, by weight, is released by 60 minutes.

19. The method of claim 17, wherein the unit dose has a dissolution rate of diclofenac acid such that 94%, by weight, is released by 45 minutes.

20. The method of claim 17, wherein the unit dose has a dissolution rate of diclofenac acid such that 94%, by weight, is released by 30 minutes.

21. The method of claim 16, wherein the D(90) of the diclofenac acid, on a particle volume basis, is less than 2000 nm.

22. The method of claim 16, wherein the D(90) of the diclofenac acid, on a particle volume basis, is less than 1900 nm.

23. The method of claim 16, wherein the D(90) of the diclofenac acid, on a particle volume basis, is less than 1700 nm.

24. The method of claim 16, wherein the D(90) of the diclofenac acid, on a particle volume basis, is less than 1500 nm.

25. The method of claim 16, wherein the unit dose has a dissolution rate of diclofenac acid such that 94%, by weight, is released by 60 minutes.

26. The method of claim 16, wherein the unit dose has a dissolution rate of diclofenac acid such that 94%, by weight, is released by 45 minutes.

27. The method of claim 16, wherein the unit dose has a dissolution rate of diclofenac acid such that 94%, by weight, is released by 30 minutes.

28. The method of claim 16, wherein the pain is chronic pain or acute pain.

29. The method of claim 16, wherein the unit dose is administered at least once daily.

30. The method of claim 16, wherein a single unit dose provides perceptible pain relief.

* * * * *